United States Patent
Cywinska

(10) Patent No.: US 9,145,592 B2
(45) Date of Patent: Sep. 29, 2015

(54) QUALITATIVE/QUANTITATIVE DETECTION OF FUNGAL SPECIES

(76) Inventor: Alina Cywinska, Mississauga (CA)

( * ) Notice: Subject to any disclaimer, the term of this patent is extended or adjusted under 35 U.S.C. 154(b) by 785 days.

(21) Appl. No.: 13/303,237

(22) Filed: Nov. 23, 2011

(65) Prior Publication Data

US 2012/0129718 A1   May 24, 2012

Related U.S. Application Data

(60) Provisional application No. 61/416,800, filed on Nov. 24, 2010.

(51) Int. Cl.
| | | |
|---|---|---|
| *C12Q 1/68* | (2006.01) | |
| *C07H 21/02* | (2006.01) | |
| *C07H 21/04* | (2006.01) | |

(52) U.S. Cl.
CPC ............ *C12Q 1/6895* (2013.01); *C12Q 1/6837* (2013.01); *C12Q 2537/143* (2013.01); *C12Q 2563/107* (2013.01); *C12Q 2563/149* (2013.01); *C12Q 2565/501* (2013.01)

(58) Field of Classification Search
CPC .................................................... C12Q 1/6895
See application file for complete search history.

(56) References Cited

U.S. PATENT DOCUMENTS

| | | | |
|---|---|---|---|
| 5,707,802 A | 1/1998 | Sandhu et al. | |
| 5,876,930 A | 3/1999 | Livak et al. | |
| 5,919,617 A | 7/1999 | Bhattacharjee et al. | |
| 6,387,652 B1 | 5/2002 | Haugland et al. | |

OTHER PUBLICATIONS

Diaz, M. R. et al. Current Protocols in Cytometry, 13.9.1-13.9.21, (Apr. 2008).*
Hossain, M.A. et al., J. Allergy Clin. Immunol., vol. 113, pp. 200-208 (2004).*
Gunnbjörnsdóttir M I et al., "Prevalence and Incidence of Respiratory Symptoms in Relation to Indoor Dampness: the Rhine Study", *Thorax* 61:221-225 (2006).
Mudarri D. et al., "Public Health and Economic Impact of Dampness and Mold", *Indoor Air* 17:226-235 (2007).
Mendell M.J. et al., "Respiratory and Allergic Health Effects of Dampness, Mold, and Dampness-Related Agents: A Review of the Epidemiologic Evidence", *Environmental Health Perspectives* 119(6):748-756 (Jun. 2011).
Cywinska A. et al., "Identifying Canadian Mosquito Species Through DNA Barcodes", *Medical and Veterinary Entomology* 20(4):413-424 (2006).
Cywinska A. et al., "Evaluation of DNA Barcoding and Identification of New Haplomorphs in Canadian Deerflies and Horseflies", *Medical and Veterinary Entomology* 24, pp. 1-29 (2010).
Diaz M.R. et al., "High-Throughput Detection of Pathogenic Yeasts of the Genus Trichosporon", *Journal of Clinical Microbiology* 42(8):3696-3706 (Aug. 2004).
Haugland R.A. et al., "Quantitative PCR Analysis of Selected *Aspergillus, Penicillium* and *Paecilomyces* Species", *Systematic and Applied Microbiology* 27:198-210 (2004).

* cited by examiner

*Primary Examiner* — Teresa E Strzelecka
(74) *Attorney, Agent, or Firm* — Scully, Scott, Murphy & Presser P.C.

(57) ABSTRACT

A method based on species-specific molecular markers applied to a multiplex platform system is provided that permits, in a one-time assay, the qualitative and quantitative screening of multi-species populations in several dozens of environmental samples, tested in parallel, with low cost and rapid turn-around. The method identifies a specific portion of DNA, shared amongst a variety of important mold species, but with sufficient sequence differences that allow for unique identifications. Two pairs of primers, which are capable of amplifying this region across at least 38 different mold species, have been identified. Also short oligonucleotide probes have been designed specifically for each species to detect their presence and concentration in mixed species environmental samples. The method of detection of the invention can be practiced using conventional PCR reactions, followed by nucleotide hybridization assays and quantization of the hybridized biotinylated amplicons in a multiplex liquid array system.

20 Claims, 3 Drawing Sheets

SEQUENCE LISTING

<160> NUMBER OF SEQ ID NOS: 182

<210> SEQ ID NO 1
<211> LENGTH: 24
<212> TYPE: DNA
<213> ORGANISM: Artificial Sequence
<220> FEATURE:
<223> OTHER INFORMATION: Forward primer

<400> SEQUENCE: 1
gcatatcaat aagcggagga aaag                                          24

<210> SEQ ID NO 2
<211> LENGTH: 19
<212> TYPE: DNA
<213> ORGANISM: Artificial Sequence
<220> FEATURE:
<223> OTHER INFORMATION: Reverse primer

<400> SEQUENCE: 2
ggtccgtgtt tcaagacgg                                                19

<210> SEQ ID NO 3
<211> LENGTH: 22
<212> TYPE: DNA
<213> ORGANISM: Artificial Sequence
<220> FEATURE:
<223> OTHER INFORMATION: Forward primer

<400> SEQUENCE: 3
ggaagtaaaa gtcgtaacaa gg                                            22

<210> SEQ ID NO 4
<211> LENGTH: 17
<212> TYPE: DNA
<213> ORGANISM: Artificial Sequence
<220> FEATURE:
<223> OTHER INFORMATION: Reverse primer

<400> SEQUENCE: 4
cgccagttct gcttacc                                                  17

<210> SEQ ID NO 5
<211> LENGTH: 535
<212> TYPE: DNA
<213> ORGANISM: Penicillium purporogenum

<400> SEQUENCE: 5
tgcctcagta acggcgagtg aagcggcaag agctcaaatt tgaaatctgg cccctcggg     60 gtccgagttg taatttgcag aggatgcttc gggtgcggtc cccatctaag tgccctggaa   120
cgggccgtca tagagggtga gaatcccgtc tgggatgggc ggccgcgccc gtgtgaagct   180
ccttcgacga gtcgagttgt tgggaatgc agctctaagc gggtggtaaa tttcatctaa   240
agctaaatac tggccggaga ccgatagcgc acaagtagag tgatcgaaag atgaaaagca   300
ctttgaaaag agagttaaac agcacgtgaa attgttgaaa gggaagcgtt gtccaccaga   360
ctcgcccggg ggggttcagc cggcacgtgt gccggtgtac tcctctccgg gcgggccagc   420
atcggtttgg gcggctggtg aaaggccccg ggaatgtacc accctccggg gtgtcttata   480
gcccggggtg ccatacagcc agcctggacc gaggcccgcg cttcggcgag gatgc        535

<210> SEQ ID NO 6
<211> LENGTH: 514
<212> TYPE: DNA
<213> ORGANISM: Fusarium oxysporum

<400> SEQUENCE: 6

```
gattgcccta gtaacggcga gtgaagcggc aacagctcaa atttgaaatc tggctctcgg      60
gcccgagttg taatttgtag aggatacttt tgatgcggtg ccttccgagt tccctggaac     120
gggacgccat agagggtgag agccccgtct ggttggatgc caaatctctg taaagttcct     180
tcaacgagtc gagtagtttg gaatgctgc tctaaatggg aggtatatgt cttctaaagc      240
taaataccgg ccagagaccg atagcgcaca agtagagtga tcgaaagatg aaaagcactt     300
tgaaaagaga gttaaaaagt acgtgaaatt gttgaaaggg aagcgtttat gaccagactt     360
gggcttggtt aatcatctgg ggttctcccc agtgcacttt tccagtccag ccagcatca     420 gttttccccg ggggataaag gcggcgggaa tgtggctctc ttcggggagt gttatagccc     480
accgtgtaat accctggggg ggactgaggt tcgc                                 514
```

<210> SEQ ID NO 7
<211> LENGTH: 518
<212> TYPE: DNA
<213> ORGANISM: Aspergillus terreus

<400> SEQUENCE: 7

```
cctcagtaac ggcgagtgaa gcggcaagag ctcaaatttg aaagctggct ccttcggggt      60
ccgcattgta atttgcagag gatgcttcgg gtgcagcccc cgtctaagtg ccctggaacg     120
ggccgtcata gagggtgaga atcccgtatg gggcggggtg tctgcgtccg tgtgaagctc     180
cttcgacgag tcgagttgtt tgggaatgca gctctaaatg ggtggtaaat ttcatctaaa     240
gctaaatact ggccggagac cgatagcgca caagtagagt gatcgaaaga tgaaaagcac     300
tttgaaaaga gagttaaaca gcacgtgaaa ttgttgaaag ggaagcgctt gcaaccagac     360
tcgctcgcgg ggttcagccg gcttcggcc cggtgtactt ccccgcgggc gggccagcgt      420
cggtttgggc ggccggtcaa aggcctccgg aatgtagcgc ccttcggggc gccttatagc     480 cggggggtgca atgcggccag cctggaccga ggaacgcg                            518
```

<210> SEQ ID NO 8
<211> LENGTH: 537
<212> TYPE: DNA
<213> ORGANISM: Cladosporium cladosporioides

<400> SEQUENCE: 8

```
agggattgct ctagtaacgg cgagtgaagc agcaatagct caaatttgaa atctggcgtc      60
ttcgacgtcc gagttgtaat tgtagaggga tgcttctgag tggccaccga cctaagttcc     120
ttggaacagg acgtcataga gggtgagaat cccgtatgcg gtcggaaagg cgctctatac     180
gtagctcctt cgacgagtcg agttgtttgg gaatgcagct ctaaatggga ggtaaatttc     240
ttctaaagct aaatattggc cagagaccga tagcgcacaa gtagagtgat cgaaagatga     300
aaagcacttt ggaaagagag ttaaaaagca cgtgaaattg ttaaaaggga agggattgca     360
accagacttg ctcgcggtgt tccgccggtc ttctgaccgg tctactcgcc gcgttgcagg     420
ccagcatcgt ctggtgccgc tggataagac ttgaggaatg tagctccctc gggagtgtta     480
tagcctcttg tgatgcagcg agcgccgggc gaggtccgcg cttcggctag gatgctg       537
```

```
<210> SEQ ID NO 9
<211> LENGTH: 537
<212> TYPE: DNA
<213> ORGANISM: Aspergillus restrictus

<400> SEQUENCE: 9
ccgggattgc tcagtaacg gcgagtgaag cggcaaaagc tcaaatttga atctggccc      60 ctccggggtc cgagttgtaa tttgtagagg atgcttcggg tgcggccccc gtctaagtgc    120
tctggaatgg gccatcagag agggtgaaaa tcccgtctgg acggggtgt ccgcgtccgt    180 gtgaagctcc ttcgacgagt cgagttgttt ggaatgcag ctctaaatgg gtggtaaatt    240
tcatctaaag ctaaatattg gccggagacc gatagcgcac aagtagagtg atcgaaagat    300
gaaaagcact ttgaaaagag agttaaaaag cacgtgaaat tgttgaaagg gaagcacttg    360
cgaccagact cgcccacggg gttcagccgg ctttcgggcc ggtgtacttc cccgggggcg    420
ggccagcgtc ggtttgggcg gccggttaaa ggcccctgga atgtaacacc tctcggggtg    480
tcttatagcc agggtgcca tgcggccagc ccagaccgag gaacgcgctt cggcacg       537

<210> SEQ ID NO 10
<211> LENGTH: 615
<212> TYPE: DNA
<213> ORGANISM: Rhizopus oryzae

<400> SEQUENCE: 10
ctagtaacgg cgagtgaaga ggaaagagct caaagttgga acctgtttgg cctagctaaa     60
ccggattgta gactgtagaa gtgttttcca ggcaagccga gtaaataagt cctttggaac    120
agggcatcat agagggtgag aatcccgtct ttggcttgag catttgcctt ttgtgatacg    180
ctttcaaaga gtcaggttgt ttgggaatgc agcctaaatt gggtggtaaa tctcacctaa    240
agctaaatat tggcgagaaa ccgatagcga acaagtaccg tgagggaaag atgaaaagaa    300
ctttgaaaag agagttaaac agtatgtgaa attgttaaaa gggaaccgtt tggagccaga    360
ctggcttgtc tgtaatcaat ctaggcttcg gcctggatgc acttgcaggc tatgcctgcc    420
aacgacaatt tgacttgagg gaaaaaacta ggggaaatgt ggcccacttg tgggtgttat    480
agtcccttag aaaataccct tgggttggat tgaggaacgca gcgaatgctt attggcgagt    540
tttccaggaa ggttttctga ggtactacgg tatcaaggtt gatcttttg gttatacttc    600 tattcgctta ggttg                                                      615

<210> SEQ ID NO 11
<211> LENGTH: 545
<212> TYPE: DNA
<213> ORGANISM: Penicillium brevicompactum

<400> SEQUENCE: 11
agggattgcc ccagtaacgg cgagtgaagc ggcaagagct caaatttgaa agctggctcc     60
ttcggggtcc gcattgtaat ttgcagagga tgcttcggga cggtcccca tctaagtgcc    120 ctggaacggg acgtcataga gggtgagaat cccgtatggg atggggtgtc cgcgcccgtg    180
tgaagctcct tcgacgagtc gagttgtttg ggaatgcagc tctaaatggg tggtaaattt    240
catctaaagc taaatattgg ccggagaccg atagcgcaca agtagagtga tcgaaagatg    300
aaaagcactt tgaaaagaga gttaaaaagc acgtgaaatt gttgaaaggg aagcgcttgc    360
gaccagactc gctcgcgggg ttcagccggc attcgtgccg gtgtacttcc ccgcgagcgg    420
gccagcgtcg gtttgggcgg tcggtcaaag gcctctggaa ggtaacgccc cctcggggc     480
```

-continued

```
gtcttatagc cagggggtgca atgcggcctg cccggaccga ggaacgcgct tcggctcgga    540
cgctg                                                                 545

<210> SEQ ID NO 12
<211> LENGTH: 545
<212> TYPE: DNA
<213> ORGANISM: Penicillium miczynskii

<400> SEQUENCE: 12
ccctagtaac ggcgagtgaa gcggtaagag ctcaaatttg aaagctggcc ccttcggggt     60
ccgcattgta atttgcagag gatgcttcgg gagcggtccc catctaagtg ccctggaacg    120
ggccgtcata gagggtgaga atcccgtatg ggatggggtg cccgcgcccg tgtgaagctc    180
cttcgacgag tcgagttgtt tgggaatgca gctctaattg ggtggtaaat ttcatctaaa    240
gctaaatatt ggccggagac cgatagcgca caagtagagt gatcgaaaga tgaaaagcac    300
tttgaaaaga gagttaaaca gcacgtgaaa ttgttgaaag ggaagcgctt gcgatcagac    360
tcgctcgcgg ggttcagccg gccttcgggc cggtgtactt ccccgcgggc gggccagcgt    420
cggtttgggc ggccggtcaa aggcccctgg aatgtaacgc ctctcggggc gtcttatagc    480
caggggtgcc atgcggcctg cccggaccga ggaacgcgct tcggctcgga cgctggcata    540
atggt                                                                545

<210> SEQ ID NO 13
<211> LENGTH: 550
<212> TYPE: DNA
<213> ORGANISM: Ulocladium chartarum

<400> SEQUENCE: 13
gggattgccc tagtaacggc gagtgaagcg gcaacagctc aaatttgaaa tctggctctt     60
ttagagtccg agttgtaatt tgcagagggc gctttggctt tggcagcggt ccaagttcct    120
tggaacagga cgtcacagag ggtgagaatc ccgtacgtgg tcgctggcta ttgccgtgta    180
aagccccttc gacgagtcga gttgtttggg aatgcagctc taaatgggag gtacatttct    240
tctaaagcta atattggcc agagaccgat agcgcacaag tagagtgatc gaaagatgaa    300
aagcactttg gaaagagagt caaacagcac gtgaaattgt taaagggaa gcgcttgcag    360 ccagacttgc ttacagttgc tcatccgggc ttttgcccgg tgcactcttc tgtaggcagg    420
ccagcatcag tttgggcggt aggataaagg tctctgtcac gtacctcctt tcggggaggc    480 cttataggggg agacgacata ctaccagcct ggactgaggt ccgcgcatct gctaggatgc    540
tggcgtaatg                                                           550

<210> SEQ ID NO 14
<211> LENGTH: 516
<212> TYPE: DNA
<213> ORGANISM: Trichoderma viride

<400> SEQUENCE: 14
ccagtaacgg cgagtgaagc ggcaacagct caaatttgaa atctggcccc tagggtccga     60
gttgtaattt gtagaggatg cttttggtga ggtgccgccc gagttccctg gaacgggacg    120
ccgcagaggg tgagagcccc gtctggctgg ccaccgagcc tctgtaaagc tccttcgacg    180
agtcgagtag tttgggaatg ctgctcaaaa tgggaggtat atgtcttcta aagctaaata    240
ttggccagag accgatagcg cacaagtaga gtgatcgaaa gatgaaaagc acctgaaaa    300 gagggttaaa cagtacgtga aattgttgaa agggaagcgc ttgtgaccag acttgggcgc    360
```

```
ggcggatcat ccggggttct ccccggtgca cttcgccgtg ttcaggccag catcagttcg    420
gcgcggggga aaaaggcttc gggaacgtgg ctcctccggg agtgttatag cccgttgcat    480
aataccctgc gctggactga ggaccgcgca tctgca                              516

<210> SEQ ID NO 15
<211> LENGTH: 572
<212> TYPE: DNA
<213> ORGANISM: Penicillium chrysogenum

<400> SEQUENCE: 15
agggattgcc ccagtaacgg cgagtgaagc ggcaagagct caaatttgaa agctggctcc     60
ttcggggtcc gcattgtaat ttgtagagga tgcttcggga gcggtcccca tctaagtgcc    120
ctggaacggg acgtcataga gggtgagaat cccgtatggg atggggtgtc cgcgcccgtg    180
tgaagctcct tcgacgagtc gagttgtttg gaatgcagc tctaaatggg tggtaaattt     240
catctaaagc taaatattgg ccggagaccg atagcgcaca agtagagtga tcgaaagatg    300
aaaagcactt tgaaaagaga gttaaaaagc acgtgaaatt gttgaaaggg aagcgcttgc    360
gaccagactc gctcgcgggg ttcagccggc attcgtgccg gtgtacttcc ccgcgggcgg    420
gccagcgtcg gtttgagcgg tcggtcaaag gccctcggaa ggtaacgccc ctagggggcgt   480 cttatagccg agggtgcaat gcgacctgcc tagaccgagg aacgcgcttc ggctcggacg    540
ctggcataat ggtcgtaaac gacccgtctt ga                                  572

<210> SEQ ID NO 16
<211> LENGTH: 541
<212> TYPE: DNA
<213> ORGANISM: Penicillium spinulosum

<400> SEQUENCE: 16
attacctcag taacggcgag tgaagcggta agagctcaaa tttgaaagct ggctccttcg     60
gggtccgcat tgtaatttgc agaggatgtt tcgggagcag cccccatcta agtgtcctgg    120
aacggaccgt catagagggt gagaatcccg tatgggatgg ggtgtctgcg cccatgtgaa    180
actccttcga cgagtcgagt tgtttgggaa tgcagctcta aatgggtggt aaatttcatc    240
taaagctaaa tattgccgg agaccgatag cgcaagta gagtgatcga agatgaaaa       300 gcactttgaa aagagagtta aaaagcacgt gaaattgttg aagggaagc gcttgcgatc    360 agactcgcct tgggggttca gccggcattc gtgccggtgt acttcccca gggcgggcca    420 gcgtcggttt ggtggccgg tcaaaggccc ttggaatgta acgcctctcg ggcgtctta    480 tagccaaggg tgccatgcgg cctacctgga ccgaggaacg cgcttcggct cggacgctgg    540
c                                                                    541

<210> SEQ ID NO 17
<211> LENGTH: 521
<212> TYPE: DNA
<213> ORGANISM: Paecilomyces variotii

<400> SEQUENCE: 17
ccagtaacgg cgagtgaagc ggcaagagct caaatttgaa atctggcccc tccggggtcc     60
gagttgtaat ttgcagagga tgcttcgggc gcggtcccg tctaagtacc ctggaacggg    120
tcgtcataga gggtgagaat cccgtctggg acgggtggcc gtgtccgtgt gaagctcctt    180
cgacgagtcg agttgtttgg gaatgcagct ctaaatgggt ggtaaatttc atctaaagct    240
```

```
aaatattggc cggagaccga tagcgcacaa gtagagtgat cgaaagatga aaagcacttt      300
gaaaagagag ttaaacagca cgtgaaattg ttgaaaggga agcgcttgcg accagactcg      360
cccgcggggg ttcagccggt actcgtaccg gtgtactccc ccggggcgg gccagcgtcg       420 gtttgggcgg tcggtcaaag gcctccggaa tgtgtcgccc ccggggcgt cttatagccg       480 gaggtgcaat gcggccagcc tggaccgagg aacgcgcttc g                          521
```

```
<210> SEQ ID NO 18
<211> LENGTH: 533
<212> TYPE: DNA
<213> ORGANISM: Aspergillus candidus

<400> SEQUENCE: 18
tgcctcagta acggcgagtg aagcggcaag agctcaaatt tgaaagctgg ctccttcggg       60
gtccgcattg taatttgcag aggatgcttc gggtgcggcc cctgtctaag tgccctggaa      120
cgggctgtca gagagggtga gaatcccgtc tgggatgggg tgtccgcgcc cgtgtgaagc      180
tccttcgacg agtcgagttg tttgggaatg cagctctaaa tgggtggtaa atttcatcta      240
aagctaaata ttggccggag accgatagcg cacaagtaga gtgatcgaaa gatgaaaagc      300
actttgaaaa gagagttaaa cagcacgtga aattgttgaa agggaagcgc ttgcgaccag      360
actcgcccgc ggggttcagc cggcattcgt gccggtgtac ttccccgtgg gcgggccagc      420 gtcggttttgg gcgccggtc agcggctccc ggaatgtagc cctctcggg cgccttata       480 gccggggtg cagtgcggcc agcctggacc gaggaacgcg cttcggcacg gac              533
```

```
<210> SEQ ID NO 19
<211> LENGTH: 515
<212> TYPE: DNA
<213> ORGANISM: Aspergillus versicolor

<400> SEQUENCE: 19
ggcgagtgaa gcggcaagag ctcaaatttg aaatctggcc cctccggggt ccgagttgta       60
atttgcagag gatgcttcgg gtgcggcccc tgtctaagtg ccctggaacg ggccgtcaga      120
gagggtgaga atcccgtctt ggcagggtg cccgtgcccg tgtgaagctc cttcgacgag       180
tcgagttgtt tgggaatgca gctctaaatg ggtggtaaat ttcatctaaa gctaaatacc      240
ggccggagac cgatagcgca caagtagagt gatcgaaaga tgaaaagcac tttgaaaaga     300
gagttaaaca gcacgtgaaa ttgttgaaag ggaagcgctt gcgaccagac tcggcctcgg     360
ggttcagcca gcattcgtgc tggtgtactt ccccggggcc gggccagcgt cggttcgggc     420
ggccggtcaa aggccccagg aatgtatcgt cctccgggac gtcttatagc ctggggtgca     480
atgcggccag cctggaccga ggaacgcgct tcggc                                 515
```

```
<210> SEQ ID NO 20
<211> LENGTH: 543
<212> TYPE: DNA
<213> ORGANISM: Eurotium herbariorum

<400> SEQUENCE: 20
agggattgcc tcagtaacgg cgagtgaagc ggcaagagct caaatttgaa atctggcccc       60
tccggggtcc gagttgtaat tgtagagga tgcttcgggt gcggccccg tctaagtgct        120 ctggaacggg ccatcggaga gggtgagaat cccgtctggg acgggtgtc cgcgtccatg       180 tgaagctcct tcgacgagtc gagttgtttg ggaatgcagc tctaaatggg tggtaaattt      240
catctaaagc taaatactgg ccggagaccg atagcgcaca agtagagtga tcgaaagatg      300
```

```
aaaagcactt tgaaaagaga gttaaacagc acgtgaaatt gttgaaaggg aagcgcttgc    360
gaccagactc gcttccgggg ttcagccggc tttcgggccg gtgtacttcc ccgggggcgg    420
gccagcgtcg gtttgggcgg ccggtcaaag gcccctggaa tgtaacgccc ctcggggcgc    480
cttatagcca ggggtgtcat gcggccagcc tggaccgagg aacgcgcttc ggcacggacg    540
ctg                                                                 543

<210> SEQ ID NO 21
<211> LENGTH: 541
<212> TYPE: DNA
<213> ORGANISM: Penicillium corylophilum

<400> SEQUENCE: 21
tgcctcagta acggcgagtg aagcggcaag agctcaaatt tgaaagctgg ccccctcggg     60
gtccgcattg taatttgcag aggatgcttc gggagtggcc cccatctaag tgctctggaa    120
cgggccgtca tagagggtga gaatcccgta tgggatgggg tgtccgcgac catgtgaagc    180
tccttcgacg agtcgagttg tttgggaatg cagctctaaa tgggtggtaa atttcatcta    240
aagctaaata ttggccggag accgatagcg cacaagtaga gtgatcgaaa gatgaaaagc    300
actttgaaaa gagagttaaa aagcacgtga aattgttgaa agggaagcgc ttgcgaccag    360
actcgcctac ggggttcagc cggtattcgt accggtgtac ttccccgtgg gcgggccagc    420
gtcggtttgg gcggccggtc aaaggccctc ggaatgtaac gcctctcggg gcgtcttata    480
gccgagggtg ccatgcggcc agcccggacc gaggaacgcg cttcggcacg gacgctggca    540
t                                                                   541

<210> SEQ ID NO 22
<211> LENGTH: 533
<212> TYPE: DNA
<213> ORGANISM: Aspergillus sydowii

<400> SEQUENCE: 22
cctcagtaac ggcgagtgaa gcggcaagag ctcaaatttg aaatctggcc cctccggggt     60
ccgagttgta atttgcagag gatgcttcgg gtgcggcccc tgtctaagtg ccctggaacg    120
ggccgtcaga gagggtgaga atcccgtctt gggcagggtg cccgtgcccg tgtgaagctc    180
cttcgacgag tcgagttgtt tgggaatgca gctcaaaatg ggtggtaaat ttcatctaaa    240
gctaaatacc ggccggagac cgatagcgca caagtagagt gatcgaaaga tgaaaagcac    300
tttgaaaaga gagttaaaca gcacgtgaaa ttgttgaaag ggaagcgctt gcaaccagac    360
tcggcctcgg ggttcagcca gcattcgtgc tggtgtactt ccccggggcc gggccagcgt    420
cggtttgggc ggccggtcaa aggccccagg aatgtatcgt cctccgggac gtcttatagc    480
ctggggtgca atgcggccag cctggaccga ggaacgcgct tcggcacgga cgc           533

<210> SEQ ID NO 23
<211> LENGTH: 569
<212> TYPE: DNA
<213> ORGANISM: Wallemia sebi

<400> SEQUENCE: 23
aaggattccc ctagtaacgg cgagtgaaga gggaaaagct caaatttaaa agctgttgtc     60
tttcaggcaa ccgcattgta atctcaagaa gtgttttcga ttgtagcctg cgtataagta    120
ccttggaata ggttggcata gagggtgaaa ctcccgtctt tgatgcagat tactatgatc    180
```

```
atgtgataca ctttctaaga gtcgagttgt ttgggaatgc agctcaaaat gggtggtaaa      240
ttccatctaa agctaaatat tggcctgaga ccgatagcga acaagtaccg tgagggaaag      300
atgaaaagca ctttggaaag agagtcaaac agaacgtgaa attgctgaaa gggaagcgtt      360
tgaagttagt ctgatagaag ttgttcaatt gttactttgg tttcaatgta tgcaactttt      420
tatcggtcaa catcaatttt gattgatgga taaaggtaat aggaatgtgg ctacatttgt      480
agtgttatag actattatca aaacattgat tgagattgag acggcagtg tacctttag       540 gaaggtgttc gcacctatta cactaagga                                        569

<210> SEQ ID NO 24
<211> LENGTH: 540
<212> TYPE: DNA
<213> ORGANISM: Penicillium decumbens

<400> SEQUENCE: 24
gggattgcct cagtaacggc gagtgaagcg gcaagagctc aaatttgaaa gctggccccc       60
tcggggtccg cattgtaatt tgcagaggat gcttcgggag tggcccccat ctaagtgctc      120
tggaacgggc cgtcatagag ggtgagaatc ccgtatggga tggggtgtcc gcgaccatgt      180
gaagctcctt cgacgagtcg agttgtttgg gaatgcagct ctaaatgggt ggtaaatttc      240
atctaaagct aaatattggc cggagaccga tagcgcacaa gtagagtgat cgaaagatga      300
aaagcacttt gaaaagagag ttaaaaagca cgtgaaattg ttgaagggaa gcgcttgcg       360 accagactcg cctgcggggt tcagccggta ttcgtaccgg tgtacttccc cgtgggcggg      420
ccagcgtcgg tttgggcggc cggtcaaagg ccctcggaat gtaacgcctc tcggggcgtc      480
ttatagccga gggtgccatg cggccagccc ggaccgagga acgcgcttcg gcacggacgc      540

<210> SEQ ID NO 25
<211> LENGTH: 529
<212> TYPE: DNA
<213> ORGANISM: Scopulariopsis candida

<400> SEQUENCE: 25
attgccccag taacggcgag tgaagcggca acagctcaaa tttgaaatct ggtcccctttt      60 gggggcccga gttgtaattt gaagaggatg cttttggcga ggcgccgtcc gagttccctg      120
gaacgggacg ccgcagaggg tgagagcccc gtacggtcgg acgccgagcc tctgtaaagc      180
tccttcgacg agtcgagtag tttgggaatg ctgctcaaaa tgggaggtaa accccttcta      240
aagctaaata ccggccagag accgatagcg cacaagtaga gtgatcgaaa gatgaaaagc      300
actttgaaaa gagagttaaa aagcacgtga aattgttaaa agggaagcgc ttgcgaccag      360
acttgcgccc gtcggatcaa ccgtcgcttg cggcggcgca ctccggcggg ctcaggccag      420
catcagttcg cctgggggga gaaggcggc gggaatgtgg ctcttcggag tgttatagcc       480
cgcccgtgta ataccctcgg gtggactgag gaccgcgcgt atgcaagga                  529

<210> SEQ ID NO 26
<211> LENGTH: 646
<212> TYPE: DNA
<213> ORGANISM: Mucor plumbeus

<400> SEQUENCE: 26
gatttcccta gtaacggcga gtgaagagga aagagctcaa agttggaacc tgtttggctt       60
agctaaaccg gattgtaaac tgtagaaaca ttttccagat acactagaca aaaaagtcct      120
ttggaacagg gcatcataga gggtgagaat cccgtctttg gtctaagtag ttgtctattg      180
```

```
tgatatgttt tcaaagagtc aggttgtttg ggaatgcagc ctaaatttggg tggtaaatct    240 cacctaaagc taaatatttg cgagagaccg atagcgaaca agtaccgtga gggaaagatg    300
aaaagaactt tgaaaagaga gttaaacagt atgtgaaatt gttaaaaggg aaccgtttgg    360
agccagactg gcttgattgt aatcaaccta gaattcgttt tgggtgcact tgcagtctat    420
gcctgccaac gacagtttga tttggaggaa aaaattaata ggaatgtggc ctctcgaggt    480
gttatagcct attatcatac tctggattgg actgaggaac gcagtgaatg cctttaggca    540
agattgctgg gcgctttcgc taataaatgt tagaatttct gcttcgggtg gtgctaatgt    600
ttaaaggagg aactcgttta gtatattttt tattcgctta ggttgt                   646

<210> SEQ ID NO 27
<211> LENGTH: 506
<212> TYPE: DNA
<213> ORGANISM: Penicillium citreonigrum

<400> SEQUENCE: 27
aaatttgaaa gctggccccc tcggggtccg cattgtaatt tgcagaggat gcttcgggag     60
tggcccccat ctaagtgctc tggaacgggc cgtcatagag ggtgagaatc ccgtatggga    120
tggggtgtcc gcgaccatgt gaagctcctt cgacgagtcg agttgtttgg gaatgcagct    180
ctaaatgggt ggtaaatttc atctaaagct aaatattggc cggagaccga tagcgcacaa    240
gtagagtgat cgaaagatga aaagcacttt gaaaagagag ttaaaaagca cgtgaaattg    300
ttgaaaggga agcgcttgcg accagactcg cctacgggt tcagccggta ttcgtaccgg    360
tgtacttccc cgtgggcggg ccagcgtcgg tttggcggc cggtcaaagg ccctcggaat    420
gtaacgcctc tcggggcgtc ttatagccga gggtgccatg cggccagccc agaccgagga    480
acgcgcttcg gcacggacgc tggcat                                         506

<210> SEQ ID NO 28
<211> LENGTH: 537
<212> TYPE: DNA
<213> ORGANISM: Aspergillus flavus

<400> SEQUENCE: 28
tgcctcagta acggcgagtg aagcggcaag agctcaaatt tgaaagctgg ctccttcggg     60
gtccgcattg taatttgcag aggatgcttc gggtgcggcc cctgtctaag tgccctggaa    120
cgggccgtca gagagggtga gaatcccgtc tgggatgggg tgtccgcgcc cgtgtgaagc    180
tccttcgacg agtcgagttg tttgggaatg cagctctaaa tgggtggtaa atttcatcta    240
aagctaaata ctggccggag accgatagcg cacaagtaga gtgatcgaaa gatgaaaagc    300
actttgaaaa gagagttaaa aagcacgtga aattgttgaa agggaagcgc ttgcgaccag    360
actcgcctcc agggttcagc cggcattcgt gccggtgtac ttccctgggg cgggccagc    420 gtcggtttgg gcggccggtc aaaggctccc ggaatgtagt gccctccggg gcaccttata    480
gccgggagtg caatgcggcc agcctggacc gaggaacgcg cttcggcacg gacgctg      537

<210> SEQ ID NO 29
<211> LENGTH: 540
<212> TYPE: DNA
<213> ORGANISM: Aspergillus ochraceus

<400> SEQUENCE: 29
gattgcctca gtaacggcga gtgaagcggc aagagctcaa atttgaaatc tggccccctc     60
```

```
ggggtccgag ttgtaatttg cagaggatgc ttcgggtgcg gccccgtct aagtgccctg      120 gaacgggccg tcatagaggg tgagaatccc gtctgggacg gggtgtccgc gtccgtgtga      180
agctccttcg acgagtcgag ttgtttggga atgcagctct aaatgggtgg taaatttcat      240
ctaaagctaa atactggccg gagaccgata gcgcacaagt agagtgatcg aaagatgaaa      300
agcactttga aaagagagtt aaaaagcacg tgaaattgtt gaaagggaag cgcttgcgac      360
cagactcgcc cgcggggttc agccggcatt cgtgccggtg tacttccccg cgggcgggcc      420
agcgtcggtt tgggcggccg gtcaaaggcc cccggaatgt agcacccttc ggggtgcctt      480
atagccgggg gtgcaatgcg gccagcctgg accgaggaac gcgcttcggc acggacgctg      540
```

<210> SEQ ID NO 30
<211> LENGTH: 546
<212> TYPE: DNA
<213> ORGANISM: Aspergillus penicillioides

<400> SEQUENCE: 30

```
gggattgcct cagtaacggc gagtgaagcg gcaagagctc aaatttgaaa tctggcccct      60
ccggggtccg agttgtaatt tgtagaggat gcttcgggtg cggcccctgt ctaagtgccc     120
tggaacgggc catcggagag ggtgagaatc ccgtctggga tggggtgtcc gtgcccgtgt     180
gaagctcctt cgacgagtcg agttgtttgg gaatgcagct ctaaatgggt ggtaaatttc     240
atctaaagct aaatactggc cggagaccga tagcgcacaa gtagagtgat cgaaagatga     300
aaagcacttt gaaagagag ttaaacagca cgtgaaattg ttgaaaggga agcgcttgcg     360
accagactcg cccacggggt tcagccggct ttcgggccgg tgtacttccc cggggcggg     420 ccagcgtcgg tttgggcggc cggtcaaagg cccccggaat gtaacgcccc tccggggcg     480 tcttatagcc ggggggtgtca tgcggccagc ctagaccgag gaacgcgctt cggcacggac     540
gctggc                                                                546
```

<210> SEQ ID NO 31
<211> LENGTH: 535
<212> TYPE: DNA
<213> ORGANISM: Scopulariopsis brevicaulis

<400> SEQUENCE: 31

```
gggattgcct tagtaacggc gagtgaagcg gcaacagctc aaatttgaaa tctggtcccc      60
tttgggggcc cgagttgtaa tttgaagagg atgcttttgg cgaggcgccg tccgagttcc     120
ctggaacggg acgccgcaga gggtgagagc ccgtacggt cggacgccga gcctctgtaa     180
agctccttcg acgagtcgag tagtttggga atgctgctca aaatgggagg taaaccccctt     240 ctaaagctaa atactggcca gagaccgata gcgcacaagt agagtgatcg aaagatgaaa     300
agcactttga aaagagagtt aaaaagcacg tgaaattgtt aaaagggaag cgcttgcgac     360
cagacttgcg cccgtcggat caaccgtcgc ttgcggcggc gcactccggc gggctcaggc     420
cagcatcagt tcgtccgggg ggagaaaggc ggcgggaatg tggctcttcg gagtgttata     480
gcccgccgtg taataccctc gggtggactg aggaccgcgc gtatgcaagg atgct          535
```

<210> SEQ ID NO 32
<211> LENGTH: 528
<212> TYPE: DNA
<213> ORGANISM: Aspergillus ustus

<400> SEQUENCE: 32

```
gattgcctca gtaacggcga gtgaagcggc aagagctcaa atttgaaatc tggcccctcc      60
```

```
ggggtccgag ttgtaatttg cagaggatgc ttcgggtgcg gccctgtct  aagtgccctg     120 gaacgggccg tcagagaggg tgagaatccc gtcttgggca gggtgccgt  gcccgtgtga     180 agctccttcg acgagtcgag ttgtttggga atgcagctct aaatgggtgg taaatttcat     240
ctaaagctaa ataccggccg agaccgata  gcgcacaagt agagtgatcg aaagatgaaa     300
agcactttga aaagagagtt aaacagcacg tgaaattgtt gaaagggaag cgcttgcgac     360
cagactcggc cccggggttc agccagcact cgtgctggtg tacttcccg  ggggcgggcc     420 agcgtcggtt tgggcggccg gtcaaaggcc ccaggaatgt gtcgccctcc ggggcgtctt     480
atagcctggg gtgcaatgcg gccagcccgg accgaggaac gcgcttcg              528

<210> SEQ ID NO 33
<211> LENGTH: 518
<212> TYPE: DNA
<213> ORGANISM: Aspergillus sclerotiorum

<400> SEQUENCE: 33
cggcgagtga agcggcaaga gctcaaattt gaaatctggc cccctcgggg tccgagttgt      60
aatttgcaga ggatgcttcg ggtgcggccc ccgtctaagt gccctggaac gggccgtcat     120
agagggtgag aatcccgtct gggacggggt gtccgcgtcc gtgtgaagct ccttcgacga     180
gtcgagttgt ttgggaatgc agctctaaat ggtggtaaa  tttcatctaa agctaaatac     240
tggccggaga ccgatagcgc acaagtagag tgatcgaaag atgaaaagca ctttgaaaag     300
agagttaaaa agcacgtgaa attgttgaaa gggaagcgct tgcgaccaga ctcgcccgcg     360
gggttcagcc ggcattcgtg ccggtgtact tccccgcggg cgggccagcg tcggtttggg     420
cggccggtca aaggccccg  gaatgtagtg ccctacgggg gcaccttat  agccggggt     480 gcaatgcggc cagcctggac cgaggaacgc gcttcggc                             518

<210> SEQ ID NO 34
<211> LENGTH: 541
<212> TYPE: DNA
<213> ORGANISM: Alternaria alternata

<400> SEQUENCE: 34
gggattgccc tagtaacggc gagtgaagcg gcaacagctc aaatttgaaa tctggctctt      60
ttagagtccg agttgtaatt tgcagagggc gctttggctt tggcagcggt ccaagttcct     120
tggaacagga cgtcacagag ggtgagaatc ccgtacgtgg tcgctggcta ttgccgtgta     180
aagccccttc gacgagtcga gttgtttggg aatgcagctc taaatgggag gtacatttct     240
tctaaagcta atattggcc  agagaccgat agcgcacaag tagagtgatc gaaagatgaa     300
aagcactttg aaagagagt  caaacagcac gtgaaattgt tgaaagggaa gcgcttgcag     360
ccagacttgc ttacagttgc tcatccgggt ttttacccgg tgcactcttc tgtaggcagg     420
ccagcatcag tttgggcggt aggataaagg tctctgtcac gtacctcctt tcggggaggc     480
cttatagggg agacgacata ctaccagcct ggactgaggt ccgcgcatct gctaggatgc     540
t                                                                     541

<210> SEQ ID NO 35
<211> LENGTH: 555
<212> TYPE: DNA
<213> ORGANISM: Candida glabrata

<400> SEQUENCE: 35
```

```
tgggattgcc ttagtaacgg cgagtgaagc ggcaaaagct caaatttgaa atctggtacc      60
tttggtgccc gagttgtaat ttggagagta ccactttggg actgtacttt gcctatgttc     120 cttgaacag gacgtcatgg agggtgagaa tcccgtgtgg cgagggtgtc agttctttgt      180
aaagggtgct cgaagagtcg agttgtttgg gaatgcagct ctaagtgggt ggtaaattcc     240
atctaaagct aaatacaggc gagagaccga tagcgaacaa gtacagtgat ggaaagatga     300
aaagaacttt gaaagagag tgaaaaagta cgtgaaattg ttgaaaggga agggcatttg      360
atcagacatg gtgttttgcg ccccttgcct ctcgtgggct gggactctc gcagctcact      420 gggccagcat cggttttggc ggccggaaaa aacctaggga atgtggctct gcgcctcggt     480
gtagagtgtt atagccctgg ggaatacggc cagtcgggac cgaggactgc gatacttgtt    540
atctaggatg ctggc                                                     555

<210> SEQ ID NO 36
<211> LENGTH: 539
<212> TYPE: DNA
<213> ORGANISM: Phoma glomerata

<400> SEQUENCE: 36
ggattgccct agtaacggcg agtgaagcgg caacagctca aatttgaaat ctggcgtctt     60
tggcgtccga gttgtaattt gcagagggcg ctttggcatt ggcagcggtc caagttcctt   120
ggaacaggac gtcacagagg gtgagaatcc cgtacgtggt cgctagcctt taccgtgtaa   180
agccccttcg acgagtcgag ttgtttggga atgcagctct aaatgggagg taaatttctt   240
ctaaagctaa atactggcca gagaccgata gcgacaagt agagtgatcg aaagatgaaa    300
agcactttgg aaagagagtt aaaaagcacg tgaaattgtt gaagggaag cgcttgcagc    360 cagacttgcc tgtagttgct catccgggtt tctacccggt gcactcttct ataggcaggc    420
cagcatcagt ttgggcggtt ggataaaggt ctctgtcatg tacctccttt cggggagaac    480 ttataggggag acgacatgc aaccagcctg gactgaggtc cgcgcatctg ctaggatgc     539

<210> SEQ ID NO 37
<211> LENGTH: 542
<212> TYPE: DNA
<213> ORGANISM: Aureobasidium pullulans
<220> FEATURE:
<221> NAME/KEY: misc_feature
<222> LOCATION: (59)..(59)
<223> OTHER INFORMATION: n is a, c, g, or t

<400> SEQUENCE: 37
gggattgccc tagtaacggc gagtgaagcg gcaatagctc aaatttgaaa gctggcctnc    60
tggtccgcat tgtaatttgt agaggatgct tttaggcagc cgccggtcta agttccttgg   120
aacaggacgt catagagggt gagaatcccg tatgtgaccg gctcaggcac cttctgtaaa   180
gctccttcga cgagtcgagt tgtttgggaa tgcagctcta aatgggaggt aaatttcttc   240
taaagctaaa taccggcgag agaccgatag cgcacaagta gagtgatcga aagatgaaaa   300
gcactttgga aagagagtta aaaagcacgt gaaattgttg aagggaagc gcttgcaatc     360 agacttggac ttggctgttc aaccggtctt ctgaccggcc cactcagtct tgtccaggcc    420
agcatcagtt tcggcggccg gataaaggcc ccgggaatgt agctgcctct tcggggcag    480 tgttatagcc cggggtgtaa tacggccagc cgggactgag gtccgcgctt cggctaggat   540
gc                                                                   542
```

<210> SEQ ID NO 38
<211> LENGTH: 542
<212> TYPE: DNA
<213> ORGANISM: Epicoccum nigrum

<400> SEQUENCE: 38

```
cagggattgc cctagtaacg gcgagtgaag cggcaacagc tcaaatttga aatctggcgt      60
cttggcgtc cgagttgtaa tttgcagagg gcgctttggc attggcagcg gtccaagttc      120
cttggaacag gacgtcacag agggtgagaa tcccgtacgt ggtcgctagc ctttaccgtg     180
taaagcccct tcgacgagtc gagttgtttg ggaatgcagc tctaaatggg aggtaaattt     240
cttctaaagc taaatactgg ccagagaccg atagcgcaca agtagagtga tcgaaagatg     300
aaaagcactt tggaaagaga gttaaaaagc acgtgaaatt gttgaaaggg aagcgcttgc     360
agccagactt gcctgtagtt gctcatccgg gtttctaccc ggtgcactct tctacgggca     420
ggccagcatc agtttgggcg gttggataaa ggtctctgtc atgtacctcc cttcggggag     480
atcttatagg ggagacgaca tgcaaccagc ctggactgag gtccgcgcat ctgctaggat     540
gc                                                                    542
```

<210> SEQ ID NO 39
<211> LENGTH: 526
<212> TYPE: DNA
<213> ORGANISM: Acremonium strictum

<400> SEQUENCE: 39

```
cctcagtaac ggcgagtgaa gcggcaacag ctcaaatttg aaatctggcc gcaaggtccg      60
agttgtaatt tgtagaggat gcttttggcg aggtgccttc cgagttccct ggaacgggac     120
gccatagagg gtgagagccc cgtacggtag gaccaccaag cctctgtaaa gctccttcga     180
cgagtcgagt agtttgggaa tgctgctcta aatgggaggt gtacgtcttc taaagctaaa     240
taccggccag agaccgatag cgcacaagta gagtgatcga agatgaaaa gcactttgaa     300
aagagggtta aaaagtacgt gaaattgttg aaagggaagc attcatgacc agacttgggc     360
ttggttgaac atccggcgtt ctcgccggtg cactctgcca gtccaggcca gcatcagttt     420
gccccggggg ataaaggcgg cgggaatgtg ctccccttcg gggagtgtta tagcccgtcg     480
tgtaatgccc tggggcggac tgaggaacgc gcttcggcac ggatgc                   526
```

<210> SEQ ID NO 40
<211> LENGTH: 515
<212> TYPE: DNA
<213> ORGANISM: Geotrichum candidum

<400> SEQUENCE: 40

```
agggattgcc ttagtaacgg cgagtgaagc ggcaaaagct caaatttgaa atcggccccc      60
aggtcgagtt gtaatttgta gattgtatct tgagagcgga ttaaagtctg ttggaacaca     120
gcgccttaga gggtgacagc cccgtaaaat ctattctcat tgtaagatac tttcgaagag     180
tcgagttgtt tgggaatgca gctctaagtg ggaggtaaat tccttctaaa gctaaatatt     240
gacgagagac cgatagcgaa caagtactgt gaaggaaaga tgaaaagcac tttgaaagag     300
gagtgaaaaa gtacgtgaaa ttgttaaaag gaagggtat tgaatcagac ttggtgctgt     360
tgttcaactg tgtctcggca cagtgtactc agcagtacta ggccaaggtg gggtgtttgg     420
gagtgaaaaa gaagttggaa cgtaactctt cggagtgtta tagcctactt tcatagctcc     480
tcaggcgcct caggactgcg cttcggcaag gacct                               515
```

<210> SEQ ID NO 41
<211> LENGTH: 528
<212> TYPE: DNA
<213> ORGANISM: Stachybotrys chartarum

<400> SEQUENCE: 41

```
agggattgcc ttagtaacgg cgagtgaagc ggcaacagct caaatttgaa atctggcccc      60
aggcccgagt tgtaatttgc agaggatgct tttggcgcgg tgccttccga gttccctgga     120
acgggacgcc atagagggtg agagccccgt ctggttggat accaagcctt tgtaaagctc     180
cttcgacgag tcgagtagtt tgggaatgct gctctaaatg gaggtatat gtcttctaaa      240
gctaaatacc ggccagagac cgatagcgca caagtagagt gatcgaaaga tgaaaagcac     300
tttggaaaga gagttaaaca gcacgtgaaa ttgttaaaag gaagcgtttt atgaccagac     360
ttgggccggt taatcatcca gcgttctcgc tggtgcactt gccggtcca ggccagcatc      420
agttcgctgc gggggataaa ggcgtcggga atgtggctcc tctggagtgt tatagccctt     480
cgcgcaatac cctgcggtgg actgaggttc gcgcatctgc aaggatgc                  528
```

<210> SEQ ID NO 42
<211> LENGTH: 539
<212> TYPE: DNA
<213> ORGANISM: Aspergillus fumigatus

<400> SEQUENCE: 42

```
gggattgcct cagtaacggc gagtgaagcg gcaagagctc aaatttgaaa gctggcccct      60
tcggggtccg cgttgtaatt tgcagaggat gcttcgggtg cagcccccgt ctaagtgccc     120
tggaacgggc cgtcatagag ggtgagaatc ccgtctggga cggggtgtct gcgtccgtgt     180
gaagctcctt cgacgagtcg agttgtttgg gaatgcagct ctaaatgggt ggtaaatttc     240
atctaaagct aaatactggc cggagaccga tagcgcacaa gtagagtgat cgaaagatga     300
aaagcacttt gaaaagagag ttaaacagca cgtgaaattg ttgaaaggga agcgtttgcg     360
accagactcg cccgcggggt tcagccggca ttcgtgccgg tgtacttccc cgtgggcggg     420
ccagcgtcgg tttgggcggc cggtcaaagg ccctcggaat gtatcacctc tcggggtgtc     480
ttatagccga gggtgcaatg cggcctgcct ggaccgagga acgcgttcgg ctcggacgc     539
```

<210> SEQ ID NO 43
<211> LENGTH: 1078
<212> TYPE: DNA
<213> ORGANISM: Penicillium purporogenum
<220> FEATURE:
<221> NAME/KEY: misc_feature
<222> LOCATION: (65)..(65)
<223> OTHER INFORMATION: n is a, c, g, or t
<220> FEATURE:
<221> NAME/KEY: misc_feature
<222> LOCATION: (73)..(73)
<223> OTHER INFORMATION: n is a, c, g, or t
<220> FEATURE:
<221> NAME/KEY: misc_feature
<222> LOCATION: (100)..(101)
<223> OTHER INFORMATION: n is a, c, g, or t
<220> FEATURE:
<221> NAME/KEY: misc_feature
<222> LOCATION: (103)..(103)
<223> OTHER INFORMATION: n is a, c, g, or t
<220> FEATURE:
<221> NAME/KEY: misc_feature
<222> LOCATION: (135)..(135)
<223> OTHER INFORMATION: n is a, c, g, or t
<220> FEATURE:
<221> NAME/KEY: misc_feature
<222> LOCATION: (157)..(157)
<223> OTHER INFORMATION: n is a, c, g, or t
<220> FEATURE:
<221> NAME/KEY: misc_feature
<222> LOCATION: (228)..(228)
<223> OTHER INFORMATION: n is a, c, g, or t
<220> FEATURE:
<221> NAME/KEY: misc_feature
<222> LOCATION: (441)..(441)
<223> OTHER INFORMATION: n is a, c, g, or t
<220> FEATURE:
<221> NAME/KEY: misc_feature
<222> LOCATION: (443)..(444)
<223> OTHER INFORMATION: n is a, c, g, or t
<220> FEATURE:
<221> NAME/KEY: misc_feature
<222> LOCATION: (446)..(450)
<223> OTHER INFORMATION: n is a, c, g, or t
<220> FEATURE:
<221> NAME/KEY: misc_feature
<222> LOCATION: (479)..(479)
<223> OTHER INFORMATION: n is a, c, g, or t
<220> FEATURE:
<221> NAME/KEY: misc_feature
<222> LOCATION: (484)..(484)
<223> OTHER INFORMATION: n is a, c, g, or t
<220> FEATURE:
<221> NAME/KEY: misc_feature
<222> LOCATION: (546)..(546)
<223> OTHER INFORMATION: n is a, c, g, or t

<400> SEQUENCE: 43

```
ggaagtaaaa gtcgtaacaa ggtttccgta ggtgaacctg cggaaggatc attaccgagt      60
gcggngccct cgntggccca acctcccacc cttgtctctn nantacacct gttgctttgg     120
cgggcccacc ggggnccacc tggtcgccgg gggacantct gtccccgggc ccgcgcccgc     180
cgaagcgctc tgtgaaccct gatgaagatg ggctgtctga gtactatnga aaattgtcaa     240
aactttcaac aatggatctc ttggttccgg catcgatgaa gaacgcagcg aaatgcgata     300
agtaatgtga attgcagaat tccgtgaatc atcgaatctt tgaacgcaca ttgcgccccc     360
tggcattccg gggggcatgc ctgtccgagc gtcatttctg ccctcaagca cggcttgtgt     420
gttgggtgcg gtcccccccgg ngnngnnnnn acctgcccga aaggcagcgg cgacgtccng     480
tctnggtcct cgagcgtatg gggctttgtc actcgctcgg gaaggactgg cggggggttgg     540
tcaccnacca aaattttacc acggttgacc tcggatcagg taggagttac ccgctgaact     600
taagcatatc aataagcgga ggaaaagaaa ccaaccggga ttgcctcagt aacgcgagt      660
gaagcggcaa gagctcaaat ttgaaatctg gcccctcgg ggtccgagtt gtaatttgca     720
gaggatgctt cgggtgcggt ccccatctaa gtgccctgga acgggccgtc atagagggtg     780
agaatcccgt ctgggatggg cggccgcgcc cgtgtgaagc tccttcgacg agtcgagttg     840
tttgggaatg cagctctaag cgggtggtaa atttcatcta aagctaaata ctggccggag     900
accgatagcg cacaagtaga gtgatcgaaa gatgaaaagc actttgaaaa gagagttaaa     960
cagcacgtga aattgttgaa agggaagcgt tgtccaccag actcgcccgg ggggttcag    1020
ccggcacgtg tgccggtgta ctcctctccg ggcgggccag catcggtttg ggcggctg     1078
```

<210> SEQ ID NO 44
<211> LENGTH: 1012
<212> TYPE: DNA
<213> ORGANISM: Penicillium purporogenum

<400> SEQUENCE: 44

```
gtttattcta cgcccacgtt cactaagcaa caaggggctt cttacatatt taaagtttga      60
```

```
gaataggtta aggttgtttc aaccccaagg cctctaatca ttcgctttac ctcataaaac     120
tgatgtcgtt actgctatcc tgagggaaac ttcggcagga accagctacc agatggttcg     180
attagtctttt cgcccctata cccaaatttg acgatcgatt tgcacgtcag aaccgctgcg     240
agcctccacc agagtttcct ctggcttcgc cctattcagg catagttcac catctttcgg     300
gtcccaacag ctatgctctt actcaaatcc atccgaagac atcaggatcg gtcgatggtg     360
cgccccgagg ggctcccacc tccgttcgct ttcactgcgc ggacgggttt gacacccgaa     420
cactcgcata gatgttagac tccttggtcc gtgtttcaag acgggccgtt gaccaccatt     480
acgccagcat cctcgccgaa gcgcgggcct cggtccaggc tggctgtatg caccccggg      540
ctataagaca ccccggaggg tggtacattc ccggggcctt tcaccagccg cccaaaccga     600
tgctggcccg cccggagagg agtacaccgg cacacgtgcc ggctgaaccc ccccgggcga     660
gtctggtgga caacgcttcc cttttcaacaa tttcacgtgc tgtttaactc tcttttcaaa     720
gtgcttttca tctttcgatc actctacttg tgcgctatcg gtctccggcc agtatttagc     780
tttagatgaa atttaccacc cgcttagagc tgcattccca aacaactcga ctcgtcgaag     840
gagcttcaca cgggcgcggc cgcccatccc agacgggatt ctcaccctct atgacggccc     900
gttccagggc acttagatgg ggaccgcacc cgaagcatcc tctgcaaatt acaactcgga     960
ccccgagggg gccagatttc aaatttgagc tcttgccgct tcactcgccg tt            1012
```

<210> SEQ ID NO 45
<211> LENGTH: 980
<212> TYPE: DNA
<213> ORGANISM: Fusarium oxysporum

<400> SEQUENCE: 45

```
tccgtaggtg aacctgcgga gggatcatta ccgagtttac aactcccaaa cccctgtgaa      60
cataccactt gttgcctcgg cggatcagcc cgctcccggt aaaacgggac ggcccgccag     120
aggaccccta aactctgttt ctatatgtaa cttctgagta aaaccataaa taatcaaaa      180
cttttcaacaa cggatctctt ggttctggca tcgatgaaga acgcagcaaa atgcgataag     240
taatgtgaat tgcagaattc agtgaatcat cgaatctttg aacgcacatt gcgccccgcca    300
gtattctggc gggcatgcct gttcgagcgt catttcaacc ctcaagcaca gcttggtgtt     360
gggactcgcg ttaattcgcg ttccccaaat tgattggcgg tcacgtcgag cttccatagc     420
gtagtagtaa aaccctcgtt actggtaatc gtcgcggcca cgccgttaaa ccccaacttc     480
tgaatgttga cctcggatca ggtaggaata cccgctgaac ttaagcatat caataagcgg     540
aggaaaagaa accaacaggg attgccctag taacggcgag tgaagcggca acagctcaaa     600
tttgaaatct ggctctcggg cccgagttgt aatttgtaga ggatacttttt gatgcggtgc     660
cttccgagtt ccctggaacg ggacgccata gagggtgaga gccccgtctg gttggatgcc     720
aaatctctgt aaagttcctt caacgagtcg agtagtttgg gaatgctgct ctaaatggga     780
ggtatatgtc ttctaaagct aaataccggc cagagaccga tagcgcacaa gtagagtgat     840
cgaaagatga aaagcacttt gaaaagagag ttaaaaagta cgtgaaattg ttgaaaggga     900
agcgtttatg accagacttg ggcttggtta atcatctggg gttctcccca gtgcactttt     960
ccagtccagg ccagcatcag                                                  980
```

<210> SEQ ID NO 46
<211> LENGTH: 752
<212> TYPE: DNA
<213> ORGANISM: Fusarium oxysporum

<400> SEQUENCE: 46

```
gctcacgttc aattaagcaa caagagcttc ttacatattt aaagtttgag aatggatgaa      60
ggctaaatag cgccccccgag tccctaatca ttcgctttac ctcataaaac tgagttcaac    120
actgctatcc tgagggaaac ttcggcggaa accagctact agaaggttcg attagtcttt    180
cgccccccatg cccatatttg acgatcgatt tgcacgtcag aaccgctgcg agcctccacc    240
agagtttcct ctggcttcac cctatacagg catagttcac cttctttcgg gtccggcccc    300
gtatgctctt actcaaatcc atccgagaac atcaggatcg tcgatgatg cgccgaagct     360
ctcacctgcg ttcactttca ttacgcgtag gggtttgaca cccgaacact cgcatacgaa    420
gacgactcct tggtccgtgt ttcaagacgg gtcgttgatg accattacgc cagcatcctt    480
gcagatgcgc gaacctcagt ccccccccagg gtattacacg gtgggctata acactccccg   540
aagagagcca cattcccgcc gcctttatcc cccggggaaa actgatgctg gcctggactg    600
gaaaagtgca ctggggagaa ccccagatga ttaaccaagc ccaagtctgg tcataaacgc    660
ttcccttttca acaatttcac gtactttttta actctctttt caaagtgctt ttcatctttc   720
gatcactcta cttgtgcgct atcggtctct gg                                   752
```

<210> SEQ ID NO 47
<211> LENGTH: 981
<212> TYPE: DNA
<213> ORGANISM: Cladosporium cladosporioides

<400> SEQUENCE: 47

```
gcggaggaca ttacagaacg cccgggcttc ggcctggtta ttcataaccc tttgttgtcc      60
gactctgttg cctccggggc gaccctgcct tcgggcgggg gctccgggtg gacacttcaa    120
actcttgcgt aactttgcag tctgagtaaa cttaattaat aaattaaaac ttttaacaac    180
ggatctcttg gttctggcat cgatgaagaa cgcagcgaaa tgcgataagt aatgtgaatt    240
gcagaattca gtgaatcatc gaatctttga acgcacattg cgccccctgg tattccgggg    300
ggcatgcctg ttcgagcgtc atttcaccac tcaagcctcg cttggtattg gcaacgcgg    360
tccgccgcgt gcctcaaatc gtccggctgg gtcttctgtc ccctaagcgt tgtggaaact    420
attcgctaaa gggtgttcgg gaggctacgc cgtaaaacaa ccccatttct aaggttgacc    480
tcggatcagg tagggatacc cgctgaactt aagcatatca ataagcggag gaaaagaaac    540
caacagggat tgctctagta acggcgagtg aagcagcaat agctcaaatt tgaaatctgg    600
cgtcttcgac gtccgagttg taatttgtag gatgcttc tgagtggcca ccgacctaag     660
ttccttggaa caggacgtca tagagggtga gaatcccgta tgcggtcgga aaggcgctct    720
atacgtagct ccttcgacga gtcgagttgt ttgggaatgc agctctaaat gggaggtaaa    780
tttcttctaa agctaaatat tggccagaga ccgatagcgc acaagtagag tgatcgaaag    840
atgaaaagca ctttggaaag agagttaaaa agcacgtgaa attgttaaaa gggaagggat    900
tgcaaccaga cttgctcgcg gtgttccgcc ggtcttctga ccggtctact cgccgcgttg   960
caggccagca tcgtctggtg c                                               981
```

<210> SEQ ID NO 48
<211> LENGTH: 1017
<212> TYPE: DNA
<213> ORGANISM: Cladosporium cladosporioides

<400> SEQUENCE: 48

| | |
|---|---|
| tgtccacgtt caactaagta acaaggactt cttacatatt taaagtttga aataggtta | 60 |
| aggttgtttc aaccccaagg cctctaatca ttcgctttac ctcataaaac tgaaaacgtt | 120 |
| actgctatcc tgagggaaac ttcggcagga accagctact agatggttcg attagtcttt | 180 |
| cgcccctata cccaaatttg acgatcgatt tgcacgtcag aaccgctgcg agcctccacc | 240 |
| agagtttcct ctggcttcac cctattcagg catagttcac catctttcgg gtcccaacag | 300 |
| ctatgctctt actcaaatcc atccgaagac atcaggatcg gtcgatgatg cacctttgcgg | 360 |
| ttctcacctc cgttcacttt cattacgcgt aggggtttga cacccgaaca ctcgcataga | 420 |
| tgttagactc cttggtccgt gtttcaagac gggcggatta cgaccattac gccagcatcc | 480 |
| tagccgaagc gcggacctcg cccggcgctc gctgcatcac aagaggctat aacactcccg | 540 |
| agggagctac attcctcaag tcttatccag cggcaccaga cgatgctggc ctgcaacgcg | 600 |
| gcgagtagac cggtcagaag accggcggaa caccgcgagc aagtctggtt gcaatcccct | 660 |
| cccttttaac aatttcacgt gcttttttaac tctctttcca aagtgctttt catctttcga | 720 |
| tcactctact tgtgcgctat cggtctctgg ccaatatta gctttagaag aaatttacct | 780 |
| cccatttaga gctgcattcc caaacaactc gactcgtcga aggagctacg tatagagcgc | 840 |
| cttttccgacc gcatacggga ttctcaccct ctatgacgtc ctgttccaag aacttaggt | 900 |
| cggtggccac tcagaagcat cctctacaaa ttacaactcg gacgtcgaag acgccagatt | 960 |
| tcaaatttga gctattgctg cttcactcgc cgttactaga gcaatccctg ttggttt | 1017 |

<210> SEQ ID NO 49
<211> LENGTH: 1018
<212> TYPE: DNA
<213> ORGANISM: Aspergillus restrictus
<220> FEATURE:
<221> NAME/KEY: misc_feature
<222> LOCATION: (420)..(420)
<223> OTHER INFORMATION: n is a, c, g, or t
<220> FEATURE:
<221> NAME/KEY: misc_feature
<222> LOCATION: (524)..(525)
<223> OTHER INFORMATION: n is a, c, g, or t

<400> SEQUENCE: 49

| | |
|---|---|
| cttccgttag ggtaacctgc ggaaggatca ttaccgagtg cgggccctct gggtccaacc | 60 |
| tcccatccgt gtctcttgta ccctgttgct tcggcgggcc cgccttcatg gccgccgggg | 120 |
| ggctctcttg cccccgggcc cgcgcccgcc ggagactcca acattgaaca ctgtctgaag | 180 |
| tttgcagtct gagttttcat ataagaaaaa tcgttaaaac tttcaacaac ggatctcttg | 240 |
| gttccggcat cgatgaagaa cgcagcgaaa tgcgatacgt aatgtgaatt gcagaattca | 300 |
| gtgaatcatc gagtctttga acgcacattg cgccctctgg tattccgggg gcatgcctg | 360 |
| tccgagcgtc attgctgccc tcaagcacgg cttgtgtgtt gggccccgt cccggttctn | 420 |
| ccagccggga cgggcccgaa aggcagcggc ggcaccgtgt ccggtcctcg agtgtatggg | 480 |
| gctctgtcac ccactcgtgt aggcccggcc ggcggccagc ctcnnaaccc aattattttt | 540 |
| aaccaggttg acctcggatc aggtagggat acccgctgaa cttaagcata tcaataagcg | 600 |
| gaggaaaaga aaccaaccgg gattgcctca gtaacggcga gtgaagcggc aaaagctcaa | 660 |
| atttgaaatc tggcccctcc ggggtccgag ttgtaatttg tagaggatgc ttcgggtgcg | 720 |
| gccccgtct aagtgctctg gaatgggcca tcagagaggg tgaaaatccc gtctgggacg | 780 |
| gggtgtccgc gtccgtgtga agctccttcg acgagtcgaa ttgtttggga atgcagctct | 840 |
| aaatgggtgg taaatttcat ctaaagctaa atattggccg agaccgata gcgcacaagt | 900 |

```
agagtgatcg aaagatgaaa agcactttga aaagagagtt aaaaagcacg tgaaattgtt      960
gaaagggaag cacttgcgac cagactcgcc cacggggttc agccggcttt cgggccgg      1018
```

<210> SEQ ID NO 50
<211> LENGTH: 1037
<212> TYPE: DNA
<213> ORGANISM: Aspergillus restrictus

<400> SEQUENCE: 50

```
ttctatgcca cgttcattaa gaaacaaggg cttcttacat atttaaagtt tgagaatagg       60
ttaaggttgt ttcaaccccca aggcctctaa tcattcgctt tacctcataa aactgatttc      120
gcgttactgc tatcctgagg gaaacttcgg caggaaccag ctaccagatg gttcgattag      180
tctttcgccc ctatacccaa atttgacgat cgatttgcac gtcagaaccg ctgcgagcct      240
ccaccagagt ttcctctggc ttcaccctat tcaggcatag ttcaccatct ttcgggtccc      300
cacagctacg ctcatactca aatccatccg aagacatcag gatcggtcga tggtgcgccc      360 ctcaagggc tcccacctcc gttcgctttc actgcgcgta cgggtttgcc acccgaacac      420
tcgcgtagat gttagactcc ttggtccgtg tttcaagacg ggtcatttac gaccattatg      480
ccagcgtccg tgccgaagcg cgttcctcgg tctgggctgg ccgcatggca ccctggcta      540 taagacaccc cgagaggtgt tacattccag gggcctttaa ccggccgccc aaaccgacgc      600
tggcccgccc ccggggaagt acaccggccc gaaagccggc tgaaccccgt gggcgagtct      660
ggtcgcaagt gcttcccttt caacaatttc acgtgctttt taactctctt ttcaaagtgc      720
ttttcatctt tcgatcactc tacttgtgcg ctatcggtct ccggccaata tttagcttta      780
gatgaaattt accacccatt tagagctgca ttcccaaaca actcgactcg tcgaaggagc      840
ttcacacgga cgcggacacc ccgtcccaga cgggattttc accctctctg atggcccatt      900
ccagagcact tagacggggg ccgcacccga agcatcctct acaaattaca actcggaccc      960
cggaggggcc agatttcaaa tttgagcttt tgccgcttca ctcgccgtta ctgaggcaat      1020
cccggttggt ttcttttt                                                    1037
```

<210> SEQ ID NO 51
<211> LENGTH: 1031
<212> TYPE: DNA
<213> ORGANISM: Rhizopus oryzae
<220> FEATURE:
<221> NAME/KEY: misc_feature
<222> LOCATION: (28)..(28)
<223> OTHER INFORMATION: n is a, c, g, or t

<400> SEQUENCE: 51

```
ctgcggaagg atcattaatt atgttaangc gccttacctt agggtttcct ctggggtaag       60
tgattgcttc tacactgtga aaatttggct gagagactca gactggtcat gggtagacct      120
atctggggtt tgatcgatgc cactcctggt ttcaggagta cccttcataa taaacctaga      180
aattcagtat tataaagttt aataaaaaac aacttttaac aatggatctc ttggttctcg      240
catcgatgaa gaacgtagca aagtgcgata actagtgtga attgcatatt cagtgaatca      300
tcgagtcttt gaacgcagct tgcactctat ggttttcta tagagtacgc ctgcttcagt      360
atcatcacaa acccacacat aacatttgtt tatgtggtga tgggtcgcat cgctgtttta      420
ttacagtgag cacctaaaat gtgtgtgatt ttctgtctgg cttgctaggc aggaatatta      480
cgctggtctc aggatctttt tttttggttc gcccaggaag taaagtacaa gagtataatc      540
```

```
cagtaacttt caaactatga tctgaagtca ggtgggatta cccgctgaac ttaagcatat    600
caataagcgg aggaaaagaa ataacaatg atttccctag taacggcgag tgaagaggaa     660
agagctcaaa gttggaacct gtttggccta gctaaaccgg attgtagact gtagaagtgt    720
tttccaggca agccgagtaa ataagtcctt tggaacaggg catcatagag ggtgagaatc    780
ccgtctttgg cttgagcatt tgccttttgt gatacgcttt caaagagtca ggttgtttgg    840
gaatgcagcc taaattgggt ggtaaatctc acctaaagct aaatattggc gagaaaccga    900
tagcgaacaa gtaccgtgag ggaaagatga aaagaacttt gaaagagag ttaaacagta    960 tgtgaaattg ttaaaaggga accgtttgga gccagactgg cttgtctgta atcaatctag   1020
gcttcggcct g                                                         1031

<210> SEQ ID NO 52
<211> LENGTH: 1012
<212> TYPE: DNA
<213> ORGANISM: Rhizopus oryzae

<400> SEQUENCE: 52
gcttcatgac ctgcttcaat taagcaaaca gggtcgtctt acatatttaa agtttgagag     60
tggttgaagg gcgtttagcc ccccgagacc ccaatcattc gctttaccac ataaaactgc    120
gtataagttt ctgctatcct gagggaaact tcggcaggaa ccagctacta gatggttcga    180
ttagtctttc gcccctatac ccaaatttga cgatcgattt gcacgtcaga atcgctacga    240
gcctccacca gagtttcctc tggcttcacc ctattcaggc atagttcacc atctttcggg    300
tcccatcatt agtgctttgt ctcggtcaat tcagtataaa acgtcagcgc cggacgatac    360
tgcctcctta atggattcgt atcaatcagt ttccttacgc atatgggttt ggcacccaaa    420
tactcgcact aatggtggac tccttggtcc gtgtttcaag acgggtcatt tagagtcatt    480
aagccaacaa cctaagcgaa tagaagtata accaaaaaga tcaaccttga taccgtagta    540
cctcagaaaa cctcctggaa aaactcgcca ataagcattc gctgcgttcc tcaatccaac    600
ccaaggtatt ttctaaggga ctataacacc cacaagtggg ccacatttcc cctagttttt    660
tccctcaagt caaattgtcg ttggcaggca tagcctgcaa gtgcatccag gccgaagcct    720
agattgatta cagacaagcc agtctggctc caaacggttc cctttttaaca atttcacata    780 ctgtttaact ctcttttcaa agttcttttc atctttccct cacggtactt gttcgctatc    840
ggtttctcgc caatatttag ctttaggtga gatttaccac ccaatttagg ctgcattccc    900
aaacaacctg actctttgaa agcgtatcac aaaaggcaaa tgctcaagcc aaagacggga    960
ttctcaccct ctatgatgcc ctgttccaaa ggacttattt actcggcttg cc            1012

<210> SEQ ID NO 53
<211> LENGTH: 1033
<212> TYPE: DNA
<213> ORGANISM: Penicillium brevicompactum

<400> SEQUENCE: 53
tccgtagggt gaacctgcgg aaggatcatt accgagtgag ggccctctgg gtccaacctc     60
ccacccgtgt ttattttacc ttgttgcttc ggcgagcctg ccttttggct gccggggac    120 gtctgtcccc gggtccgcgc tcgccgaaga caccttagaa ctctgtctga agattgtagt    180
ctgagattaa atataaatta tttaaaactt tcaacaacgg atctcttggt tccggcatcg    240
atgaagaacg cagcgaaatg cgatacgtaa tgtgaattgc agaattcagt gaatcatcga    300
gtctttgaac gcacattgcg cccctctggta ttccggaggg catgcctgtc cgagcgtcat    360
```

```
tgctgccctc aagcacggct tgtgtgttgg gctccgtcct ccttccgggg gacgggcccg      420
aaaggcagcg gcggcaccgc gtccggtcct caagcgtatg gggctttgtc acccgctttg      480
taggactggc cggcgcctgc cgatcaacca aacttttttc caggttgacc tcggatcagg      540
tagggatacc cgctgaactt aagcatatca ataagcggag gaaaagaaac caacagggat      600
tgccccagta acggcgagtg aagcggcaag agctcaaatt tgaaagctgg ctccttcggg      660
gtccgcattg taatttgcag aggatgcttc gggagcggtc ccatctaag tgccctggaa       720 cgggacgtca tagagggtga gaatcccgta tgggatgggg tgtccgcgcc cgtgtgaagc      780
tccttcgacg agtcgagttg tttgggaatg cagctctaaa tgggtggtaa atttcatcta      840
aagctaaata ttggccggag accgatagcg cacaagtaga gtgatcgaaa gatgaaaagc      900
actttgaaaa gagagttaaa aagcacgtga aattgttgaa agggaagcgc ttgcgaccag      960
actcgctcgc ggggttcagc cggcattcgt gccggtgtac ttccccgcga gcgggccagc     1020
gtcggtttgg gcg                                                        1033
```

<210> SEQ ID NO 54
<211> LENGTH: 1019
<212> TYPE: DNA
<213> ORGANISM: Penicillium brevicompactum
<220> FEATURE:
<221> NAME/KEY: misc_feature
<222> LOCATION: (5)..(5)
<223> OTHER INFORMATION: n is a, c, g, or t

<400> SEQUENCE: 54

```
gacantctat gccacggttc aattaagcaa caagggcttc ttacatattt aaagtttgag       60
aataggttaa ggttgtttca accccaaggc ctctaatcat tcgctttacc tcataaaact      120
gaattcgcgt tactgctatc ctgagggaaa cttcggcagg aaccagctac cagatggttc      180
gattagtctt tcgcccctat acccaaattc gacgatcgat ttgcacgtca gaaccgctac      240
gagcctccac cagagttttcc tctggcttcg ccctattcag gcatagttca ccatctttcg      300
ggtcccaaca gctacgctct tactcaaatc catccgaaga cttcaggatc ggtcgatggt      360
gcacccttgc gggttcccac ctccgttcgc tttcacttcg cgcacgggtt tgacacccga      420
acactcgcgt agatgttaga ctccttggtc cgtgtttcaa gacgggtcgc ttacgaccat      480
tatgccagcg tccgagccga agcgcgttcc tcggtccggg caggccgcat tgcaccctg       540 gctataagac gccccgagg gggcgttacc ttccagaggc ctttgaccga ccgcccaaac       600
cgacgctggc ccgctcgcgg ggaagtacac cggcacgaat gccggctgaa ccccgcgagc      660
gagtctggtc gcaagcgctt ccctttcaac aatttcacgt gcttttaac tctcttttca      720 aagtgctttt catctttcga tcactctact tgtgcgctat cggtctccgg ccaatattta      780
gctttagatg aaatttacca cccatttaga gctgcattcc caaacaactc gactcgtcga      840
aggagcttca cacgggcgcg gacacccat cccatacggg attctcaccc tctatgacgt       900
cccgttccag ggcacttaga tggggaccgc tcccgaagca tcctctgcaa attacaatgc      960
ggaccccgaa ggagccagct ttcaaatttg agctcttgcc gcttcactcg ccgttactg     1019
```

<210> SEQ ID NO 55
<211> LENGTH: 1035
<212> TYPE: DNA
<213> ORGANISM: Ulocladium chartarum
<220> FEATURE:
<221> NAME/KEY: misc_feature
<222> LOCATION: (158)..(158)

<223> OTHER INFORMATION: n is a, c, g, or t

<400> SEQUENCE: 55

| | | | | | |
|---|---|---|---|---|---|
| tccgtaggtg | aacctgcgga | gggatcatta | cacaatatga | aagcgggctg | gaatcctttg | 60 |
| gggttacagc | cttgctgaat | tattcacccg | tgtcttttgc | gtacttcttg | tttccttggt | 120 |
| gggttcgccc | accataggac | aaaccattaa | acctttthgt | aattgcaatc | agcgtcagta | 180 |
| aaaaaaatta | ataattacaa | cttttaacaa | cggatctctt | ggttctggca | tcgatgaaga | 240 |
| acgcagcgaa | atgcgataag | tagtgtgaat | tgcagaattc | agtgaatcat | cgaatctttg | 300 |
| aacgcacatt | gcgcccttg | gtattccaaa | gggcatgcct | gttcgagcgt | catttgtacc | 360 |
| ctcaagcttt | gcttggtgtt | gggcgtcttg | tctccagttc | gctggagact | cgccttaaag | 420 |
| taattggcag | ccggcctact | ggtttcggag | cgcagcacaa | gtcgcgctct | cttccagcga | 480 |
| aggtcagcat | ccacaaagcc | ttttttcaac | ttttgaccctc | ggatcaggta | gggatacccg | 540 |
| ctgaacttaa | gcatatcaat | aagcggagga | aaagaaacca | acagggattg | ccctagtaac | 600 |
| ggcgagtgaa | gcggcaacag | ctcaaatttg | aaatctggct | cttttagagt | ccgagttgta | 660 |
| atttgcagag | ggcgctttgg | ctttggcagc | ggtccaagtt | ccttggaaca | ggacgtcaca | 720 |
| gagggtgaga | atcccgtacg | tggtcgctgg | ctattgccgt | gtaaagcccc | ttcgacgagt | 780 |
| cgagttgttt | gggaatgcag | ctctaaatgg | gaggtacatt | tcttctaaag | ctaaatattg | 840 |
| gccagagacc | gatagcgcac | aagtagagtg | atcgaaagat | gaaaagcact | ttggaaagag | 900 |
| agtcaaacag | cacgtgaaat | tgttaaaagg | gaagcgcttg | cagccagact | tgcttacagt | 960 |
| tgctcatccg | ggcttttgcc | cggtgcactc | ttctgtaggc | aggccagcat | cagtttgggc | 1020 |
| ggtaggataa | aggtc | | | | | 1035 |

<210> SEQ ID NO 56
<211> LENGTH: 1001
<212> TYPE: DNA
<213> ORGANISM: Ulocladium chartarum

<400> SEQUENCE: 56

| | | | | | |
|---|---|---|---|---|---|
| ttcactgtca | cgttcattaa | gtaacaagga | cttcttacat | atttaaagtt | tgagaatagg | 60 |
| tgaaggttgt | ttcaaccccc | aggcctctaa | tcattcgctt | tacctcataa | aactgaatac | 120 |
| gttactgcta | tcctgaggga | aacttcggca | ggaaccagct | actagatagt | tcgattagtc | 180 |
| tttcgcccct | atgcccaaat | tgacgatcg | atttgcacgt | cagaaccgct | gcgagcctcc | 240 |
| accagagttt | cctctggctt | caccctattc | aagcatagtt | caccatcttt | cgggtcccaa | 300 |
| cagccatgct | cttactcaaa | tccttccgaa | gacatcagga | tcggtcgatg | gtgcacccett | 360 |
| gcgggttccc | acctccgttc | actttcatta | cgcgctcggg | cttgacaccc | aaacactcgc | 420 |
| atagatgtta | gactccttgg | tccgtgtttc | aagacgggcc | gcttacagcc | attacgccag | 480 |
| catcctagca | gatgcgcgga | cctcagtcca | ggctggtagt | atgtcgtctc | ccctataagg | 540 |
| cctccccgaa | aggaggtacg | tgacagagac | ctttatccta | ccgcccaaac | tgatgctggc | 600 |
| ctgcctacag | aagagtgcac | cgggcaaaag | cccggatgag | caactgtaag | caagtctggc | 660 |
| tgcaagcgct | tccctttaa | caatttcacg | tgctgtttga | ctctctttcc | aaagtgcttt | 720 |
| tcatctttcg | atcactctac | ttgtgcgcta | tcggtctctg | gccaatattt | agctttagaa | 780 |
| gaaatgtacc | tcccatttag | agctgcattc | ccaaacaact | cgactcgtcg | aaggggcttt | 840 |
| acacggcaat | agccagcgac | cacgtacggg | attctcaccc | tctgtgacgt | cctgttccaa | 900 |
| ggaacttgga | ccgctgccaa | agccaaagcg | ccctctgcaa | attacaactc | ggactctaaa | 960 |

```
agagccagat tcaaatttg agctgttgcc gcttcactcg c                    1001
```

<210> SEQ ID NO 57
<211> LENGTH: 1023
<212> TYPE: DNA
<213> ORGANISM: Trichoderma viride

<400> SEQUENCE: 57

```
tccgtagggt aacctgcgga gggatcatta ccgagtttac aactcccaaa cccaatgtga    60
accataccaa actgttgcct cggcggggtc acgccccggg tgcgtcgcag ccccggaacc   120
aggcgcccgc cggagggacc aaccaaactc tttctgtag tccctcgcg gacgttattt    180
cttacagctc tgagcaaaaa ttcaaaatga atcaaaactt caacaacgg atctcttggt    240
tctggcatcg atgaagaacg cagcgaaatg cgataagtaa tgtgaattgc agaattcagt    300
gaatcatcga atctttgaac gcacattgcg cccgccagta ttctggcggg catgcctgtc    360
cgagcgtcat ttcaaccctc gaaccctcc gggggtcgg cgttgggac ctcgggagcc     420
cctaagacgg gatcccggcc cgaaataca gtggcggtct cgccgcagcc tctcctgcgc    480
agtagtttgc acaactcgca ccgggagcgc ggcgcgtcca cgtccgtaaa acacccaact   540
tctgaaatgt tgacctcgga tcaggtagga atacccgctg aacttaagca tatcaataag   600
cggaggaaaa gaaaccaaca gggattgccc cagtaacggc gagtgaagcg gcaacagctc   660
aaatttgaaa tctggcccct agggtccgag ttgtaatttg tagaggatgc ttttggtgag   720
gtgccgcccg agttccctgg aacgggacgc gcagagggt gagagccccg tctggctggc   780
caccgagcct ctgtaaagct ccttcgacga gtcgagtagt ttgggaatgc tgctcaaaat   840
gggaggtata tgtcttctaa agctaaatat tggccagaga ccgatagcgc acaagtagag   900
tgatcgaaag atgaaaagca ccttgaaaag agggttaaac agtacgtgaa attgttgaaa   960
gggaagcgct tgtgaccaga cttgggcgcg gcggatcatc cggggttctc cccggtgcac  1020
ttc                                                                1023
```

<210> SEQ ID NO 58
<211> LENGTH: 1005
<212> TYPE: DNA
<213> ORGANISM: Trichoderma viride

<400> SEQUENCE: 58

```
aattcgaatg ccacgttcat taagcaacaa gggcttctta catatttaaa gtttgagaat    60
ggatgaaggc aatatagcgc ccccgagtcc ctaatcattc gctttacctc ataaaactga   120
gatcaacact gctatcctga gggaaacttc ggcggaaacc agctactaga aggttcgatt   180
agtctttcgc cccatgccc atatttgacg atcgatttgc acgtcagaac cgctgcgagc   240
ctccaccaga gtttcctctg gctttcaccct atacaggcat agttcacctt ctttcgggtc   300
cggccccgta tgctcttact caaatccatc cgagaacatc aggatcggtc gatgatgcgc   360
cgaagctctc acctgcgttc actttcatta cgcgtagggg tttgacaccc gaacactcgc   420
atacgaagac gactccttgg tccgtgtttc aagacgggtc gctggtgacc attacgccag   480
catccttgca gatgcgcggt cctcagtcca gcgcaggta ttatgcaacg gctataaca    540
ctcccggagg agccacgttc ccgaagcctt ttccccccgc gccgaactga tgctggcctg   600
aacacgcgca agtgcaccgg ggagaacccc ggatgatccg ccgcgcccaa gtctggtcac   660
aagcgcttcc ctttcaacaa tttcacgtac tgtttaaccc tcttttcaag gtgcttttca   720
```

-continued

```
tctttcgatc actctacttg tgcgctatcg gtctctggcc aatatttagc tttagaagac    780
atatacctcc cattttgagc agcattccca aactactcga ctcgtcgaag gagctttaca    840
gaggctcggt ggccagccag acggggctct caccctctgc ggcgtcccgt tccagggaac    900
tcgggcggca cctcaccaaa agcatcctct acaaattaca actcggaccc taggggccag    960
atttcaaatt tgagctgttg ccgcttcact cgccgttact ggggc                   1005


<210> SEQ ID NO 59
<211> LENGTH: 1063
<212> TYPE: DNA
<213> ORGANISM: Stachybotrys chartarum

<400> SEQUENCE: 59
ggaagtaaaa gtcgtaacaa ggtctccgta ggtgaacctg cggagggatc attaccgagt     60
ttacaactcc caaaccctta tgtgaaccgt acctatcgtt gcttcggcgg gaacgccccg    120
gcgccctgcg cccggatcca ggcgcccgcc ggagacccca aactcttgtg ttttttcag     180
tattctctga gtggcaaacg caaaaataaa tcaaaacttt taacaacgga tctcttggct    240
ctggcatcga tgaagaacgc agcgaaatgc gataagtaat gtgaattgca gaattcagtg    300
aatcatcgaa tctttgaacg cacattgcgc ccgttagcat tctagcgggc atgcctgtcc    360
gagcgtcatt tcaaccctca gggtccccgt tccggcgggg aacctggtgt tggggatcgg    420
cccgccccgc gcggcgccgt cccccaaatt cagtggcggt ctcgctgcag cctcccctgc    480
gtagtagtta caacctcgca tcggagctca gcgcggccac gccgtaaaac ccccgacttt    540
ctgaacgttg acctcggatc aggtaggaat acccgctgaa cttaagcata tcaataagcg    600
gaggaaaaga aaccaacagg gattgcctta gtaacggcga gtgaagcggc aacagctcaa    660
atttgaaatc tggccccagg cccgagttgt aatttgcaga ggatgctttt ggcgcggtgc    720
cttccgagtt ccctggaacg ggacgccata gagggtgaga gccccgtctg gttggatacc    780
aagcctttgt aaagctcctt cgacgagtcg agtagtttgg gaatgctgct ctaaatggga    840
ggtatatgtc ttctaaagct aaataccggc cagagaccga tagcgcacaa gtagagtgat    900
cgaaagatga aaagcacttt ggaaagagag ttaaacagca cgtgaaattg ttaaaaggga    960
agcgtttatg accagacttg gccggttaa tcatccagcg ttctcgctgg tgcactttgc    1020
cggtccaggc cagcatcagt tcgctgcggg ggataaaggc gtc                     1063


<210> SEQ ID NO 60
<211> LENGTH: 1047
<212> TYPE: DNA
<213> ORGANISM: Stachybotrys chartarum

<400> SEQUENCE: 60
ttcgaatgcc acgtttcatt aagcaacaag ggcttcttac atatttaaag tttgagaatg     60
gatgaaggct aaatagcgcc ccctggtccc taatcattcg ctttacctca taaaactgag    120
ttcaacactg ctatcctgag ggaaacttcg gcggaaacca gctactagaa ggttcgatta    180
gtctttcgcc cccatgccca tatttgacga tcgatttgca cgtcagaacc gctgcgagcc    240
tccaccagag tttcctctgg cttcacccta tacaggcata gttcaccttc tttcgggtcc    300
ggccccgtat gctcttactc aaatccatcc gagaacatca ggatcggtcg atgatgcgcc    360
gaagctctca cctgcgttca ctttcattac gcgtaggggt tttacacccg aacactcgca    420
tacgaagacg actccttggt ccgtgtttca agacgggtcg ttgatgacca ttacgccagc    480
atccttgcag atgcgcgaac ctcagtccac cgcagggtat tgcgcgaagg gctataacac    540
```

```
tccagaggag ccacattccc gacgccttta tcccccgcag cgaactgatg ctggcctgga    600
ccggcaaagt gcaccagcga gaacgctgga tgattaaccg gcccaagtct ggtcataaac    660
gcttcccttt taacaatttc acgtgctgtt taactctctt tccaaagtgc ttttcatctt    720
tcgatcactc tacttgtgcg ctatcggtct ctggccggta tttagcttta gaagacatat    780
acctcccatt tagagcagca ttcccaaact actcgactcg tcgaaggagc tttacaaagg    840
cttggtatcc aaccgacgg ggctctcacc ctctatggcg tcccgttcca gggaactcgg    900
aaggcaccgc gccaaaagca tcctctgcaa attacaactc gggcctgggg ccagatttca    960
aatttgagct gttgccgctt cactcgccgt tactaaggca atccctgttg gtttcttttc   1020
ctccgcttat tgatatgctt aagttca                                        1047

<210> SEQ ID NO 61
<211> LENGTH: 941
<212> TYPE: DNA
<213> ORGANISM: Penicillium chrysogenum

<400> SEQUENCE: 61
tgcggaagat cattaccgag tgagggccct ctgggtccaa cctcccaccc gtgtttattt     60
taccttgttg cttcggcggg cccgccttaa ctggccgccg gggggcttac gccccgggc    120 ccgcgcccgc cgaagacacc ctcgaactct gtctgaagat gtagtctga gtgaaaatat    180 aaattattta aaactttcaa caacggatct cttggttccg gcatcgatga agaacgcagc    240
gaaatgcgat acgtaatgtg aattgcaaat tcagtgaatc atcgagtctt tgaacgcaca    300
ttgcgccccc tggtattccg ggggcatgc ctgtccgagc gtcatttctg ccctcaagca    360
cggcttgtgt gttgggcccc gtcctccgat cccgggggac gggcccgaaa ggcagcggcg    420
gcaccgcgtc cggtcctcga gcgtatgggg ctttgtcacc cgctctgtag gcccggccgg    480
cgcttgccga tcaacccaaa tttttatcca ggttgacctc ggatcaggta gggatacccg    540
ctgaacttaa gcatatcaat aagcggagga aagaaacca acagggattg ccccagtaac    600
ggcgagtgaa gcggcaagag ctcaaatttg aaagctggct ccttcggggt ccgcattgta    660
atttgtagag gatgcttcgg gagcggtccc catctaagtg ccctggaacg ggacgtcata    720
gagggtgaga atcccgtatg ggatggggtg tccgcgcccg tgtgaagctc cttcgacgag    780
tcgagttgtt tgggaatgca gctctaaatg ggtggtaaat ttcatctaaa gctaaatatt    840
ggccggagac cgatagcgca caagtagagt gatcgaaaga tgaaagcac tttgaaaaga    900 gagttaaaaa gcacgtgaaa ttgttgaaag ggaagcgctt g                        941

<210> SEQ ID NO 62
<211> LENGTH: 1038
<212> TYPE: DNA
<213> ORGANISM: Penicillium chrysogenum

<400> SEQUENCE: 62
attctatgcc acgttcatta agcaacaagg gcttcttaca tatttaaagt ttgagaatag     60
gttaaggttg tttcaacccc aaggcctcta atcattcgct ttacctcata aaactgaatt    120
cgcgttactg ctatcctgag ggaaacttcg gcaggaacca gctaccagat ggttcgatta    180
gtctttcgcc cctataccca aattcgacga tcgatttgca cgtcagaacc gctacgagcc    240
tccaccagag tttcctctgg cttcgcccta ttcaggcata gttcaccatc tttcgggtcc    300
caacagctac gctcttactc aaatccatcc gaagacttca ggatcggtcg atggtgcacc    360
```

```
cgtgagggtt cccacctccg ttcgctttca cttcgcgcac gggtttgaca cccgaacact    420
cgcgtagatg ttagactcct tggtccgtgt ttcaagacgg gtcgtttacg accattatgc    480
cagcgtccga gccgaagcgc gttcctcggt ctaggcaggt cgcattgcac cctcggctat    540
aagacgcccc tagggggcgtt accttccgag ggcctttgac cgaccgctca aaccgacgct    600
ggcccgcccg cggggaagta caccggcacg aatgccggct gaaccccgcg agcgagtctg    660
gtcgcaagcg cttcccttcc aacaatttca cgtgcttttt aactctcttt tcaaagtgct    720
tttcatcttt cgatcactct acttgtgcgc tatcggtctc cggccaatat ttagctttag    780
atgaaattta ccacccattt agagctgcat tcccaaacaa ctcgactcgt cgaaggagct    840
tcacacgggc gcgacaccc catcccatac gggattctca ccctctatga cgtcccgttc    900
cagggcactt agatggggac cgctcccgaa gcatcctcta caaattacaa tgcggacccc    960
gaaggagcca gctttcaaat tgagctcttt gccgcttcac tcgccgttac tggggcaatc   1020
cctgttggtt tcttttcc                                                 1038
```

<210> SEQ ID NO 63
<211> LENGTH: 1044
<212> TYPE: DNA
<213> ORGANISM: Penicillium spinulosum

<400> SEQUENCE: 63

```
gtaacaagtt tcgtagatga acctgcggaa ggatcattac tgagtgaggg ccctctgggt     60
ccaacctccc accgtgtttt attgtacctt gttgcttcgg tgcgcccgcc tcacggccgc    120
cggggggctt ctgcccccgg gtccgcgcgc accggagaca ctattgaact ctgtctgaag    180
attgcagtct gagcataaac taaataagtt aaaactttca acaacggatc tcttggttcc    240
ggcatcgatg aagaacgcag cgaaatgcga taactaatgt gaattgcaga attcagtgaa    300
tcatcgagtc tttgaacgca cattgcgccc ctggtattc cgggggggcat gcctgtccga    360 gcgtcattgc tgccctcaag cacggcttgt gtgttgggct ccgtcccccc ggggacgggt    420
ccgaaaggca gcggcggcac cgagtccggt cctcgagcgt atgggctttt gtcacccgct    480
ctgtaggccc ggccggcgcc agccgacaac caatcatcct ttttttcaggt tgacctcgga    540 tcaggtaggg atacccgctg aacttaagca tatcaataag cggaggaaaa gaaaccaaca    600
gggattacct cagtaacggc gagtgaagcg gtaagagctc aaatttgaaa gctggctcct    660
tcggggtccg cattgtaatt tgcagaggat gtttcgggag cagccccat ctaagtgtcc    720 tggaacggac cgtcatagag ggtgagaatc ccgtatggga tggggtgtct gcgcccatgt    780
gaaactcctt cgacgagtcg agttgtttgg gaatgcagct ctaaatgggt ggtaaatttc    840
atctaaagct aaatattggc cggagaccga tagcgcacaa gtagagtgat cgaaagatga    900
aaagcacttt gaaaagagag ttaaaaagca cgtgaaattg ttgaaaggga agcgcttgcg    960
atcagactcg ccttgggggt tcagccggca ttcgtgccgg tgtacttccc ccagggcggg   1020
ccagcgtcgg tttgggtggc cggt                                         1044
```

<210> SEQ ID NO 64
<211> LENGTH: 1002
<212> TYPE: DNA
<213> ORGANISM: Penicillium spinulosum

<400> SEQUENCE: 64

```
gacattctat gcccgcgttc attaagcaac aagggcttct tacatattta agtttgaga     60 ataggttaag gttgtttcaa ccccaaggcc tctaatcatt cgctttacct cataaaactg    120
```

```
aattcgcgct actgctatcc tgagggaaac ttcggcagga accagctact agatggttcg      180
attagtcttt cgcccctata cccaaattcg acgatcgatt tgcacgtcag aaccgctgcg      240
agcctccacc agagtttcct ctggcttcgc cctattcagg catagttcac catctttcgg      300
gtcccaacag ctacgctctt actcaaatcc atccgaagac atcaggatcg gtcgatggtg      360
cacccaaagg gttcccacct ccgttcgctt tcactgcgcg cacgggtttg acacccgaac      420
actcgcgtag atgttagact ccttggtccg tgtttcaaga cgggtcgctt acgaccatta      480
tgccagcgtc cgagccgaag cgcgttcctc ggtccaggta ggccgcatgg cacccttggc      540
tataagacgc cccgagaggc gttacattcc aagggccttt gaccggccac ccaaaccgac      600
gctggcccgc cctgggggaa gtacaccggc acgaatgccg gctgaacccc caaggcgagt      660
ctgatcgcaa gcgcttccct ttcaacaatt tcacgtgctt tttaactctc ttttcaaagt      720
gcttttcatc tttcgatcac tctacttgtg cgctatcggt ctccggccaa tatttagctt      780
tagatgaaat ttaccaccca tttagagctg cattcccaaa caactcgact cgtcgaagga      840
gtttcacatg ggcgcagaca ccccatccca tacgggattc tcaccctcta tgacggtccg      900
ttccaggaca cttagatggg ggctgctccc gaaacatcct ctgcaaatta caatgcggac      960
cccgaaggag ccagctttca aatttgagct cttaccgctt ca                       1002
```

<210> SEQ ID NO 65
<211> LENGTH: 978
<212> TYPE: DNA
<213> ORGANISM: Paecilomyces variotii

<400> SEQUENCE: 65

```
ggaagtaaaa gtcgtaacaa ggtttccgta ggtgaacctg cggaaggatc attaccgagt       60
gagggtccct cggggcccaa cctcccatcc gtgttgactt gaccccctgtt gcttcggcgg     120 gcccgccgtg gttcacgccc cggccgccgg ggggttcacg ccccccgggcc cgcgcccgcc     180 gaagacccct ggaacgctgc cttgaaggtt gccgtctgag tatacaatca atgaattaaa     240
actttcaaca acggatctct tggttccggc atcgatgaag aacgcagcga atgcgataa     300 gtaatgtgaa ttgcagaatt ccgtgaatca tcgaatcttt gaacgcacat tgcgcccct     360 ggcattccgg ggggcatgcc tgtccgagcg tcattgctaa ccctccagcc cggctggtgt     420
gttgggccgc cgtccccccc ggggacggg cccgaaaggc agcggcggcg tcgcgtccgg     480
tcctcgagcg tatgggctt tgtcacgcgc ttcagtagga ccggccggct tgctggccaa     540
cgaccttcac ggtcacacct atattttctc ttaggttgac ctcggatcag gtagggatac     600
ccgctgaact taagcatatc aataagcgga ggaaagaaa ccaacaggga ttgccccagt     660
aacggcgagt gaagcggcaa gagctcaaat ttgaaatctg gcccctccgg ggtccgagtt     720
gtaatttgca gaggatgctt cgggcgcggt ccccgtctaa gtaccctgga acgggtcgtc     780
atagagggta agaatcccgt ctgggacggg tggccgtgtc cgtgtgaagc tccttcgacg     840
agtcgagttg tttgggaatg cagctctaaa tgggtggtaa atttcatcta aagctaaata     900
ttggccggag accgatagcg cacaagtaga gtgatcgaaa gatgaaaagc actttgaaaa     960
gagagttaaa cagcacgt                                                   978
```

<210> SEQ ID NO 66
<211> LENGTH: 1030
<212> TYPE: DNA
<213> ORGANISM: Paecilomyces variotii

<400> SEQUENCE: 66

```
tgcccacgtt caactaagca acaagggctt cttacatatt taaagtttga gaataggtta    60
aggttgtttc aaccccaagg cctctaatca ttcgctttac ctcataaaac tgaaaacgtt   120
actgctatcc tgagggaaac ttcggcagga accagctacc agatggttcg attagtcttt   180
cgccccctata cccaaattcg acgatcgatt tgcacgtcag aaccgctgcg agcctccacc   240
agagtttcct ctggcttcgc cctattcagg catagttcac catctttcgg gtcccaacag   300
ctacgctctt actcaaatcc atccgaagac atcaggatcg gtcgatggtg caccccgggg   360
ggttcccacc tccgttcgct ttcactgcgc ggacgggttt gacacccgaa cactcgcgta   420
gatgttagac tccttggtcc gtgtttcaag acgggccgct tacgaccatt acgccagcgt   480
ccgagccgaa gcgcgttcct cggtccaggc tggccgcatt gcacctccgg ctataagacg   540
ccccggggggg cgacacattc cggaggcctt tgaccgaccg cccaaaccga cgctggcccg   600
ccccggggg agtacaccgg tacgagtacc ggctgaaccc ccgcgggcga gtctggtcgc   660
aagcgcttcc ctttcaacaa tttcacgtgc tgtttaactc tcttttcaaa gtgcttttca   720
tctttcgatc actctacttg tgcgctatcg gtctccggcc aatatttagc tttagatgaa   780
atttaccacc catttagagc tgcattccca aacaactcga ctcgtcgaag gagcttcaca   840
cggacacggc cacccgtccc agacgggatt ctcaccctct atgacgaccc gttccagggt   900
acttagacgg ggaccgcgcc cgaagcatcc tctgcaaatt acaactcgga ccccggaggg   960
gccagatttc aaatttgagc tcttgccgct tcactcgccg ttactggggc aatccctgtt  1020
ggtttctttt                                                          1030
```

<210> SEQ ID NO 67
<211> LENGTH: 1057
<212> TYPE: DNA
<213> ORGANISM: Aspergillus versicolor
<220> FEATURE:
<221> NAME/KEY: misc_feature
<222> LOCATION: (412)..(412)
<223> OTHER INFORMATION: n is a, c, g, or t
<220> FEATURE:
<221> NAME/KEY: misc_feature
<222> LOCATION: (489)..(489)
<223> OTHER INFORMATION: n is a, c, g, or t
<220> FEATURE:
<221> NAME/KEY: misc_feature
<222> LOCATION: (530)..(530)
<223> OTHER INFORMATION: n is a, c, g, or t

<400> SEQUENCE: 67

```
ggaagtaaaa gtcgtaacaa ggtttccgta ggtgaacctg cggaaggatc attaccgagt    60
gcgggctgcc tccgggcgcc caacctccca cccgtgacta cctaacactg ttgcttcggc   120
ggggagccct ttcggggggcg agccgccggg gactactgaa cttcatgcct gagagtgatg   180
cagtctgagt ctgaatataa aatcagtcaa aactttcaac aatggatctc ttggttccgg   240
catcgatgaa gaacgcagcg aactgcgata agtaatgtga attgcagaat tcagtgaatc   300
atcgagtctt tgaacgcaca ttgcgccccc tggcattccg gggggcatgc ctgtccgagc   360
gtcattgctg cccatcaagc ccggcttgtg tgttgggtcg tcgtcccccc cnggggacg    420
ggcccgaaag gcagcggcgg caccgtgtcc ggtcctcgag cgtatgggc tttgtcaccc   480
gctcgattna gggccggccg ggcgccagcc gacgtctcca accatttttn ttcaggttga   540
cctcggatca ggtagggata cccgctgaac ttaagcatat caataagcgg aggaaaagaa   600
accaaccggg attgccccag taacggcgag tgaagcggca agagctcaaa tttgaaatct   660
```

-continued

```
ggcccctccg gggtccgagt tgtaatttgc agaggatgct tcgggtgcgg ccctgtcta      720 agtgccctgg aacgggccgt cagagagggt gagaatcccg tcttgggcag ggtgcccgtg      780
cccgtgtgaa gctccttcga cgagtcgagt tgtttgggaa tgcagctcta aatgggtggt      840
aaatttcatc taaagctaaa taccggccgg agaccgatag cgcacaagta gagtgatcga      900
aagatgaaaa gcactttgaa aagagagtta aacagcacgt gaaattgttg aaagggaagc      960
gcttgcgacc agactcggcc tcggggttca gccagcattc gtgctggtgt acttccccgg     1020
ggccgggcca gcgtcggttc gggcggccgg tcaaagg                              1057
```

<210> SEQ ID NO 68
<211> LENGTH: 1028
<212> TYPE: DNA
<213> ORGANISM: Aspergillus versicolor
<220> FEATURE:
<221> NAME/KEY: misc_feature
<222> LOCATION: (26)..(26)
<223> OTHER INFORMATION: n is a, c, g, or t
<220> FEATURE:
<221> NAME/KEY: misc_feature
<222> LOCATION: (44)..(44)
<223> OTHER INFORMATION: n is a, c, g, or t
<220> FEATURE:
<221> NAME/KEY: misc_feature
<222> LOCATION: (58)..(58)
<223> OTHER INFORMATION: n is a, c, g, or t
<220> FEATURE:
<221> NAME/KEY: misc_feature
<222> LOCATION: (64)..(65)
<223> OTHER INFORMATION: n is a, c, g, or t
<220> FEATURE:
<221> NAME/KEY: misc_feature
<222> LOCATION: (72)..(74)
<223> OTHER INFORMATION: n is a, c, g, or t
<220> FEATURE:
<221> NAME/KEY: misc_feature
<222> LOCATION: (159)..(159)
<223> OTHER INFORMATION: n is a, c, g, or t
<220> FEATURE:
<221> NAME/KEY: misc_feature
<222> LOCATION: (162)..(162)
<223> OTHER INFORMATION: n is a, c, g, or t
<220> FEATURE:
<221> NAME/KEY: misc_feature
<222> LOCATION: (224)..(224)
<223> OTHER INFORMATION: n is a, c, g, or t
<220> FEATURE:
<221> NAME/KEY: misc_feature
<222> LOCATION: (236)..(236)
<223> OTHER INFORMATION: n is a, c, g, or t
<220> FEATURE:
<221> NAME/KEY: misc_feature
<222> LOCATION: (251)..(252)
<223> OTHER INFORMATION: n is a, c, g, or t
<220> FEATURE:
<221> NAME/KEY: misc_feature
<222> LOCATION: (254)..(254)
<223> OTHER INFORMATION: n is a, c, g, or t
<220> FEATURE:
<221> NAME/KEY: misc_feature
<222> LOCATION: (256)..(256)
<223> OTHER INFORMATION: n is a, c, g, or t
<220> FEATURE:
<221> NAME/KEY: misc_feature
<222> LOCATION: (278)..(279)
<223> OTHER INFORMATION: n is a, c, g, or t
<220> FEATURE:
<221> NAME/KEY: misc_feature
<222> LOCATION: (282)..(284)
<223> OTHER INFORMATION: n is a, c, g, or t
<220> FEATURE:
<221> NAME/KEY: misc_feature
<222> LOCATION: (287)..(287)

<223> OTHER INFORMATION: n is a, c, g, or t
<220> FEATURE:
<221> NAME/KEY: misc_feature
<222> LOCATION: (299)..(299)
<223> OTHER INFORMATION: n is a, c, g, or t
<220> FEATURE:
<221> NAME/KEY: misc_feature
<222> LOCATION: (334)..(334)
<223> OTHER INFORMATION: n is a, c, g, or t
<220> FEATURE:
<221> NAME/KEY: misc_feature
<222> LOCATION: (356)..(358)
<223> OTHER INFORMATION: n is a, c, g, or t
<220> FEATURE:
<221> NAME/KEY: misc_feature
<222> LOCATION: (361)..(361)
<223> OTHER INFORMATION: n is a, c, g, or t
<220> FEATURE:
<221> NAME/KEY: misc_feature
<222> LOCATION: (370)..(371)
<223> OTHER INFORMATION: n is a, c, g, or t
<220> FEATURE:
<221> NAME/KEY: misc_feature
<222> LOCATION: (408)..(408)
<223> OTHER INFORMATION: n is a, c, g, or t
<220> FEATURE:
<221> NAME/KEY: misc_feature
<222> LOCATION: (435)..(436)
<223> OTHER INFORMATION: n is a, c, g, or t
<220> FEATURE:
<221> NAME/KEY: misc_feature
<222> LOCATION: (441)..(441)
<223> OTHER INFORMATION: n is a, c, g, or t

<400> SEQUENCE: 68

| | | | | | |
|---|---|---|---|---|---|
| tgcgcacgtt | cactaagcaa | caagcngctt | cttacatatt | taaagtttg | agaatagngt | 60 |
| taanngttg | tnnnttcaac | cccaatgcct | ctaatcattc | gctttacctc | ataaaactga | 120 |
| tccgcgttac | tgctatcctg | agggaaactt | cggcaggana | cncagctacc | agatggttcg | 180 |
| attagtctttt | cgcccctata | cccaaatttg | acgatcgatt | tgcnacgtca | gaaccngctg | 240 |
| cgagcctcca | nncncnagag | tttcctctgg | cttcaccnnc | tnnnatntca | ggcatagtnt | 300 |
| caccatcttt | cgggtcccca | cagctacgct | cgtnactcaa | atccatccga | agactnnntc | 360 |
| naggatcggn | ntcgatggtg | cgccccaaag | gggctcccac | ctccgttncg | ctttcactgc | 420 |
| gcgtacgggt | ttganncacc | ncgaacactc | gcgtagatgt | tagactcctt | ggtccgtgtt | 480 |
| tcaagacggg | tcgtttgtga | ccattacgcc | agcgtccgtg | ccgaagcgcg | ttcctcggtc | 540 |
| caggctggcc | gcattgcacc | ccaggctata | agacgtcccg | gaggacgata | cattcctggg | 600 |
| gcctttgacc | ggccgcccga | accgacgctg | gcccggcccc | ggggaagtac | accagcacga | 660 |
| atgctggctg | aaccccgagg | ccgagtctgg | tcgcaagcgc | ttcccttttca | acaatttcac | 720 |
| gtgctgttta | actctctttt | caaagtgctt | ttcatctttc | gatcactcta | cttgtgcgct | 780 |
| atcggtctcc | ggccggtatt | tagctttaga | tgaaatttac | cacccattta | gagctgcatt | 840 |
| cccaaacaac | tcgactcgtc | gaaggagctt | cacacgggca | cgggcaccct | gcccaagacg | 900 |
| ggattctcac | cctctctgac | ggcccgttcc | agggcactta | gacaggggcc | gcacccgaag | 960 |
| catcctctgc | aaattacaac | tcggacccccg | gaggggccag | atttcaaatt | tgagctcttg | 1020 |
| ccgcttca | | | | | | 1028 |

<210> SEQ ID NO 69
<211> LENGTH: 1024
<212> TYPE: DNA
<213> ORGANISM: Eurotium herbariorum

<400> SEQUENCE: 69

```
tccgtaggtg aacctgcgga aggatcatta ccgagtgcgg gccctctggg tccaacctcc    60
catccgtgtc tatctgtacc ctgttgcttc ggcgtggcca cggcccgccg aagactaaca   120
tttgaacact gtctgaagtt tgcagtctga gttttagtt aaacaataat taaaactttc   180
aacaacggat ctcttggttc cggcatcgat gaagaacgca gcgaaatgcg ataattaatg   240
tgaattgcag aattcagtga atcatcgagt ctttgaacgc acattgcgcc cctggtatt   300 ccggggggca tgcctgtccg agcgtcattg ctgccctcaa gcacggcttg tgtgttgggc   360
ttccgtccct ggtaacgggg acgggcccaa aaggcagtgg cggcaccatg tctggtcctc   420
gagcgtatgg ggctttgtca cccgctcccg taggtccagc tggcagctag cctcgcaacc   480
aatcttttta accaggttga cctcggatca ggtagggata cccgctgaac ttaagcatat   540
caataagcgg aggaaaagaa accaacaggg attgcctcag taacggcgag tgaagcggca   600
agagctcaaa tttgaaatct ggcccctccg gggtccgagt tgtaatttgt agaggatgct   660
tcgggtgcgg cccccgtcta agtgctctgg aacgggccat cggagagggt gagaatcccg   720
tctgggacgg ggtgtccgcg tccatgtgaa gctccttcga cgagtcgagt tgtttgggaa   780
tgcagctcta aatgggtggt aaatttcatc taaagctaaa tactggccgg agaccgatag   840
cgcacaagta gagtgatcga agatgaaaa gcactttgaa aagagagtta aacagcacgt   900
gaaattgttg aaagggaagc gcttgcgacc agactcgctt ccggggttca gccggctttc   960
gggccggtgt acttccccgg gggcgggcca gcgtcggttt gggcggccgg tcaaaggccc  1020
ctgg                                                               1024
```

<210> SEQ ID NO 70
<211> LENGTH: 984
<212> TYPE: DNA
<213> ORGANISM: Eurotium herbariorum

<400> SEQUENCE: 70

```
tctatgctca cgttcactaa gcaacaagag cttcttacat atttaaagtt tgagaatagg    60
ttaaggttgt ttcaaccccca aggcctctaa tcattcgctt tacctcataa aactgattac   120
gcgttactgc tatcctgagg gaaacttcgg caggaaccag ctaccagatg gttcgattag   180
tctttcgccc ctatacccaa atttgacgat cgatttgcac gtcagaaccg ctgcgagcct   240
ccaccagagt ttcctctggc ttcgccctat tcaggcatag ttcaccatct ttcgggtccc   300
cacagctacg ctcttactca aatccatccg aagacatcag gatcggtcga tggtgcgccc   360
ctcgaggggg ctcccaccct cgttcgcttt cactgcgcgc acgggtttga cacccgaaca   420
ctcgcgtaga tgttagactc cttggtccgt gtttcaagac gggtcgttta cgaccattat   480
gccagcgtcc gtgccgaagc gcgttcctcg gtccaggctg gccgcatgac acccctggct   540
ataaggcgcc ccgaggggcg ttacattcca ggggcctttg accggccgcc caaaccgacg   600
ctggcccgcc cccggggaag tacaccggcc cgaaagccgg ctgaacccg gaagcgagtc   660 tggtcgcaag cgcttccctt tcaacaattt cacgtgctgt ttaactctct tttcaaagtg   720
cttttcatct ttcgatcact ctacttgtgc gctatcggtc tccggccagt atttagcttt   780
agatgaaatt taccacccat ttagagctgc attcccaaac aactcgactc gtcgaaggag   840
cttcacatgg acgcggacac cccgtcccag acgggattct caccctctcc gatggcccgt   900
tccagagcac ttagacgggg gccgcacccg aagcatcctc tacaaattac aactcggacc   960
ccggaggggc cagatttcaa attt                                          984
```

<210> SEQ ID NO 71
<211> LENGTH: 979
<212> TYPE: DNA
<213> ORGANISM: Penicillium corylophilum

<400> SEQUENCE: 71

| | | | | | | |
|---|---|---|---|---|---|---|
| cttccgtagg | tgaacctgcg | gaaggatcat | taccgagtga | gggccctctg | gtccaacct | 60 |
| cccacccatg | tttactgtac | cttgttgctt | cggcgggccc | gcctcacggc | cgccggggg | 120 |
| cttctgccct | ctggcccgcg | cccgccgaag | acaccattga | acactgtctg | aagattgcag | 180 |
| tctgagcaat | tagctaaata | agttaaaact | ttcaacaacg | gatctcttgg | ttccggcatc | 240 |
| gatgaagaac | gcagcgaaat | gcgatacgta | atgtgaattg | cagaattcag | tgaatcatcg | 300 |
| agtctttgaa | cgcacattgc | gccccttggt | attccggggg | catgcctgt | ccgagcgtca | 360 |
| tgctgccct | caagcacggc | ttgtgtgttg | ggccccgtcc | tccttcccgg | gggacgggcc | 420 |
| cgaaaggcag | cggcggcacc | gcgtccggtc | ctcgagcgta | tggggctttg | tcacccgctc | 480 |
| ttgtaggccc | ggccggcgct | tgccgacaac | catcaatctt | ttttcaggtt | gacctcggat | 540 |
| caggtaggga | tacccgctga | acttaagcat | atcaataagc | ggaggaaaag | aaaccaacag | 600 |
| ggattgcctc | agtaacggcg | agtgaagcgg | caagagctca | aatttgaaag | ctggcccct | 660 |
| cggggtccgc | attgtaattt | gcagaggatg | cttcgggagt | ggcccccatc | taagtgctct | 720 |
| ggaacgggcc | gtcatagagg | gtgagaatcc | cgtatgggat | ggggtgtccg | cgaccatgtg | 780 |
| aagctccttc | gacgagtcga | gttgtttggg | aatgcagctc | taaatgggtg | gtaaatttca | 840 |
| tctaaagcta | aatattggcc | ggagaccgat | agcgcacaag | tagagtgatc | gaaagatgaa | 900 |
| aagcactttg | aaaagagagt | taaaaagcac | gtgaaattgt | tgaaagggaa | gcgcttgcga | 960 |
| ccagactcgc | ctacggggt | | | | | 979 |

<210> SEQ ID NO 72
<211> LENGTH: 979
<212> TYPE: DNA
<213> ORGANISM: Penicillium corylophilum

<400> SEQUENCE: 72

| | | | | | | |
|---|---|---|---|---|---|---|
| tctatgccac | gttcactaag | caacaagggc | ttcttacata | tttaaagttt | gagaataggt | 60 |
| taaggttgtt | tcaaccccaa | ggcctctaat | cattcgcttt | acctcataaa | actgaattcg | 120 |
| cgttactgct | atcctgaggg | aaacttcggc | aggaaccagc | tactagatgg | ttcgattagt | 180 |
| ctttcgcccc | tacccaaa | tttgacgatc | gatttgcacg | tcagaaccgc | tgcgagcctc | 240 |
| caccagagtt | tcctctggct | tcgccctatt | caggcatagt | tcaccatctt | tcgggtccca | 300 |
| acagctacgc | tcttactcaa | atccatccga | agacatcagg | atcggtcgat | ggtgcacccg | 360 |
| tgagggttcc | cacctccgtt | cgctttcact | gcgcgcacgg | gtttgacacc | cgaacactcg | 420 |
| cgtagatgtt | agactccttg | gtccgtgttt | caagacgggt | cgcttacgac | cattatgcca | 480 |
| gcgtccgtgc | cgaagcgcgt | tcctcggtcc | gggctggccg | catggcaccc | tcggctataa | 540 |
| gacgccccga | gaggcgttac | attccgaggg | cctttgaccg | gccgcccaaa | ccgacgctgg | 600 |
| cccgcccacg | gggaagtaca | ccggtacgaa | taccggctga | accccgtagg | cgagtctggt | 660 |
| cgcaagcgct | tccctttcaa | caatttcacg | tgcttttaa | ctctcttttc | aaagtgcttt | 720 |
| tcatctttcg | atcactctac | ttgtgcgcta | tcggtctccg | gccaatattt | agctttagat | 780 |
| gaaatttacc | acccatttag | agctgcattc | ccaaacaact | cgactcgtcg | aaggagcttc | 840 |
| acatggtcgc | ggacacccca | tcccatacgg | gattctcacc | ctctatgacg | gccgttcca | 900 |

```
gagcacttag atgggggcca ctcccgaagc atcctctgca aattacaatg cggaccccga    960
gggggccagc tttcaaatt                                                 979
```

<210> SEQ ID NO 73
<211> LENGTH: 961
<212> TYPE: DNA
<213> ORGANISM: Penicillium decumbens

<400> SEQUENCE: 73

```
tccgtaggtg aacctgcgga aggatcatta ccgagtgagg gccctctggg tccaacctcc     60
cacccgtgtc tattgtacct tgttgcttcg gcgggcccgc cgcaaggccg ccggggggct    120 tctgccccg ggcccgcgcc cgccgaagac gccattgaac gctgtctgaa gattgcagtc    180
tgagcaatta gctaaataag ttaaaacttt caacaacgga tctcttggtt ccggcatcga    240
tgaagaacgc agcgaaatgc gatacgtaat gtgaattgca gaattcagtg aatcatcgag    300
tctttgaacg cacattgcgc ccctggtat tccggggggc atgcctgtcc gagcgtcatt     360 gctgcccta agcacggctt atgtgttggg cctccgtcct cctttggggg acgggcccg     420 aaaggcagcg gcggcaccgc gtccggtcct cgagcgtatg ggcttcgtc acccgctctg    480 taggtccggc cggcgcctgc cgaacacatc aatcttttt ccaggttgac ctcggatcag     540
gtagggatac ccgctgaact taagcatatc aataagcgga ggaaaagaaa ccaacaggga    600
ttgcctcagt aacggcgagt gaagcggcaa gagctcaaat ttgaaagctg gccccctcgg    660
ggtccgcatt gtaatttgca gaggatgctt cgggagtggc ccccatctaa gtgctctgga    720
acgggccgtc atagagggtg agaatcccgt atgggatggg gtgtccgcga ccatgtgaag    780
ctccttcgac gagtcgagtt gtttgggaat gcagctctaa atgggtggta aatttcatct    840
aaagctaaat attggccgga gaccgatagc gcacaagtag agtgatcgaa agatgaaaag    900
cactttgaaa agagagttaa aaagcacgtg aaattgttga agggaagcg cttgcgacca     960 g                                                                   961
```

<210> SEQ ID NO 74
<211> LENGTH: 963
<212> TYPE: DNA
<213> ORGANISM: Penicillium decumbens

<400> SEQUENCE: 74

```
attctatgcc acgttcacta agcaacaagg gcttcttaca tatttaaagt ttgagaatag     60
gttaaggttg tttcaacccc aaggcctcta atcattcgct ttacctcata aaactgaatt    120
cgcgttactg ctatcctgag ggaaacttcg gcaggaacca gctactagat ggttcgatta    180
gtctttcgcc cctatacca aatttgacga tcgattgca cgtcagaacc gctgcgagcc     240
tccaccagag tttcctctgg cttcgccta ttcaggcata gttcaccatc tttcgggtcc     300
caacagctac gctcttactc aaatccatcc gaagacttca ggatcggtcg atggtgcacc    360
cgtgagggtt cccacctccg ttcgctttca ctgcgcgcac gggtttgaca cccgaacact    420
cgcgtagatg ttagactcct tggtccgtgt ttcaagacgg gtcgcttacg accattatgc    480
cagcgtccgt gccgaagcgc gttcctcggt ccgggctggc gcatggcac cctcggctat    540 aagacgcccc gagaggcgtt acattccgag ggcctttgac cggccgccca aaccgacgct    600
ggcccgccca cggggaagta caccggtacg aataccggct gaaccccgca ggcgagtctg    660
gtcgcaagcg cttcccttc aacaatttca cgtgcttttt aactctcttt tcaaagtgct    720
```

| | |
|---|---|
| tttcatctttt cgatcactct acttgtgcgc tatcggtctc cggccaatat ttagctttag | 780 |
| atgaaattta ccacccattt agagctgcat tcccaaacaa ctcgactcgt cgaaggagct | 840 |
| tcacatggtc gcggacaccc catcccatac gggattctca ccctctatga cggcccgttc | 900 |
| cagagcactt agatggggc cactcccgaa gcatcctctg caaattacaa tgcggacccc | 960 |
| gag | 963 |

<210> SEQ ID NO 75
<211> LENGTH: 1049
<212> TYPE: DNA
<213> ORGANISM: Aspergillus sydowii

<400> SEQUENCE: 75

| | |
|---|---|
| ggaagtaaaa gtcgtaacaa ggtttccgta gggtgaacct gcggaaggat cattactgag | 60 |
| tgcgggctgc ctccgggcgc ccaacctccc acccgtgaat acctaacact gttgcttcgg | 120 |
| cggggaaccc cctcggggc gagccgccgg ggactactga acttcatgcc tgagagtgat | 180 |
| gcagtctgag tctgaatata aaatcagtca aactttcaa caatggatct cttggttccg | 240 |
| gcatcgatga agaacgcagc gaactgcgat aagtaatgtg aattgcagaa ttcagtgaat | 300 |
| catcgagtct ttgaacgcac attgcgcccc ctggcattcc gggggcatg cctgtccgag | 360 |
| cgtcattgct gcccatcaag cccggcttgt gtgttgggtc gtcgtccccc cggggggacg | 420 |
| ggcccgaaag gcagcggcgg caccgtgtcc ggtcctcgag cgtatggggc tttgtcaccc | 480 |
| gctcgactag ggccggccgg gcgccagccg acgtctccaa ccatttttct tcaggttgac | 540 |
| ctcggatcag gtagggatac ccgctgaact taagcatatc aataagcgga ggaaaagaaa | 600 |
| ccaaccggga ttgcctcagt aacggcgagt gaagcggcaa gagctcaaat ttgaaatctg | 660 |
| gcccctccgg ggtccgagtt gtaatttgca gaggatgctt cgggtgcggc ccctgtctaa | 720 |
| gtgccctgga acgggccgtc agagagggtg agaatcccgt cttgggcagg gtgcccgtgc | 780 |
| ccgtgtgaag ctccttcgac gagtcgagtt gtttgggaat gcagctcaaa atgggtggta | 840 |
| aatttcatct aaagctaaat accggccgga gaccgatagc gcacaagtag agtgatcgaa | 900 |
| agatgaaaag cactttgaaa agagagttaa acagcacgtg aaattgttga agggaagcg | 960 |
| cttgcaacca gactcggcct cggggttcag ccagcattcg tgctggtgta cttccccggg | 1020 |
| gccgggccag cgtcggtttg ggcggccgg | 1049 |

<210> SEQ ID NO 76
<211> LENGTH: 1006
<212> TYPE: DNA
<213> ORGANISM: Aspergillus sydowii

<400> SEQUENCE: 76

| | |
|---|---|
| tctatgcgca cgttcactaa gcaacaagcg cttcttacat atttaaagtt tgagaatagg | 60 |
| ttaaggttgt ttcaaccccca atgcctctaa tcattcgctt tacctcataa aactgatccg | 120 |
| cgttactgct atcctgaggg aaacttcggc aggaaccagc tactagatgg ttcgattagt | 180 |
| ctttcgcccc tatacccaaa tttgacgatc gatttgcacg tcagaaccgc tgcgagcctc | 240 |
| caccagagtt cctctggct tcaccctatt caggcatagt tcaccatctt tcgggtcccc | 300 |
| acagctacgc tcgtactcaa atccatccga agacatcagg atcggtcgat ggtgcgcccc | 360 |
| ggggggggctc ccacctccgt tcgctttcac tgcgcgtacg ggtttgacac ccgaacactc | 420 |
| gcgtagatgt tagactcctt ggtccgtgtt tcaagacggg tcgtttgcga ccattacgcc | 480 |
| agcgtccgtg ccgaagcgcg ttcctcggtc caggctggcc gcattgcacc ccaggctata | 540 |

```
agacgtcccg gaggacgata cattcctggg gcctttgacc ggccgcccaa accgacgctg    600
gcccggcccc ggggaagtac accagcacga atgctggctg aaccccgagg ccgagtctgg    660
ttgcaagcgc ttcccttttca acaatttcac gtgctgttta actctctttt caaagtgctt    720
ttcatctttc gatcactcta cttgtgcgct atcggtctcc ggccggtatt tagctttaga    780
tgaaatttac cacccatttt gagctgcatt cccaaacaac tcgactcgtc gaaggagctt    840
cacacgggca cgggcaccct gcccaagacg ggattctcac cctctctgac ggcccgttcc    900
agggcactta gacaggggcc gcacccgaag catcctctgc aaattacaac tcggaccccg    960
gaggggccag atttcaaatt tgagctcttg ccgcttcact cgccgt                  1006

<210> SEQ ID NO 77
<211> LENGTH: 1004
<212> TYPE: DNA
<213> ORGANISM: Wallemia sebi
<220> FEATURE:
<221> NAME/KEY: misc_feature
<222> LOCATION: (513)..(513)
<223> OTHER INFORMATION: n is a, c, g, or t

<400> SEQUENCE: 77
acctgcggaa ggatcattag tgattaatta ttgagtgtaa aaaactcata atcttctaca     60
aaccactgtt ttaaaatgtt tactagaatg tccaagcagt taagctgttg aaatattaaa    120
agttttataa aactttcagc aacggatctc ttggttcagg catcgatgaa gaacgcagcg    180
aaatgcgata agtaatgtga attgcagata cagtgaatca tcgaatcttt gaacgcaaat    240
ggcactctat ggtattccgt agagtacgtc tgtttgagcg tcgcgaacat ctccacaatt    300 agttttttt aaaattagtt gaggggtttg aggttgtcat ataaacaatg actcccttta    360
aaataattag tgatgacctt atgaatgggt taatactgtg tgttataatg gattacatcc    420
atcaccagtc agagagtaat ctcgccttag taatttgtag tgattgcttc taactgccat    480
tggcaacaac ctgatcaaat cgacctccaa tcncatggga ttacccgctg aacttaagca    540
tatcaataag cggaggaaaa gaaactaaca aggattcccc tagtaacggc gagtgaagag    600
ggaaaagctc aaatttaaaa gctgttgtct ttcaggcaac cgcattgtaa tctcaagaag    660
tgttttcgat tgtagcctgc gtataagtac cttggaatag gttggcatag agggtgaaac    720
tcccgtcttt gatgcagatt actatgatca tgtgatacac tttctaagag tcgagttgtt    780
tgggaatgca gctcaaaatg ggtggtaaat tccatctaaa gctaaatatt ggcctgagac    840
cgatagcgaa caagtaccgt gagggaaaga tgaaaagcac tttggaaaga gagtcaaaca    900
gaacgtgaaa ttgctgaaag ggaagcgttt gaagttagtc tgatagaagt tgttcaattg    960
ttactttggt ttcaatgtat gcaactttt atcggtcaac atca                    1004

<210> SEQ ID NO 78
<211> LENGTH: 938
<212> TYPE: DNA
<213> ORGANISM: Wallemia sebi

<400> SEQUENCE: 78
gttgctcagt tcataaagta acaagagcct cttacatatt taaagtttga gaataggtaa     60
aggatgtttc atcccctagg cctctaatca ttcgctttac cacataaaac tgatacaagt    120
gtctgctatc ctgagggaaa cttcggcagg aaccagctac tagatggttc gattagtctt    180
tcgcccctat acccaaattt gacgatcgat ttgcacgtca gaaccgctac gagcctccac    240
```

```
cagagtttcc tctggcttca ccctattcag gcatagttca ccatctttcg ggtcccaaca      300
tatatgctct tactcaaatc catcattata aaaattccag atcggtcgat gttgcagctt      360
acgcttcaca cctacattca ctttcattac gcattcgagt tgtcactca aatactcgca      420 gatatgttag actccttggt ccgtgtttca agacgggtcg cttaaagcta ttttgtcaac      480
atccttagtg taataggtgc gaacaccttc ctaaaggta cactgccgtc ctcaatctca      540
atcaatgttt atgataatag tctataacac tacaaatgta gccacattcc tattacctt      600 atccatcaat caaaattgat gttgaccgat aaaaagttgc atacattgaa accaaagtaa      660
caattgaaca acttctatca gactaacttc aaacgcttcc ctttcagcaa tttcacgttc      720
tgtttgactc tctttccaaa gtgcttttca tctttccctc acggtacttg ttcgctatcg      780
gtctcaggcc aatatttagc tttagatgga atttaccacc cattttgagc tgcattccca      840
aacaactcga ctcttagaaa gtgtatcaca tgatcatagt aatctgcatc aaagacggga      900
gtttcaccct ctatgccaac ctattccaag gtacttat                             938
```

```
<210> SEQ ID NO 79
<211> LENGTH: 996
<212> TYPE: DNA
<213> ORGANISM: Mucor plumbeus

<400> SEQUENCE: 79
ttccgtaggt gaacctgcgg aaggatcatt aaataatcaa taatcttggc ttgtccatta       60
ttatctattt actgtgaact gtattattat ttgacgtttg agggatgttc caatgttata      120
aggatagaca ttggagatgt taaccgagtc ataatcaggt ttaggcctgg tatcctatta      180
ttatttacca aatgaattca gaattaatat tgtaacatag acctaaaaaa tctataaaac      240 aactttaac aacggatctc ttggttctcg catcgatgaa gaacgtagca aagtgcgata      300
actagtgtga attgcatatt cagtgaatca tcgagtcttt gaacgcaact tgcgctcatt      360
ggtattccaa tgagcacgcc tgtttcagta tcaaaacaaa ccctctattc aacttttgtt      420
gtataggatt attgggggcc tctcgatctg tatagatctt gaaacccttg aaatttacta      480
aggcctgaac ttgtttaatg cctgaacttt ttttaatat aaaggaaagc tcttgtaatt      540
gactttgatg gggcctccca aataaatctc ttttaaattt gatctgaaat caggtgggat      600
tacccgctga acttaagcat atcaataagc ggaggaaaag aaaataacaa tgatttccct      660
agtaacggcg agtgaagagg aaagagctca agttggaaac ctgtttggct tagctaaacc      720
ggattgtaaa ctgtagaaac attttccaga tacactagaa aaaaagtcc tttggaacag      780 ggcatcatag agggtgagaa tcccgtcttt ggtctaagta gttgtctatt gtgatatgtt      840
ttcaaagagt caggttgttt gggaatgcag cctaaattgg gtggtaaatc tcacctaaag      900
ctaaatattt gcgagagacc gatagcgaac aagtaccgtg agggaaagat gaaaagaact      960
ttgaaaagag agttaaacag tatgtgaaat tgttaa                              996
```

```
<210> SEQ ID NO 80
<211> LENGTH: 986
<212> TYPE: DNA
<213> ORGANISM: Mucor plumbeus

<400> SEQUENCE: 80
ttcatgacct gcttcattaa gcaaacaggg tcggtcttac atatttaaag tttgagaata       60
ggttaaggac atttcgtccc caaggcctct aatcattcgc tttacctcat aaaactgctt      120
ttaagttttt gctatcctga gggaaacttc ggcaggaacc agctactaga tggttcgatt      180
```

```
agtctttcgc ccctataccc aaatttgacg atcgatttgc acgtcagaat cgctacgagc      240
ctccaccaga gtttcctctg gcttcaccct attcaggcat agttcaccat ctttcgggtc      300
ccatcataag tgctttacct cggtcaattc agtataaaac gtcagcgccg ggtgatactg      360
ccatctcgcg atttcgtatc aatcagtttc cttacgcata tgggtttggc acccaaatac      420
ttgcacttat ggtggactcc ttggtccgtg tttcaagacg ggtcatttag agtcattaag      480
ccaacaacct aagcgaataa aaatatact aaacgagttc ctcctttaaa cattagcacc       540
acccgaagca gaaattctaa catttattag cgaaagcgcc cagcaatctt gcctaaaggc      600
attcactgcg ttcctcagtc caatccagag tatgataata ggctataaca cctcgagagg      660
ccacattcct attaattttt tcctccaaat caaactgtcg ttggcaggca tagactgcaa      720
gtgcacccaa aacgaattct aggttgatta caatcaagcc agtctggctc caaacggttc      780 cctttaaca atttcacata ctgtttaact ctcttttcaa agttcttttc atctttccct       840
cacggtactt gttcgctatc ggtctctcgc aaatatttag ctttaggtga gatttaccac      900
ccaatttagg ctgcattccc aaacaacctg actctttgaa aacatatcac aatagacaac      960
tacttagacc aaagacggga ttctca                                           986

<210> SEQ ID NO 81
<211> LENGTH: 1036
<212> TYPE: DNA
<213> ORGANISM: Penicillium citreonigrum

<400> SEQUENCE: 81
tccgtagggt gaacctgcgg aaggatcatt accgagtgag ggccctctgg gtccaacctc       60
ccacccgtgt ttatcgtacc ttgttgcttc ggcgggcccg ccgcaaggcc gccgggggc      120 atctgccctc tggcccgcgc ccgccgaaga caccattgaa cgctgtctga agattgcagt      180
ctgagcaatt agttaaataa cttaaaactt tcaacaacgg atctcttggt tccggcatcg      240
atgaagaacg cagcgaaatg cgatacgtaa tgtgaattgc agaattcagt gaatcatcga      300
gtctttgaac gcacattgcg ccccctggta ttccgggggg catgcctgtc cgagcgtcat      360
tgctgccctc aagcacggct tgtgtgttgg gctccgtcct cctcccgggg acgggcccg      420 aaaggcagcg gcggcaccgc gtccggtcct cgagcgtatg gggcttcgtc acccgctctg      480 tagcccggc cggcgcttgc cgacacatca atcttttttc caggttgacc tcggatcagg      540
tagggatacc cgctgaactt aagcatatca ataagcggag gaaaagaaac caacagggat      600
tgccccagta acgcgagtg aagcggcaag agctcaaatt tgaaagctgg ccccctcggg      660
gtccgcattg taatttgcag aggatgcttc gggagtggcc cccatctaag tgctctggaa      720
cgggccgtca tagagggtga gaatcccgta tgggatgggg tgtccgcgac catgtgaagc      780
tccttcgacg agtcgagttg tttgggaatg cagctctaaa tgggtggtaa atttcatcta      840
aagctaaata ttggccggag accgatacg cacaagtaga gtgatcgaaa gatgaaaagc       900
actttgaaaa gagagttaaa aagcacgtga aattgttgaa agggaagcgc ttgcgaccag      960
actcgcctac ggggttcagc cggtattcgt accggtgtac ttccccgtgg gcgggccagc     1020
gtcggtttgg gcggcc                                                    1036

<210> SEQ ID NO 82
<211> LENGTH: 958
<212> TYPE: DNA
<213> ORGANISM: Penicillium citreonigrum
```

<400> SEQUENCE: 82

```
ctaatgccac gttcactaag caacaagggc ttcttacata tttaaagttt gagaataggt      60
taaggttgtt tcaaccccaa ggcctctaat cattcgcttt acctcataaa actgaattcg     120
cgttactgct atcctgaggg aaacttcggc aggaaccagc tactagatgg ttcgattagt     180
ctttcgcccc tatacccaaa tttgacgatc gatttgcacg tcagaaccgc tgcgagcctc     240
caccagagtt tcctctggct tcgccctatt caggcatagt tcaccatctt tcgggtccca     300
acagctacgc tcttactcaa atccatccga agacatcagg atcggtcgat ggtgcacccg     360
tgagggttcc cacctccgtt cgctttcact gcgcgcacgg gtttgacacc cgaacactcg     420
cgtagatgtt agactccttg gtccgtgttt caagacgggt cgcttacgac cattatgcca     480
gcgtccgtgc cgaagcgcgt tcctcggtct gggctggccg catggcaccc tcggctataa     540
gacgccccga gaggcgttac attccgaggg cctttgaccg gccgcccaaa ccgacgctgg     600
cccgcccacg gggaagtaca ccggtacgaa taccggctga accccgtagg cgagtctggt     660
cgcaagcgct tccctttcaa caatttcacg tgcttttttaa ctctcttttc aaagtgcttt     720
tcatctttcg atcactctac ttgtgcgcta tcggtctccg gccaatattt agctttagat     780
gaaatttacc acccatttag agctgcattc ccaaacaact cgactcgtcg aaggagcttc     840
acatggtcgc ggacacccca tcccatacgg gattctcacc ctctatgacg gcccgttcca     900
gagcacttag atgggggcca ctcccgaagc atcctctgca aattacaatg cggaccccc     958
```

<210> SEQ ID NO 83
<211> LENGTH: 1042
<212> TYPE: DNA
<213> ORGANISM: Aspergillus flavus

<400> SEQUENCE: 83

```
ttccgtaggt gaacctgcgg aaggatcatt accgagtgta gggttcctag cgagcccaac      60
ctcccacccg tgtttactgt accttagttg cttcggcggg cccgccattc atggccgccg     120
ggggctctca gccccgggcc cgcgcccgcc ggagacacca cgaactctgt ctgatctagt     180
gaagtctgag ttgattgtat cgcaatcagt taaaactttc aacaatggat ctcttggttc     240
cggcatcgat gaagaacgca gcgaaatgcg ataactagtg tgaattgcag aattccgtga     300
atcatcgagt ctttgaacgc acattgcgcc cctggtatt ccgggggca tgcctgtccg     360
agcgtcattg ctgcccatca agcacggctt gtgtgttggg tcgtcgtccc ctctccgggg     420
gggacgggcc ccaaaggcag cggcggcacc cgtccgatc ctcgagcgta tggggctttg     480
tcacccgctc tgtaggcccg ccggcgctt gccgaacgca atcaatctt tttccaggtt     540
gacctcggat caggtaggga tacccgctga acttaagcat atcaataagc ggaggaaaag     600
aaaccaaccg ggattgcctc agtaacggcg agtgaagcgg caagagctca aatttgaaag     660
ctggctcctt cggggtccgc attgtaattt gcagaggatg cttcgggtgc ggcccctgtc     720
taagtgccct ggaacgggcc gtcagagagg gtgagaatcc cgtctgggat ggggtgtccg     780
cgcccgtgtg aagctccttc gacgagtcga gttgtttggg aatgcagctc taaatgggtg     840
gtaaatttca tctaaagcta aatactggcc ggagaccgat agcgcacaag tagagtgatc     900
gaaagatgaa aagcactttg aaaagagagt taaaaagcac gtgaaattgt tgaagggaa     960
gcgcttgcga ccagactcgc ctccagggtt cagccggcat tcgtgccggt gtacttccct    1020
gggggcgggc cagcgtcggt tt                                              1042
```

<210> SEQ ID NO 84
<211> LENGTH: 989
<212> TYPE: DNA
<213> ORGANISM: Aspergillus flavus

<400> SEQUENCE: 84

```
tctatgccac gttcactaag caacaagggc ttcttacata tttaaagttt gagaataggt      60
taaggttgtt caaccccaa tgcctctaat cattcgcttt acctcataaa actgaattcg      120
cgttactgct atcctgaggg aaacttcggc aggaaccagc tactagatgg ttcgattagt      180
ctttcgcccc tatacccaaa tttgacgatc gatttgcacg tcagaaccgc tgcgagcctc      240
caccagagtt cctctggct tcgcccctatt caggcatagt tcaccatctt tcgggtcccc      300
acatttacgc tcttactcaa atccatccga agacatcagg atcggtcgat ggtgcgcccc      360
acgaggggc tcccacctcc gttcgctttc actgcgcgta cgggtttgac acccgaacac      420
tcgcgtagat gttagactcc ttggtccgtg tttcaagacg ggtcgtttac gaccattatg      480
ccagcgtccg tgccgaagcg cgttcctcgg tccaggctgg ccgcattgca ctcccggcta      540
taaggtgccc cggagggcac tacattccgg gagcctttga ccggccgccc aaaccgacgc      600
tggcccgccc ccagggaagt acaccggcac gaatgccggc tgaaccctgg aggcgagtct      660
ggtcgcaagc gcttcccttt caacaatttc acgtgctttt taactctctt ttcaaagtgc      720
ttttcatctt tcgatcactc tacttgtgcg ctatcggtct ccggccagta tttagcttta      780
gatgaaattt accacccatt tagagctgca ttcccaaaca actcgactcg tcgaaggagc      840
ttcacacggg cgcggacacc ccatcccaga cgggattctc accctctctg acggccgtt      900
ccagggcact tagacagggg ccgcacccga agcatcctct gcaaattaca atgcggaccc      960
cgaaggagcc agctttcaaa tttgagctc                                       989
```

<210> SEQ ID NO 85
<211> LENGTH: 1054
<212> TYPE: DNA
<213> ORGANISM: Aspergillus ochraceus

<400> SEQUENCE: 85

```
ggaagtaaaa gtcgtaacaa ggtttccgta ggtgaacctg cggaaggatc attactgagt      60
gagggtccct cggggcccaa cctcccaccc gtgtataccg taccttgttg cttcggcgag      120
cccgccccct ttttcttta gggggcacag cgctcgccgg agacaccaac gtgaacactg      180
tctgaagttt tgtcgtctga gtcgattgta tcgcaatcag ttaaaacttt caacaatgga      240
tctcttggtt ccggcatcga tgaagaacgc agcgaaatgc gataattaat gtgaattgca      300
gaattcagtg aatcatcgag tctttgaacg cacattgcac cccctggtat tccgggggt      360
atgcctgtcc gagcgtcatt gctgccctca agcacggctt gtgtgttggg tcgtcgtccc      420
cccccagggg gacgggcccg aaaggcagcg gcggcaccgc gtccggtcct cgagcgtatg      480
gggcttttgtc acccgctctt gtaggccggg ccggctgctg gccgacgctg aaaagcaacc      540
aactatttt ccaggttgac ctcggatcag gtagggatac ccgctgaact taagcatatc      600
aataagcgga ggaaaagaaa ccaacccggga ttgcctcagt aacggcgagt gaagcggcaa      660
gagctcaaat ttgaaatctg gccccctcgg ggtccgagtt gtaatttgca gaggatgctt      720
cgggtgcggc cccgtctaa gtgccctgga acgggccgtc atagagggtg agaatcccgt      780
ctgggacggg gtgtccgcgt ccgtgtgaag ctccttcgac gagtcgagtt gtttgggaat      840
gcagctctaa atgggtggta aatttcatct aaagctaaat actggccgga gaccgatagc      900
```

| | |
|---|---|
| gcacaagtag agtgatcgaa agatgaaaag cactttgaaa agagagttaa aaagcacgtg | 960 |
| aaattgttga aagggaagcg cttgcgacca gactcgcccg cggggttcag ccggcattcg | 1020 |
| tgccggtgta cttccccgcg ggcgggccag cgtc | 1054 |

<210> SEQ ID NO 86
<211> LENGTH: 995
<212> TYPE: DNA
<213> ORGANISM: Aspergillus ochraceus

<400> SEQUENCE: 86

| | |
|---|---|
| tctatgccac gttcactaag caacaagggc ttcttacata tttaaagttt gagaataggt | 60 |
| taaggttgtt caaccccaa tgcctctaat cattcgcttt acctcataaa actgatccgc | 120 |
| gctactgcta tcctgaggga aacttcggca ggaaccagct accagatggt tcgattagtc | 180 |
| tttcgcccct atacccaaat ttgacgatcg atttgcacgt cagaaccgct gcgagcctcc | 240 |
| accagagttt cctctggctt cgccctattc aggcatagtt caccatcttt cgggtcccca | 300 |
| catttacgct cttactcaaa tccatccgaa gacatcagga tcggtcgatg gtgcgccccg | 360 |
| cgggggggct cccacctccg ttcgctttca ctgcgcgcac gggtttgaca cccgaacact | 420 |
| cgcgtagatg ttagactcct tggtccgtgt ttcaagacgg tcgtttacg accattatgc | 480 |
| cagcgtccgt gccgaagcgc gttcctcggt ccaggctggc cgcattgcac ccccggctat | 540 |
| aaggcacccc gaagggtgct acattccggg ggcctttgac cggccgccca aaccgacgct | 600 |
| ggcccgcccg cggggaagta caccggcacg aatgccggct gaaccccgcg ggcgagtctg | 660 |
| gtcgcaagcg cttcccttc aacaatttca cgtgcttttt aactctcttt tcaaagtgct | 720 |
| tttcatcttt cgatcactct acttgtgcgc tatcggtctc cggccagtat ttagctttag | 780 |
| atgaaattta ccacccattt agagctgcat tcccaaacaa ctcgactcgt cgaaggagct | 840 |
| tcacacggac gcggacaccc cgtcccagac gggattctca ccctctatga cggcccgttc | 900 |
| cagggcactt agacggggc cgcacccgaa gcatcctctg caaattacaa ctcggacccc | 960 |
| gaggggggcca gatttcaaat ttgagctctt gccgc | 995 |

<210> SEQ ID NO 87
<211> LENGTH: 987
<212> TYPE: DNA
<213> ORGANISM: Aspergillus penicillioides
<220> FEATURE:
<221> NAME/KEY: misc_feature
<222> LOCATION: (530)..(530)
<223> OTHER INFORMATION: n is a, c, g, or t
<220> FEATURE:
<221> NAME/KEY: misc_feature
<222> LOCATION: (536)..(537)
<223> OTHER INFORMATION: n is a, c, g, or t

<400> SEQUENCE: 87

| | |
|---|---|
| gaaggatcat taccgagtgt ttggacaccc cttctcgggg tgtccgtcct cccatccgtg | 60 |
| tctatttgta ccctgttgct tcggcgggcc cgcccttcgt ggccgccggg gggcttccct | 120 |
| gcccccgggc ccgtgcccgc cggagacctc aaccatgaac actgtctgaa ggttgcagtc | 180 |
| tgagtaccga tataaaaaat cgttaaaact ttcaacaacg gatctcttgg ttccggcatc | 240 |
| gatgaagaac gcagcgaaat gcgatacgta atgtgaattg cagaattcag tgaatcatcg | 300 |
| agtctttgaa cgcacattgc gccccctggt attccggggg gcatgcctgt ccgagcgtca | 360 |
| ttgctgccct caagcacggc ttgtgtgttg ggccccgtc cccctcccag gaaggggacg | 420 |
| ggcccgaaag gcagcggcgg caccgtgtcc ggtcctcgag cgtatgggaa gcaacttttt | 480 |

```
gtcacccgct cctgtaggtc cggccggcgg cctgcccaac cccaaccttn tttttnnaac      540
caggttgacc tcggatcagg tagggatacc cgctgaactt aagcatatca ataagcggag      600
gaaaagaaac caaccgggat tgcctcagta acggcgagtg aagcggcaag agctcaaatt      660
tgaaatctgg cccctccggg gtccgagttg taatttgtag aggatgctcg ggtgcggccc      720
ctgtctaagt gccctggaac gggccatcgg agagggtgag aatcccgtct gggatggggt      780
gtccgtgccc gtgtgaagct ccttcgacga gtcgagttgt ttgggaatgc agctctaaat      840
gggtggtaaa tttcatctaa agctaaatac tggccggaga ccgatagcgc acaagtagag      900
tgatcgaaag atgaaaagca ctttgaaaag agagttaaac agcacgtgaa attgttgaaa      960
gggaagcgct tgcgaccaga ctcgccc                                         987
```

<210> SEQ ID NO 88
<211> LENGTH: 1008
<212> TYPE: DNA
<213> ORGANISM: Aspergillus penicillioides

<400> SEQUENCE: 88

```
tctatgccac gttcacttaa gaaacaaggg cttcttacat atttaaagtt tgagaatagg       60
ttaaggttgt ttcaacccca atgcctctaa tcattcgctt tacctcataa aactgattac      120
gcgttactgc tatcctgagg gaaacttcgg caggaaccag ctaccagatg gttcgattag      180
tctttcgccc ctatacccaa atttgacgat cgatttgcac gtcagaaccg ctgcgagcct      240
ccaccagagt ttcctctggc ttcgcccttt tcaggcatag ttcaccatct ttcgggtccc      300
cacagctacg ctcctactca aatccatccg aagacatcag gatcggtcga tggtgcgccc      360
ctcgaggggg ctcccacctc cgttcgcttt cactgcgcgc acgggtttgc caccgaaca       420 ctcgcgtaga tgttagactc cttggtccgt gtttcaagac gggtcgtttg cgaccattat      480
gccagcgtcc gtgccgaagc gcgttcctcg gtctaggctg gccgcatgac accccggct      540 ataagacgcc cccggagggg cgttacattc cgggggcctt tgaccggccg cccaaaccga      600
cgctggcccg cccccgggga agtacaccgg cccgaaagcc ggctgaaccc cgtgggcgag      660
tctggtcgca agcgcttccc tttcaacaat ttcacgtgct gtttaactct cttttcaaag      720
tgcttttcat ctttcgatca ctctacttgt gcgctatcgg tctccggcca gtatttagct      780
ttagatgaaa tttaccaccc atttagagct gcattcccaa acaactcgac tcgtcgaagg      840
agcttcacac gggcacggac accccatccc agacgggatt ctcaccctct ccgatggccc      900
gttccagggc acttagacag gggccgcacc cgaagcatcc tctacaaatt acaactcgga      960
ccccggaggg gccagatttc aaatttgagc tcttgccgct tcactcgc                1008
```

<210> SEQ ID NO 89
<211> LENGTH: 1063
<212> TYPE: DNA
<213> ORGANISM: Aspergillus ustus
<220> FEATURE:
<221> NAME/KEY: misc_feature
<222> LOCATION: (180)..(181)
<223> OTHER INFORMATION: n is a, c, g, or t
<220> FEATURE:
<221> NAME/KEY: misc_feature
<222> LOCATION: (200)..(201)
<223> OTHER INFORMATION: n is a, c, g, or t
<220> FEATURE:
<221> NAME/KEY: misc_feature
<222> LOCATION: (211)..(211)
<223> OTHER INFORMATION: n is a, c, g, or t
<220> FEATURE:

```
<221> NAME/KEY: misc_feature
<222> LOCATION: (455)..(455)
<223> OTHER INFORMATION: n is a, c, g, or t
<220> FEATURE:
<221> NAME/KEY: misc_feature
<222> LOCATION: (526)..(526)
<223> OTHER INFORMATION: n is a, c, g, or t

<400> SEQUENCE: 89
ggaagtaaaa gtcgtaacaa ggtttccgta ggtgaacctg cggaaggatc attaccgagt      60
gcaggtctgc ccccgggcag gcctaacctc ccacccgtga atacctgacc aacgttgctt     120
cggcggtgcg ccccteeggg ggtagccgcc ggagaccaca ttgaacctct tgtctttagn     180
ntgttgtctg agcttgatan ngcaaaccta nttaaaactt tcaacaatgg atctcttggt    240
tccggcatcg atgaagaacg cagcgaactg cgataagtaa tgtgaattgc agaattcagt    300
gaatcatcga gtctttgaac gcacattgcg ccccctggca ttccgggggg catgcctgtc    360
cgagcgtcat tgctgccctt caagcccggc ttgtgtgttg ggtcgtcgtc ccctccgggg    420
gacgggcccg aaaggcagcg gcggcaccgc gtccnggtcc tcgagcgtat ggggctttgt    480
cacccgctcg attagggccg gccgggcgcc agccggcgtc tccaanccttt tatttttacc    540
aggttgacct cggatcaggt agggataccc gctgaactta agcatatcaa taagcggagg    600
aaaagaaacc aaccgggatt gcctcagtaa cggcgagtga agcggcaaga gctcaaattt    660
gaaatctggc ccctccgggg tccgagttgt aatttgcaga ggatgcttcg ggtgcggccc    720
ctgtctaagt gccctggaac gggccgtcag agagggtgag aatcccgtct tgggcagggt    780
gcccgtgccc gtgtgaagct ccttcgacga gtcgagttgt ttgggaatgc agctctaaat    840
gggtggtaaa tttcatctaa agctaaatac cggccggaga ccgatagcgc acaagtagag    900
tgatcgaaag atgaaaagca ctttgaaaag agagttaaac agcacgtgaa attgttgaaa    960
gggaagcgct tgcgaccaga ctcggccccg gggttcagcc agcactcgtg ctggtgtact   1020
tccccgggg cgggccagcg tcggtttggg cggccggtca aag                       1063

<210> SEQ ID NO 90
<211> LENGTH: 989
<212> TYPE: DNA
<213> ORGANISM: Aspergillus ustus

<400> SEQUENCE: 90
tctatgccac gttcattaag aaacaagggc ttcttacata tttaaagttt gagaataggt      60
taaggttgtt tcaaccccaa tgcctctaat cattcgcttt acctcataaa actgatccgc     120
gttactgcta tcctgaggga aacttcggca ggaaccagct accagatggt tcgattagtc    180
tttcgcccct atacccaaat ttgacgatcg atttgcacgt cagaaccgct gcgagcctcc    240
accagagttt cctctggctt cgccctattc aggcatagtt caccatcttt cgggtcccca    300
cagctacgct cttactcaaa tccatccgaa gacatcagga tcggtcgatg gtgcgcccct    360
tgcgggctc ccacctccgt tcgctttcac tgcgcgtacg ggtttgacac ccgaacactc    420
gcgtagatgt tagactcctt ggtccgtgtt tcaagacggg tcgtttgcga ccattacgcc    480
agcgtccgtg ccgaagcgcg ttcctcggtc cgggctggcc gcattgcacc ccaggctata    540
agacgccccg gagggcgaca cattcctggg gcctttgacc ggccgcccaa accgacgctg    600
gcccgccccc ggggaagtac accagcacga gtgctggctg aacccgggg ccgagtctgg     660
tcgcaagcgc ttccctttca acaatttcac gtgctgttta actctctttt caaagtgctt    720
ttcatctttc gatcactcta cttgtgcgct atcggtctcc ggccggtatt tagctttaga    780
```

```
tgaaatttac cacccattta gagctgcatt cccaaacaac tcgactcgtc gaaggagctt     840
cacacgggca cgggcaccct gcccaagacg ggattctcac cctctctgac ggcccgttcc     900
agggcactta dacaggggcc gcacccgaag catcctctgc aaattacaac tcggaccccg     960
gaggggccag atttcaaatt tgagctctt                                       989

<210> SEQ ID NO 91
<211> LENGTH: 1060
<212> TYPE: DNA
<213> ORGANISM: Aspergillus sclerotiorum

<400> SEQUENCE: 91
ggaagtaaaa gtcgtaacaa ggtttccgta ggtgaacctg cggaaggatc attactgagt      60
gagggtccct cggggcccaa cctcccaccc gtgtataccg taccttgttg cttcggcggg     120
cccgccgcgc aagcggccgc cgggggggcg tcaaaccccc ctccctaggc gagcgcccgc     180
cggagacacc aacgtgaaca ctgtctgaag ttttgttgtc tgagttcgat tgtatcgcaa     240
tcagttaaaa ctttcaacaa tggatctctt ggttccggca tcgatgaaga acgcagcgaa     300
atgcgataat taatgtgaat tgcagaattc agtgaatcat cgagtctttg aacgcacatt     360 gcacccctg gtattccggg gggtatgcct gtccgagcgt cattgctgcc ctcaagcacg     420
gcttgtgtgt tgggtcgtcg tcccccccgg ggacgggccc gaaaggcagc ggcggcaccg     480
cgtccggtcc tcgagcgtat ggggctttgt cacccgctct gtaggcccg gccggcgctg     540 gccgacgctg aaaagcaacc aactatttct ccaggttgac ctcggatcag gtagggatac     600
ccgctgaact taagcatatc aataagcgga ggaaaagaaa ccaaccggga ttgcctcagt     660
aacggcgagt gaagcggcaa gagctcaaat ttgaaatctg gccccctcgg ggtccgagtt     720
gtaatttgca gaggatgctt cgggtgcggc ccccgtctaa gtgccctgga acgggccgtc     780 atagaggggtg agaatcccgt ctgggacggg gtgtccgcgt ccgtgtgaag ctccttcgac     840
gagtcgagtt gtttgggaat gcagctctaa atgggtggta aatttcatct aaagctaaat     900
actggccgga gaccgatagc gcacaagtag agtgatcgaa agatgaaaag cactttgaaa     960
agagagttaa aaagcacgtg aaattgttga aagggaagcg cttgcgacca gactcgcccg    1020
cggggttcag ccggcattcg tgccggtgta cttccccgcg                          1060

<210> SEQ ID NO 92
<211> LENGTH: 935
<212> TYPE: DNA
<213> ORGANISM: Aspergillus sclerotiorum

<400> SEQUENCE: 92
tatgccacgt tcactaagca acaagggctt cttacatatt taaagtttga aataggttaa      60
aggttgtttc aaccccaatg cctctaatca ttcgctttac ctcataaaac tgatccgcgc     120
tactgctatc ctgagggaaa cttcggcagg aaccagctac cagatggttc gattagtctt     180
tcgcccctat acccaaattc gacgatcgat ttgcacgtca gaaccgctgc gagcctccac     240
cagagtttcc tctggcttcg ccctattcag gcatagttca ccatctttcg ggtccccaca     300
tttacgctct tactcaaatc catccgaaga catcaggatc ggtcgatggt gcgccccgcg     360
ggggggctcc cacctccgtt cgctttcact gcgcgcacgg gtttgacacc cgaacactcg     420
cgtagatgtt agactccttg gtccgtgttt caagacgggt cgtttgcaac cattatgcca     480
gcgtccgtgc cgaagcgcgt tcctcggtcc aggctggccg cattgcaccc ccggctataa     540
```

```
ggtgccccg    tagggcact    acattccggg    ggcctttgac    cggccgccca    aaccgacgct      600
ggcccgcccg   cggggaagta   caccggcacg    aatgccggct    gaaccccgcg    ggcgagtctg      660
gtcgcaagcg   cttcccttc    aacaatttca    cgtgctttt     aactctcttt    tcaaagtgct      720
tttcatcttt   cgatcactct   acttgtgcgc    tatcggtctc    cggccagtat    ttagctttag      780
atgaaattta   ccacccattt   agagctgcat    tcccaaacaa    ctcgactcgt    cgaaggagct      840
tcacacggac   gcggacaccc   cgtcccagac    gggattctca    ccctctatga    cggcccgttc      900
cagggcactt   agacggggc    cgcacccgaa    gcatc                                        935
```

```
<210> SEQ ID NO 93
<211> LENGTH: 1094
<212> TYPE: DNA
<213> ORGANISM: Alternaria alternata
<220> FEATURE:
<221> NAME/KEY: misc_feature
<222> LOCATION: (531)..(531)
<223> OTHER INFORMATION: n is a, c, g, or t

<400> SEQUENCE: 93
ggaagtaaaa   gtcgtaacaa   ggtctccgta    agggtaacct    gcggagggat    cattacacaa       60
atatgaaggc   gggctggaac   ctctcggggt    tacagccttg    ctgaattatt    cacccttgtc      120
ttttgcgtac   ttcttgtttc   cttggtgggt    tcgcccacca    ctaggacaaa    cataaacctt      180
ttgtaattgc   aatcagcgtc   agtaacaaat    taataattac    aactttcaac    aacgatctc       240 ttggttctgg   catcgatgaa   gaacgcagcg    aaatgcgata    agtagtgtga    attgcagaat      300
tcagtgaatc   atcgaatctt   tgaacgcaca    ttgcgccctt    tggtattcca    aagggcatgc      360
ctgttcgagc   gtcatttgta   ccctcaagct    ttgcttggtg    ttgggcgtct    tgtctctagc      420
tttgctggag   actcgcctta   aagtaattgg    cagccggcct    actggtttcg    gagcgcagca      480
caagtcgcac   tctctatcag   caaaggtcta    gcatccatta    agcctttttt    ncaacttttg      540
acctcggatc   aggtagggat   acccgctgaa    cttaagcata    tcaataagcg    gaggaaaaga      600
aaccaacagg   gattgcccta   gtaacggcga    gtgaagcggc    aacagctcaa    atttgaaatc      660
tggctctttt   agagtccgag   ttgtaatttg    cagagggcgc    tttggctttg    gcagcggtcc      720
aagttccttg   gaacaggacg   tcacagaggg    tgagaatccc    gtacgtggtc    gctggctatt      780
gccgtgtaaa   gccccttcga   cgagtcgagt    tgtttgggaa    tgcagctcta    aatgggaggt      840
acatttcttc   taaagctaaa   tattggccag    agaccgatag    cgcacaagta    gagtgatcga      900
aagatgaaaa   gcactttgga   aagagagtca    aacagcacgt    gaaattgttg    aaagggaagc      960
gcttgcagcc   agacttgctt   acagttgctc    atccgggttt    ttacccggtg    cactcttctg     1020
taggcaggcc   agcatcagtt   tgggcggtag    gataaaggtc    tctgtcacgt    acctcctttc     1080
ggggaggcct   tata                                                                  1094
```

```
<210> SEQ ID NO 94
<211> LENGTH: 1005
<212> TYPE: DNA
<213> ORGANISM: Alternaria alternata

<400> SEQUENCE: 94
tcactgtcac   gttcattaag   taacaaggac    ttcttacata    tttaaagttt    gagaataggt       60
gaaggttgtt   tcaaccccca   ggcctctaat    cattcgcttt    acctcataaa    actgaatacg      120
ttactgctat   cctgagggaa   acttcggcag    gaaccagcta    ctagatagtt    cgattagtct      180
ttcgccccta   tgcccaaatt   tgacgatcga    tttgcacgtc    agaaccgctg    cgagcctcca      240
```

```
ccagagtttc ctctggcttc accctattca agcatagttc accatctttc gggtcccaac      300
agccatgctc ttactcaaat ccttccgaag acatcaggat cggtcgatgg tgcacccttg      360
cgggttccca cctccgttca ctttcattac gcgctcgggc ttgacaccca aacactcgca      420
tagatgttag actccttggt ccgtgtttca agacgggccg cttacagcca ttacgccagc      480
atcctagcag atgcgcggac ctcagtccag gctggtagta tgtcgtctcc cctataaggc      540
ctccccgaaa ggaggtacgt gacagagacc tttatcctac cgcccaaact gatgctggcc      600
tgcctacaga agagtgcacc gggtaaaaac ccggatgagc aactgtaagc aagtctggct      660
gcaagcgctt ccctttcaac aatttcacgt gctgtttgac tctctttcca aagtgctttt      720
catctttcga tcactctact tgtgcgctat cggtctctgg ccaatattta gctttagaag      780
aaatgtacct cccatttaga gctgcattcc caaacaactc gactcgtcga aggggcttta      840
cacggcaata gccagcgacc acgtacggga ttctcaccct ctgtgacgtc ctgttccaag      900
gaacttggac cgctgccaaa gccaaagcgc cctctgcaaa ttacaactcg gactctaaaa      960
gagccagatt tcaaatttga gctgttgccg cttcactcgc cgtta                     1005

<210> SEQ ID NO 95
<211> LENGTH: 1012
<212> TYPE: DNA
<213> ORGANISM: Candida glabrata
<220> FEATURE:
<221> NAME/KEY: misc_feature
<222> LOCATION: (654)..(655)
<223> OTHER INFORMATION: n is a, c, g, or t
<220> FEATURE:
<221> NAME/KEY: misc_feature
<222> LOCATION: (815)..(815)
<223> OTHER INFORMATION: n is a, c, g, or t
<220> FEATURE:
<221> NAME/KEY: misc_feature
<222> LOCATION: (824)..(824)
<223> OTHER INFORMATION: n is a, c, g, or t
<220> FEATURE:
<221> NAME/KEY: misc_feature
<222> LOCATION: (829)..(829)
<223> OTHER INFORMATION: n is a, c, g, or t

<400> SEQUENCE: 95
ggaagtaaaa gtcgtaacaa ggtttccgta ggtgaacctg cggaaggatc attaaagaaa       60
tttaattgat ttgtctgagc tcggagagag acatctctgg ggaggaccag tgtagacact      120
caggaggctc ctaaaatatt ttctctgctg tgaatgctat ttctcctgcc tgcgcttaag      180
tgcgcggttg gtgggtgttc tgcagtgggg ggagggagcc gacaaagacc tgggagtgtg      240
cgtggatctc tctattccaa aggaggtgtt ttatcacacg actcgacact ttctaattac      300
tacacacagt ggagtttact ttactactat tcttttgttc gttgggggaa cgctctcttt      360 cggggggag ttctcccagt ggatgcaaac acaaacaaat atttttttaa actaattcag       420
tcaacacaag atttcttta gtagaaaaca acttcaaaac tttcaacaat ggatctcttg       480
gttctcgcat cgatgaagaa cgcagcgaaa tgcgatacgt aatgtgaatt gcagaattcc      540
gtgaatcatc gaatctttga acgcacattg cgccctctgg tattccgggg gcatgcctg      600 tttgagcgtc atttccttct caaacacatt gtgtttggta gtgagtgata ctcnngtttt      660
tgagttaact tgaaattgta ggccatatca gtatgtggga cacgagcgca agcttctcta      720
ttaatctgct gctcgtttgc gcgagcgcg ggggttaata ctgtattagg ttttaccaac      780
tcggtgttga tctagggagg gataagtgag tgttnttgtg cgtngctgng gcagacagac      840
```

```
gtctttaagt ttgacctcaa atcaggtagg gttacccgct gaacttaagc atatcaataa    900
gcggaggaaa agaaaccaac tgggattgcc ttagtaacgg cgagtgaagc ggcaaaagct    960
caaatttgaa atctggtacc tttggtgccc gagttgtaat ttggagagta cc           1012

<210> SEQ ID NO 96
<211> LENGTH: 994
<212> TYPE: DNA
<213> ORGANISM: Candida glabrata

<400> SEQUENCE: 96
aatgtccacg ttcaattaag caacaaggac ttcttacata tttaaagttt gagaataggt     60
caaggtcatt tcaaccccgg tacctctaat cattcgcttt acctcataaa actgatacga    120
gcttctgcta tcctgaggga aacttcggca ggaaccagct actagatggt tcgattagtc    180
tttcgcccct atacccaaat tcgacgatcg atttgcacgt cagaaccgct acgagcctcc    240
accagagttt cctctggctt caccctattc aggcatagtt caccatcttt cgggtcccaa    300
cagctatgct cttactcaaa tccatccgaa gacatcagga tcggtcgatt gtgcaccccc    360
caggtggagg gccccaacct acgttcactt tcattacgcg tacgggttta acacccaaac    420
actcgcatag acgttagact ccttggtccg tgtttcaaga cgggcggcat ataaccatta    480
tgccagcatc ctagataaca agtatcgcag tcctcggtcc cgactggccg tattccccag    540
ggctataaca ctctacaccg aggcgcagag ccacattccc taggtttttt ccggccgcca    600
aaaccgatgc tggcccagtg agctgcgaga gtcccaagcc cacgagaggc aaggggcgca    660
aaacaccatg tctgatcaaa tgcccttccc tttcaacaat ttcacgtact ttttcactct    720
cttttcaaag ttcttttcat ctttccatca ctgtacttgt tcgctatcgg tctctcgcct    780
gtatttagct ttagatggaa tttaccaccc acttagagct gcattcccaa acaactcgac    840
tcttcgagca cccttacaa agaactgaca ccctcgccac acgggattct cacccctcat     900
gacgtcctgt tccaaggaac ataggcaaag tacagtccca aagtggtact ctccaaatta    960
caactcgggc accaaaggta ccagatttca aatt                                994

<210> SEQ ID NO 97
<211> LENGTH: 1013
<212> TYPE: DNA
<213> ORGANISM: Phoma glomerata

<400> SEQUENCE: 97
ctgcggaagg atcattacct agagttgtag gctttgcctg ctatctctta cccatgtctt     60
ttaagtacct tacgtttcct cggcgggtcc gcccgccgat tggacaattt aaaccatttg    120
cagttgcaat cagcgtctga aaaacttaa tagttacaac tttcaacaac ggatctcttg    180
gttctggcat cgatgaagaa cgcagcgaaa tgcgataagt agtgtgaatt gcagaattca    240
gtgaatcatc gaatctttga acgcacattg cgccccttgg tattccatgg ggcatgcctg    300
ttcgagcgtc atttgtacct tcaagctctg cttggtgttg ggtgtttgtc tcgcctctgc    360
gtgtagactc gcctcaaaac aattggcagc cggcgtattg atttcggagc gcagtacatc    420
tcgcgctttg cactcataac gacgacgtcc aaaagtacat ttttacactc ttgacctcgg    480
atcaggtagg gataccccgct gaacttaagc atatcaataa gcggaggaaa agaaaccaac    540
agggattgcc ctagtaacgg cgagtgaagc ggcaacagct caaatttgaa atctggcgtc    600
tttggcgtcc gagttgtaat ttgcagaggg cgctttggca ttggcagcgg tccaagttcc    660
ttggaacagg acgtcacaga gggtgagaat cccgtacgtg gtcgctagcc tttaccgtgt    720
```

-continued

```
aaagcccctt cgacgagtcg agttgtttgg gaatgcagct ctaaatggga ggtaaatttc      780
ttctaaagct aaatactggc cagagaccga tagcgcacaa gtagagtgat cgaaagatga      840
aaagcacttt ggaaagagag ttaaaaagca cgtgaaattg ttgaaaggga agcgcttgca      900
gccagacttg cctgtagttg ctcatccggg tttctacccg gtgcactctt ctataggcag      960
gccagcatca gtttgggcgg ttggataaag gtctctgtca tgtacctcct ttc           1013
```

<210> SEQ ID NO 98
<211> LENGTH: 973
<212> TYPE: DNA
<213> ORGANISM: Phoma glomerata

<400> SEQUENCE: 98

```
tcactgtcac gttcatcaag taacaaggac ttcttacata tttaaagttt gagaataggt       60
gaaggttgtt tcaaccccca ggcctctaat cattcgcttt acctcataaa actgaaaacg      120
ttactgctat cctgagggaa acttcggcag gaaccagcta ctagatagtt cgattagtct      180 ttcgcccta tgcccaaatt tgacgatcga tttgcacgtc agaaccgctg cgagcctcca      240
ccagagtttc ctctggcttc accctattca agcatagttc accatctttc gggtcccaac      300
agctatgctc ttactcaaat ccatccgaag acatcaggat cggtcgatgg tgcaccccga      360
aaggttccca cctccgttca ctttcattac gcgctcgggc ttgacaccca aacactcgca      420
tagatgttag actccttggt ccgtgtttca agacgggccg cttacagcca ttacgccagc      480
atcctagcag atgcgcggac ctcagtccag gctggttgca tgtcgtctcc cctataagtt      540
ctccccgaaa ggaggtacat gacagagacc tttatccaac cgcccaaact gatgctggcc      600
tgcctataga agagtgcacc gggtagaaac ccggatgagc aactacaggc aagtctggct      660
gcaagcgctt ccctttcaac aatttcacgt gctttttaac tctctttcca aagtgctttt      720
catctttcga tcactctact tgtgcgctat cggtctctgg ccagtattta gctttagaag      780
aaatttacct cccatttaga gctgcattcc caaacaactc gactcgtcga aggggcttta      840
cacggtaaag gctagcgacc acgtacggga ttctcaccct ctgtgacgtc ctgttccaag      900
gaacttggac cgctgccaat gccaaagcgc cctctgcaaa ttacaactcg gacgccaaag      960
acgccagatt tca                                                        973
```

<210> SEQ ID NO 99
<211> LENGTH: 1041
<212> TYPE: DNA
<213> ORGANISM: Aureobasidium pullulans
<220> FEATURE:
<221> NAME/KEY: misc_feature
<222> LOCATION: (66)..(66)
<223> OTHER INFORMATION: n is a, c, g, or t
<220> FEATURE:
<221> NAME/KEY: misc_feature
<222> LOCATION: (75)..(75)
<223> OTHER INFORMATION: n is a, c, g, or t
<220> FEATURE:
<221> NAME/KEY: misc_feature
<222> LOCATION: (148)..(148)
<223> OTHER INFORMATION: n is a, c, g, or t
<220> FEATURE:
<221> NAME/KEY: misc_feature
<222> LOCATION: (534)..(534)
<223> OTHER INFORMATION: n is a, c, g, or t
<220> FEATURE:
<221> NAME/KEY: misc_feature
<222> LOCATION: (546)..(546)
<223> OTHER INFORMATION: n is a, c, g, or t
<220> FEATURE:

<220> FEATURE:
<221> NAME/KEY: misc_feature
<222> LOCATION: (563)..(563)
<223> OTHER INFORMATION: n is a, c, g, or t
<220> FEATURE:
<221> NAME/KEY: misc_feature
<222> LOCATION: (568)..(568)
<223> OTHER INFORMATION: n is a, c, g, or t
<220> FEATURE:
<221> NAME/KEY: misc_feature
<222> LOCATION: (701)..(701)
<223> OTHER INFORMATION: n is a, c, g, or t

<400> SEQUENCE: 99

```
ggaagtaaaa gtcgtaacaa ggtttccgta ggtgaacctg cggaaggatc attaacgagc      60
aagggngcga aagcnccga acctccaacc ctctgtcgtt ataactacca acgttgcttt     120
ggcgggaccg cgagggtcct cccgagcngc gccagtctcc ggacaggcga gcgcccgcca     180
gagtccaacc aaactcttgt tttcaaacca gccgtctgag tacaaatttt taatataatt     240
aaaactttca caacggatc tcttggttct cgcatcgatg aagaacgcag cgaaatgcga     300
taagtaatgt gaattgcaga attcagtgaa tcatcgaatc tttgaacgca cattgcgccc     360
cttggtattc cgaggggcat gcctgttcga gcgtcattac aacactcaag cactgcttgg     420
tattgggcac cccgtccgcc gcaaggcggg cgtgcctcga agacctcggc ggggtttctc     480
caacttcggg cgtagtagag ttaaatcaaa acgtctcata gctttgggg gggncctcca     540
tgccgnttaa acacccttt atnattcnat gttgacctcg gatcaggtag ggataccgc     600
tgaacttaag catatcaata agcggaggaa aagaaaccaa cagggattgc cctagtaacg     660
gcgagtgaag cggcaatagc tcaaatttga aagctggcct nctggtccgc attgtaattt     720
gtagaggatg cttttaggca gccgccggtc taagttcctt ggaacaggac gtcatagagg     780
gtgagaatcc cgtatgtgac cggctcaggc accttctgta aagctccttc gacgagtcga     840
gttgtttggg aatgcagctc taaatgggag gtaaatttct tctaaagcta aataccggcg     900
agagaccgat agcgcacaag tagagtgatc gaaagatgaa aagcactttg gaaagagagt     960
taaaaagcac gtgaaattgt tgaaagggaa gcgcttgcaa tcagacttgg acttggctgt    1020
tcaaccggtc ttctgaccgg c                                              1041
```

<210> SEQ ID NO 100
<211> LENGTH: 996
<212> TYPE: DNA
<213> ORGANISM: Aureobasidium pullulans
<220> FEATURE:
<221> NAME/KEY: misc_feature
<222> LOCATION: (961)..(961)
<223> OTHER INFORMATION: n is a, c, g, or t

<400> SEQUENCE: 100

```
catgtccacg ttcactaagt aacaaggact tcttacatat ttaaagtttg agaataggtt      60
aaggatgttt catccccaag gcctctaatc attcgcttta cctcataaaa ctgaaaacgt     120
tactgctatc ctgagggaaa cttcggcagg aaccagctac tagatggttc gattagtctt     180
tcgcccctat acccaaattt gacgatcgat ttgcacgtca gaaccgctgc gagcctccac     240
cagagttttcc tctggcttca ccctattcag gcatagttca ccatctttcg ggtcccaaca     300
gctatgctct tactcaaatc catccgaaga catcaggatc ggtcgatggt gcgcccttgc     360
gggttcccac ctccgttcac tttcattacg cgtaagggtt tgacacccta acactcgcat     420
agatgttaga ctccttggtc cgtgtttcaa gacgggccgc ttacaaccat tacgccagca     480
tcctagccga agcgcggacc tcagtcccgg ctggccgtat tacaccccgg gctataacac     540
```

```
tgcccccgaa gaggcagcta cattcccggg gcctttatcc ggccgccgaa actgatgctg    600
gcctggacaa gactgagtgg gccggtcaga agaccggttg aacagccaag tccaagtctg    660
attgcaagcg cttccctttc aacaatttca cgtgctttt aactctcttt ccaaagtgct    720
tttcatcttt cgatcactct acttgtgcgc tatcggtctc tcgccggtat ttagctttag    780
aagaaattta cctcccattt agagctgcat cccaaacaa ctcgactcgt cgaaggagct    840
ttacagaagg tgcctgagcc ggtcacatac gggattctca ccctctatga cgtcctgttc    900
caaggaactt agaccggcgg ctgcctaaaa gcatcctcta caaattacaa tgcggaccag    960
naggccagct ttcaaatttg agctattgcc gcttca                              996

<210> SEQ ID NO 101
<211> LENGTH: 964
<212> TYPE: DNA
<213> ORGANISM: Epicoccum nigrum

<400> SEQUENCE: 101
ttccgtaggt gaacctgcgg aaggatcatt acctagagtt tgtggacttc ggtctgctac     60
ctcttaccca tgtcttttga gtaccttcgt ttcctcggcg ggtccgcccg ccggttggac    120
aacattcaaa cccctttgcag ttgcaatcag cgtctgaaaa acttaatag ttacaacttt    180 caacaacgga tctcttggtt ctggcatcga tgaagaacgc agcgaaatgc gataagtagt    240
gtgaattgca gaattcagtg aatcatcgaa tctttgaacg cacattgcgc cccttggtat    300
tccatggggc atgcctgttc gagcgtcatt tgtaccttca agctctgctt ggtgttgggt    360
gttttgtctc gcctccgcgc gcagactcgc cttaaaacaa ttggcagccg gcgtattgat    420
ttcggagcgc agtacatctc gcgctttgca ctcataacga cgacgtccaa aagtacatt     480 ttacactctt gacctcggat caggtaggga tacccgctga acttaagcat atcaataagc    540
ggaggaaaag aaaccaacag ggattgccct agtaacggcg agtgaagcgg caacagctca    600
aatttgaaat ctggcgtctt tggcgtccga gttgtaattt gcagagggcg ctttggcatt    660
ggcagcggtc caagttcctt ggaacaggac gtcacagagg gtgagaatcc cgtacgtggt    720
cgctagcctt taccgtgtaa agccccttcg acgagtcgag ttgtttggga atgcagctct    780
aaatgggagg taaatttctt ctaaagctaa atactggcca gagaccgata gcgcacaagt    840
agagtgatcg aaagatgaaa agcactttgg aaagagagt aaaaagcacg tgaaattgtt    900 gaagggaag cgcttgcagc cagacttgcc tgtagttgct catccgggtt ctacccggt     960 gcac                                                                 964

<210> SEQ ID NO 102
<211> LENGTH: 986
<212> TYPE: DNA
<213> ORGANISM: Epicoccum nigrum

<400> SEQUENCE: 102
actgtcacgt tcaattaagt aacaaggact tcttacatat ttaaagtttg agaataggtg     60
aaggttgttt caaccccag gcctctaatc attcgcttta cctcataaaa ctgaaaacgt     120
tactgctatc ctgagggaaa cttcggcagg aaccagctac tagatagttc gattagtctt    180
tcgcccctat gcccaaattt gacgatcgat ttgcacgtca gaaccgctgc gagcctccac    240
cagagtttcc tctggcttca ccctattcaa gcatagttca ccatctttcg ggtcccaaca    300
gctatgctct tactcaaatc catccgaaga catcaggatc ggtcgatggt gcaccccgaa    360
```

```
aggttcccac ctccgttcac tttcattacg cgctcgggct tgacacccaa acactcgcat      420
agatgttaga ctccttggtc cgtgtttcaa gacgggccgc ttacagccat tacgccagca      480
tcctagcaga tgcgcggacc tcagtccagg ctggttgcat gtcgtctccc ctataagatc      540
tccccgaagg gaggtacatg acagagacct ttatccaacc gcccaaactg atgctggcct      600
gcccgtagaa gagtgcaccg ggtagaaacc cggatgagca actacaggca gtctggctg       660 caagcgcttc cctttcaaca atttcacgtg ctttttaact ctctttccaa agtgcttttc      720
atctttcgat cactctactt gtgcgctatc ggtctctggc cagtatttag ctttagaaga      780
aatttacctc ccatttagag ctgcattccc aaacaactcg actcgtcgaa ggggctttac      840
acggtaaagg ctagcgacca cgtacgggat tctcaccctc tgtgacgtcc tgttccaagg      900
aacttggacc gctgccaatg ccaaagcgcc ctctgcaaat tacaactcgg acgccaaaga      960
cgccagattt caaatttgag ctgttg                                           986

<210> SEQ ID NO 103
<211> LENGTH: 1043
<212> TYPE: DNA
<213> ORGANISM: Acremonium strictum
<220> FEATURE:
<221> NAME/KEY: misc_feature
<222> LOCATION: (103)..(103)
<223> OTHER INFORMATION: n is a, c, g, or t
<220> FEATURE:
<221> NAME/KEY: misc_feature
<222> LOCATION: (113)..(113)
<223> OTHER INFORMATION: n is a, c, g, or t
<220> FEATURE:
<221> NAME/KEY: misc_feature
<222> LOCATION: (154)..(154)
<223> OTHER INFORMATION: n is a, c, g, or t
<220> FEATURE:
<221> NAME/KEY: misc_feature
<222> LOCATION: (369)..(369)
<223> OTHER INFORMATION: n is a, c, g, or t
<220> FEATURE:
<221> NAME/KEY: misc_feature
<222> LOCATION: (382)..(384)
<223> OTHER INFORMATION: n is a, c, g, or t
<220> FEATURE:
<221> NAME/KEY: misc_feature
<222> LOCATION: (411)..(411)
<223> OTHER INFORMATION: n is a, c, g, or t
<220> FEATURE:
<221> NAME/KEY: misc_feature
<222> LOCATION: (476)..(476)
<223> OTHER INFORMATION: n is a, c, g, or t

<400> SEQUENCE: 103
tccgtaggtg aaccagcgga gggatcatta ccagagtgcc ctaggctctc caacccattg       60
tgaacatacc tatcgttccc tcggcgggct cagcgcgcgg tgncctccgg gcntccgggc      120
gtccgccggg gacaaccaaa ctctgatttt attngtgaat ctctgagggg cgaaagcccg      180
aaaacaaaat gaatcaaaac tttcaacaac ggatctcttg gctctggcat cgatgaagaa      240
cgcagcgaaa tgcgataagt aatgtgaatt gcagaattca gtgaatcatc gaatctttga      300
acgcacattg cgcccgccgg cactccggcg ggcatgcctg tccgagcgtc atttcaaccc      360
tcaggaccnc cctttcgggg gnnnggacct ggtgctgggg atcagcggcc ntccgggccc      420
ctgtccccca aattgagtgg cggtcgcgcc gcagcctccc ctgcgtagta gcacanccctc     480 gcaccggaga gcggctcggc cacgccgtga acccccaat tttttaaggt tgacctcgga      540
tcaggtagga atacccgctg aacttaagca tatcaataag cggaggaaaa gaaaccaaca      600
gggattgcct cagtaacggc gagtgaagcg gcaacagctc aaatttgaaa tctggccgca      660
```

```
aggtccgagt tgtaatttgt agaggatgct tttggcgagg tgccttccga gttccctgga    720
acgggacgcc atagagggtg agagccccgt acggtaggac caccaagcct ctgtaaagct    780
ccttcgacga gtcgagtagt ttgggaatgc tgctctaaat gggaggtgta cgtcttctaa    840
agctaaatac cggccagaga ccgatagcgc acaagtagag tgatcgaaag atgaaaagca    900
ctttgaaaag agggttaaaa agtacgtgaa attgttgaaa gggaagcatt catgaccaga    960
cttgggcttg gttgaacatc cggcgttctc gccggtgcac tctgccagtc caggccagca   1020
tcagtttgcc ccgggggata aag                                           1043
```

<210> SEQ ID NO 104
<211> LENGTH: 1033
<212> TYPE: DNA
<213> ORGANISM: Acremonium strictum

<400> SEQUENCE: 104

```
tcgatgccca cgttcaatta agtaacaaga gcttcttaca tatttaaagt ttgagaatgg     60
atgaaggcta aatagcgccc cctggtccct aatcattcgc tttacctcat aaaactgagt    120
tcaacactgc tatcctgagg gaaacttcgg cggaaaccag ctactagaag gttcgattag    180
tctttcgccc ccatgcccat atttgacgat cgatttgcac gtcagaaccg ctgcgagcct    240
ccaccagagt ttcctctggc ttcaccctat acaggcatag ttcaccttct ttcgggtccg    300
gccccgtatg ctcttactca aatccatccg agaacatcag gatcggtcgg tgatgcgccg    360
aagctctcac ctacgttcac tttcattacg cgtaggggtt tgacaccgga acactcgcat    420
acgaagacga ctccttggtc cgtgtttcaa gacgggtcat tgatgaccat tacgccagca    480
tccgtgccga agcgcgttcc tcagtccgcc ccagggcatt acacgacggg ctataacact    540
ccccgaaggg agccacattc ccgccgcctt tatccccgg ggcaaactga tgctggcctg    600
gactggcaga gtgcaccggc gagaacgccg gatgttcaac caagcccaag tctggtcatg    660
aatgcttccc tttcaacaat ttcacgtact tttttaaccct cttttcaaag tgcttttcat    720
ctttcgatca ctctacttgt gcgctatcgg tctctggccg gtatttagct ttagaagacg    780
tacacctccc atttagagca gcattcccaa actactcgac tcgtcgaagg agctttacag    840
aggcttggtg gtcctaccgt acggggctct cacctctat ggcgtcccgt tccagggaac     900
tcggaaggca cctcgccaaa agcatcctct acaaattaca actcggacct tgcggccaga    960
tttcaaattt gagctgttgc cgcttcactc gccgttactg aggcaatccc tgttggtttc   1020
ttttcctccg ctt                                                      1033
```

<210> SEQ ID NO 105
<211> LENGTH: 1048
<212> TYPE: DNA
<213> ORGANISM: Geotrichum candidum

<400> SEQUENCE: 105

```
ccttccgtat ggtgaacctg cggaaggatc attatgaatt aaaaatattt gtgaatttac     60
cacaacaaac aacaatacta tagtcaaata cataaataat taaaactttt aacaatggat    120
ctcttggttc tcgtatcgat gaagaacgca gcgaaacgcg atatttcttg tgaattgcag    180
aagtgaatca tcagttttttg aacgcacatt gcactttggg gtatccccca agtatactt    240 gtttgagcgt tgtttctctc ttggaattgc tttgctcttc taaatttcg aatcaaattc    300 gtttgaaaaa caacactatt caacctcaga tcaagtagga ttacccgctg aacttaagca    360
```

```
tatcaataag cggaggaaaa gaaaccaaca gggattgcct tagtaacggc gagtgaagcg      420
gcaaaagctc aaatttgaaa tcggcccca gtcgagttg taatttgtag attgtatctt        480
gagagcggat taaagtctgt tggaacacag cgccttagag ggtgacagcc ccgtaaaatc      540
tattctcatt gtaagatact ttcgaagagt cgagttgttt gggaatgcag ctctaagtgg     600
gaggtaaatt ccttctaaag ctaaatattg acgagagacc gatagcgaac aagtactgtg     660
aaggaaagat gaaaagcact ttgaaaagag agtgaaaaag tacgtgaaat tgttaaaagg     720
gaagggtatt gaatcagact tggtgctgtt gttcaactgt gtctcggcac agtgtactca     780
gcagtactag gccaaggtgg ggtgtttggg agtgaaaaag aagttggaac gtaactcttc     840
ggagtgttat agcctacttt catagctcct caggcgcctc aggactgcgc ttcggcaagg     900
accttggcat aatgattcta taccgcccgt cttgaaacac ggaccaagga gtctaacgtc     960
tatgcgagtg tttgggtgta aaacccgtac gcgtaatgaa agtgaacgta gataggagca    1020
gtaatgcgca ctatcgacga tcctgatg                                       1048

<210> SEQ ID NO 106
<211> LENGTH: 1014
<212> TYPE: DNA
<213> ORGANISM: Geotrichum candidum

<400> SEQUENCE: 106
atgtccacgt tcaattaaga aacaaggact tcttacatat ttaaagtttg agaataggtt      60
aaggtcacat agaccccagt acctctaatc attcgcttta cctcataaaa ctgatacgag     120
cttctgctat cctgagggaa acttcggcag gaaccagcta ctagatggtt cgattagtct     180 ttcgcccta tacccaaatt cgacgatcga tttgcacgtc agaaccgcta cgagcctcca     240
ccagagtttc ctctggcttc accctattca ggcatagttc accatctttc gggtcccaac     300
agctatgctc ttactcaaat ccatctgaaa acatcaggat cgtcgatagt gcgcattact     360
gctcctatct acgttcactt tcattacgcg tacgggtttt acacccaaac actcgcatag     420
acgttagact ccttggtccg tgtttcaaga cgggcggtat agaatcatta tgccaaggtc     480
cttgccgaag cgcagtcctg aggcgcctga ggagctatga agtaggcta taacactccg      540 aagagttacg ttcaacttc ttttcactc ccaaacaccc caccttggcc tagtactgct       600
gagtacactg tgccgagaca cagttgaaca acagcaccaa gtctgattca ataccttcc     660 ctttaacaa tttcacgtac ttttcactc tcttttcaaa gtgcttttca tctttccttc      720
acagtacttg ttcgctatcg gtctctcgtc aatatttagc tttagaagga atttacctcc    780
cacttagagc tgcattccca aacaactcga ctcttcgaaa gtatcttaca atgagaatag    840
attttacggg gctgtcaccc tctaaggcgc tgtgttccaa cagactttaa tccgctctca    900
agatacaatc tacaaattac aactcgacct gggggccgat ttcaaatttg agcttttgcc    960
gcttcactcg ccgttactaa ggcaatccct gttggtttct tttcctccgc ttat         1014

<210> SEQ ID NO 107
<211> LENGTH: 980
<212> TYPE: DNA
<213> ORGANISM: Aspergillus fumigatus

<400> SEQUENCE: 107
ttccgtaggt gaacctgcgg aaggatcatt accgagtgag ggccctctgg gtccaacctc      60
ccacccgtgt ctatcgtacc ttgttgcttc ggcgggcccg ccgtttcgac ggccgccggg     120
gaggccttgc gcccccgggc ccgcgcccgc cgaagacccc aacatgaacg ctgttctgaa     180
```

```
agtatgcagt ctgagttgat tatcgtaatc agttaaaact ttcaacaacg gatctcttgg      240
ttccggcatc gatgaagaac gcagcgaaat gcgataagta atgtgaattg cagaattcag      300
tgaatcatcg agtctttgaa cgcacattgc gccccctggt attccggggg gcatgcctgt      360
ccgagcgtca ttgctgccct caagcacggc ttgtgtgttg ggcccccgtc ccctctcccc      420
gggggacggg cccgaaaggc agcggcggca ccgcgtccgg tcctcgagcg tatgggcttt      480
tgtcacctgc tctgtaggcc cggccggcgc cagccgacac ccaactttat ttttctaagg      540
ttgacctcgg atcaggtagg gatacccgct gaacttaagc atatcaataa gcggaggaaa      600
agaaaccaac agggattgcc tcagtaacgg cgagtgaagc ggcaagagct caaatttgaa      660
agctggcccc ttcggggtcc gcgttgtaat ttgcagagga tgcttcgggt gcagccccg       720 tctaagtgcc ctggaacggg ccgtcataga gggtgagaat cccgtctggg acggggtgtc      780
tgcgtccgtg tgaagctcct tcgacgagtc gagttgtttg ggaatgcagc tctaaatggg      840
tggtaaattt catctaaagc taaatactgg ccggagaccg atagcgcaca agtagagtga      900
tcgaaagatg aaaagcactt tgaaaagaga gttaaacagc acgtgaaatt gttgaaaggg      960
aagcgtttgc gaccagactc                                                 980

<210> SEQ ID NO 108
<211> LENGTH: 1002
<212> TYPE: DNA
<213> ORGANISM: Aspergillus fumigatus

<400> SEQUENCE: 108
gcaacaagcg cttcttacat atttaaagtt tgagaatagg ttaaggttgt ttcaaccccca     60 aggcctctaa tcattcgctt tacctcataa aactgatccg cgttactgct atcctgaggg     120
aaacttcggc aggaaccagc tactagatgg ttcgattagt cttccgcccc tatacccaaa    180
tttgacgatc gatttgcacg tcagaccgct gcgagcctcc accagagttt cctctggctt     240
cgccctattc aggcatagtt caccatcttt cgggtcccca cagctacgct cgtactcaaa    300
tccatccgaa gacatcagga tcggtcgatg gtgcgcccg cgaggggct cccacctccg      360 ttcgctttca ctgcgcgtac gggtttgaca cccgaacact cgcgtagatg ttagactcct     420
tggtccgtgt ttcaagacgg gtcatttacg accattacgc cagcgtccga gccgaacgcg    480
ttcctcggtc caggcaggcc gcattgcacc ctcggctata agacaccccg agaggtgata    540
cattccgagg gcctttgacc ggccgcccaa accgacgctg gcccgcccac ggggaagtac    600
accggcacga atgccggctg aaccccgcgg gcgagtctgg tcgcaaacgc ttccctttca    660
acaatttcac gtgctgtttta actctctttt caaagtgctt ttcatctttc gatcactcta   720
cttgtgcgct atcggtctcc ggccagtatt tagcttaga tgaaatttac cacccattta    780
gagctgcatt cccaaacaac tcgactcgtc gaaggagctt cacacggacg cagacacccc    840
gtcccagacg ggattctcac cctctatgac ggcccgttcc aggcacttac acgggggct    900 gcacccgaag catcctctgc aaattacaac gcggaccccg aaggggccag ctttcaaatt    960
tgagctcttg ccgcttcact cgccgttact gaggcaatcc ct                        1002

<210> SEQ ID NO 109
<211> LENGTH: 20
<212> TYPE: DNA
<213> ORGANISM: Acremonium strictum

<400> SEQUENCE: 109
```

```
agggaagcat tcatgaccag                                              20

<210> SEQ ID NO 110
<211> LENGTH: 20
<212> TYPE: DNA
<213> ORGANISM: Acremonium strictum

<400> SEQUENCE: 110
gcttggttga acatccggcg                                              20

<210> SEQ ID NO 111
<211> LENGTH: 20
<212> TYPE: DNA
<213> ORGANISM: Alternaria alternata

<400> SEQUENCE: 111
ccgggttttt acccggtgca                                              20

<210> SEQ ID NO 112
<211> LENGTH: 20
<212> TYPE: DNA
<213> ORGANISM: Aspergillus candidus

<400> SEQUENCE: 112
gccggtcagc ggctcccgga                                              20

<210> SEQ ID NO 113
<211> LENGTH: 20
<212> TYPE: DNA
<213> ORGANISM: Aspergillus flavus

<400> SEQUENCE: 113
actcgcctcc agggttcagc                                              20

<210> SEQ ID NO 114
<211> LENGTH: 20
<212> TYPE: DNA
<213> ORGANISM: Aspergillus flavus

<400> SEQUENCE: 114
tccggggcac cttatagccg                                              20

<210> SEQ ID NO 115
<211> LENGTH: 25
<212> TYPE: DNA
<213> ORGANISM: Aspergillus fumigatus

<400> SEQUENCE: 115
ggaatgtatc acctctcggg gtgtc                                        25

<210> SEQ ID NO 116
<211> LENGTH: 20
<212> TYPE: DNA
<213> ORGANISM: Aspergillus ochraceus

<400> SEQUENCE: 116
ggaatgtagc acccttcggg                                              20

<210> SEQ ID NO 117
<211> LENGTH: 20
<212> TYPE: DNA
<213> ORGANISM: Aspergillus ochraceus

<400> SEQUENCE: 117
```

-continued

```
cttcggggtg ccttatagcc                                              20

<210> SEQ ID NO 118
<211> LENGTH: 20
<212> TYPE: DNA
<213> ORGANISM: Aspergillus penicillioides

<400> SEQUENCE: 118
aacgcccctc cggggcgtc                                               20

<210> SEQ ID NO 119
<211> LENGTH: 21
<212> TYPE: DNA
<213> ORGANISM: Aspergillus restrictus

<400> SEQUENCE: 119
gctctggaat gggccatcag a                                            21

<210> SEQ ID NO 120
<211> LENGTH: 21
<212> TYPE: DNA
<213> ORGANISM: Aspergillus restrictus

<400> SEQUENCE: 120
ggaatgtaac acctctcggg g                                            21

<210> SEQ ID NO 121
<211> LENGTH: 20
<212> TYPE: DNA
<213> ORGANISM: Aspergillus sclerotiorum

<400> SEQUENCE: 121
agtgccccta cggggggcacc                                             20

<210> SEQ ID NO 122
<211> LENGTH: 20
<212> TYPE: DNA
<213> ORGANISM: Aspergillus sydowii

<400> SEQUENCE: 122
accatttttc ttcaggttga                                              20

<210> SEQ ID NO 123
<211> LENGTH: 20
<212> TYPE: DNA
<213> ORGANISM: Aspergillus terreus

<400> SEQUENCE: 123
tcagccgggc ttcggcccgg                                              20

<210> SEQ ID NO 124
<211> LENGTH: 20
<212> TYPE: DNA
<213> ORGANISM: Aspergillus terreus

<400> SEQUENCE: 124
gggcttcggc ccggtgtact                                              20

<210> SEQ ID NO 125
<211> LENGTH: 20
<212> TYPE: DNA
<213> ORGANISM: Aspergillus ustus
```

```
<400> SEQUENCE: 125
aggaatgtgt cgccctccgg                                              20

<210> SEQ ID NO 126
<211> LENGTH: 20
<212> TYPE: DNA
<213> ORGANISM: Aspergillus ustus

<400> SEQUENCE: 126
tcgccctccg gggcgtctta                                              20

<210> SEQ ID NO 127
<211> LENGTH: 20
<212> TYPE: DNA
<213> ORGANISM: Aspergillus versicolor

<400> SEQUENCE: 127
gcgtcggttc gggcggccgg                                              20

<210> SEQ ID NO 128
<211> LENGTH: 20
<212> TYPE: DNA
<213> ORGANISM: Aspergillus versicolor

<400> SEQUENCE: 128
gtaatggtca caaacgaccc                                              20

<210> SEQ ID NO 129
<211> LENGTH: 20
<212> TYPE: DNA
<213> ORGANISM: Aurobasidium pullulans

<400> SEQUENCE: 129
gctggcctct ggtccgcatt                                              20

<210> SEQ ID NO 130
<211> LENGTH: 20
<212> TYPE: DNA
<213> ORGANISM: Aurobasidium pullulans

<400> SEQUENCE: 130
accggctcag gcaccttctg                                              20

<210> SEQ ID NO 131
<211> LENGTH: 20
<212> TYPE: DNA
<213> ORGANISM: Aurobasidium pullulans

<400> SEQUENCE: 131
gcccactcag tcttgtccag                                              20

<210> SEQ ID NO 132
<211> LENGTH: 20
<212> TYPE: DNA
<213> ORGANISM: Candida glabrata

<400> SEQUENCE: 132
gatacttgtt atctaggatg                                              20

<210> SEQ ID NO 133
<211> LENGTH: 20
<212> TYPE: DNA
<213> ORGANISM: Cladosporium cladosporioides
```

<400> SEQUENCE: 133
gcggtcggaa aggcgctcta                                               20

<210> SEQ ID NO 134
<211> LENGTH: 20
<212> TYPE: DNA
<213> ORGANISM: Cladosporium cladosporioides

<400> SEQUENCE: 134
tcggaaaggc gctctatacg                                               20

<210> SEQ ID NO 135
<211> LENGTH: 20
<212> TYPE: DNA
<213> ORGANISM: Cladosporium cladosporioides

<400> SEQUENCE: 135
cgtctggtgc cgctggataa                                               20

<210> SEQ ID NO 136
<211> LENGTH: 20
<212> TYPE: DNA
<213> ORGANISM: Cladosporium cladosporioides

<400> SEQUENCE: 136
gagcgccggg cgaggtccgc                                               20

<210> SEQ ID NO 137
<211> LENGTH: 20
<212> TYPE: DNA
<213> ORGANISM: Epicoccum nigrum

<400> SEQUENCE: 137
cactcttcta cgggcaggcc                                               20

<210> SEQ ID NO 138
<211> LENGTH: 20
<212> TYPE: DNA
<213> ORGANISM: Eurotium herbariorum

<400> SEQUENCE: 138
agactcgctt ccggggttca                                               20

<210> SEQ ID NO 139
<211> LENGTH: 19
<212> TYPE: DNA
<213> ORGANISM: Fusarium oxysporum

<400> SEQUENCE: 139
atgccaaatc tctgtaaag                                                19

<210> SEQ ID NO 140
<211> LENGTH: 20
<212> TYPE: DNA
<213> ORGANISM: Fusarium oxysporum

<400> SEQUENCE: 140
tctgtaaagt tccttcaacg                                               20

<210> SEQ ID NO 141
<211> LENGTH: 20
<212> TYPE: DNA

```
<213> ORGANISM: Fusarium oxysporum

<400> SEQUENCE: 141
tatagcccac cgtgtaatac                                              20

<210> SEQ ID NO 142
<211> LENGTH: 20
<212> TYPE: DNA
<213> ORGANISM: Geotrichum candidum

<400> SEQUENCE: 142
ttgtaagata ctttcgaaga                                              20

<210> SEQ ID NO 143
<211> LENGTH: 20
<212> TYPE: DNA
<213> ORGANISM: Mucor plumbeus

<400> SEQUENCE: 143
ttttccagat acactagaca                                              20

<210> SEQ ID NO 144
<211> LENGTH: 21
<212> TYPE: DNA
<213> ORGANISM: Mucor plumbeus

<400> SEQUENCE: 144
aataaatgtt agaatttctg c                                            21

<210> SEQ ID NO 145
<211> LENGTH: 21
<212> TYPE: DNA
<213> ORGANISM: Paecilomyces variotii

<400> SEQUENCE: 145
atgcttcggg cgcggtcccc g                                            21

<210> SEQ ID NO 146
<211> LENGTH: 20
<212> TYPE: DNA
<213> ORGANISM: Paecilomyces variotii

<400> SEQUENCE: 146
gcgcggtccc cgtctaagta                                              20

<210> SEQ ID NO 147
<211> LENGTH: 20
<212> TYPE: DNA
<213> ORGANISM: Paecilomyces variotii

<400> SEQUENCE: 147
cgtctaagta ccctggaacg                                              20

<210> SEQ ID NO 148
<211> LENGTH: 21
<212> TYPE: DNA
<213> ORGANISM: Paecilomyces variotii

<400> SEQUENCE: 148
gggacgggtg gccgtgtccg t                                            21

<210> SEQ ID NO 149
<211> LENGTH: 20
```

```
<212> TYPE: DNA
<213> ORGANISM: Paecilomyces variotii

<400> SEQUENCE: 149
acgggtggcc gtgtccgtgt                                               20

<210> SEQ ID NO 150
<211> LENGTH: 20
<212> TYPE: DNA
<213> ORGANISM: Penicillium brevicompactum

<400> SEQUENCE: 150
taacgccccc tcggggcgt                                                20

<210> SEQ ID NO 151
<211> LENGTH: 20
<212> TYPE: DNA
<213> ORGANISM: Penicillium brevicompactum

<400> SEQUENCE: 151
ccctcggggg cgtcttatag                                               20

<210> SEQ ID NO 152
<211> LENGTH: 20
<212> TYPE: DNA
<213> ORGANISM: Penicillium brevicompactum

<400> SEQUENCE: 152 ctcggggcg tcttatagcc                                                20

<210> SEQ ID NO 153
<211> LENGTH: 20
<212> TYPE: DNA
<213> ORGANISM: Penicillium chrysogenum

<400> SEQUENCE: 153
tgcaatgcga cctgcctaga                                               20

<210> SEQ ID NO 154
<211> LENGTH: 20
<212> TYPE: DNA
<213> ORGANISM: Penicillium chrysogenum

<400> SEQUENCE: 154
gcaatgcgac ctgcctagac                                               20

<210> SEQ ID NO 155
<211> LENGTH: 20
<212> TYPE: DNA
<213> ORGANISM: Penicillium chrysogenum

<400> SEQUENCE: 155
cgacctgcct agaccgagga                                               20

<210> SEQ ID NO 156
<211> LENGTH: 20
<212> TYPE: DNA
<213> ORGANISM: Penicillium citreonigrum

<400> SEQUENCE: 156
ggccagccca gaccgaggaa                                               20

<210> SEQ ID NO 157
```

```
<211> LENGTH: 20
<212> TYPE: DNA
<213> ORGANISM: Penicillium citreonigrum

<400> SEQUENCE: 157
cgtcctcctc ccgggggacg                                               20

<210> SEQ ID NO 158
<211> LENGTH: 20
<212> TYPE: DNA
<213> ORGANISM: Penicillium corylophilum

<400> SEQUENCE: 158
ctcccaccca tgtttactgt                                               20

<210> SEQ ID NO 159
<211> LENGTH: 19
<212> TYPE: DNA
<213> ORGANISM: Penicillium corylophilum

<400> SEQUENCE: 159
cacccgctct tgtaggccc                                                19

<210> SEQ ID NO 160
<211> LENGTH: 20
<212> TYPE: DNA
<213> ORGANISM: Penicillium corylophilum

<400> SEQUENCE: 160
gcttgccgac aaccatcaat                                               20

<210> SEQ ID NO 161
<211> LENGTH: 20
<212> TYPE: DNA
<213> ORGANISM: Penicillium decumbens

<400> SEQUENCE: 161
agactcgcct gcggggttca                                               20

<210> SEQ ID NO 162
<211> LENGTH: 20
<212> TYPE: DNA
<213> ORGANISM: Penicillium miczynskii

<400> SEQUENCE: 162
gatggggtgc ccgcgcccgt                                               20

<210> SEQ ID NO 163
<211> LENGTH: 20
<212> TYPE: DNA
<213> ORGANISM: Penicillium miczynskii

<400> SEQUENCE: 163
cagctctaat tgggtggtaa                                               20

<210> SEQ ID NO 164
<211> LENGTH: 20
<212> TYPE: DNA
<213> ORGANISM: Penicillium miczynskii

<400> SEQUENCE: 164
tcagccggcc ttcgggccgg                                               20
```

-continued

```
<210> SEQ ID NO 165
<211> LENGTH: 20
<212> TYPE: DNA
<213> ORGANISM: Penicillium purporogenum

<400> SEQUENCE: 165
ggaatgtacc accctccggg                                          20

<210> SEQ ID NO 166
<211> LENGTH: 20
<212> TYPE: DNA
<213> ORGANISM: Penicillium spinulosum

<400> SEQUENCE: 166
gtttcgggag cagcccccat                                          20

<210> SEQ ID NO 167
<211> LENGTH: 20
<212> TYPE: DNA
<213> ORGANISM: Penicillium spinulosum

<400> SEQUENCE: 167
ccatgtgaaa ctccttcgac                                          20

<210> SEQ ID NO 168
<211> LENGTH: 20
<212> TYPE: DNA
<213> ORGANISM: Phoma glomerata

<400> SEQUENCE: 168
ttcggggaga acttataggg                                          20

<210> SEQ ID NO 169
<211> LENGTH: 20
<212> TYPE: DNA
<213> ORGANISM: Rhizopus oryaze

<400> SEQUENCE: 169
ggattgtaga ctgtagaagt                                          20

<210> SEQ ID NO 170
<211> LENGTH: 20
<212> TYPE: DNA
<213> ORGANISM: Rhizopus oryaze

<400> SEQUENCE: 170
ctgaggtact acggtatcaa                                          20

<210> SEQ ID NO 171
<211> LENGTH: 20
<212> TYPE: DNA
<213> ORGANISM: Rhizopus oryaze

<400> SEQUENCE: 171
tcaaggttga tcttttggt                                           20

<210> SEQ ID NO 172
<211> LENGTH: 20
<212> TYPE: DNA
<213> ORGANISM: Scopulariopsis brevicaulis

<400> SEQUENCE: 172
tcagttcgtc cgggggggaga                                         20
```

```
<210> SEQ ID NO 173
<211> LENGTH: 20
<212> TYPE: DNA
<213> ORGANISM: Scopulariopsis brevicaulis

<400> SEQUENCE: 173
cagttcgtcc ggggggagaa                                                 20

<210> SEQ ID NO 174
<211> LENGTH: 20
<212> TYPE: DNA
<213> ORGANISM: Scopulariopsis candida

<400> SEQUENCE: 174
cagttcgcct ggggggagaa                                                 20

<210> SEQ ID NO 175
<211> LENGTH: 20
<212> TYPE: DNA
<213> ORGANISM: Scopulariopsis candida

<400> SEQUENCE: 175
atagcccgcc cgtgtaatac                                                 20

<210> SEQ ID NO 176
<211> LENGTH: 20
<212> TYPE: DNA
<213> ORGANISM: Stachybotrys chartarum

<400> SEQUENCE: 176
gacttgggcc ggttaatcat                                                 20

<210> SEQ ID NO 177
<211> LENGTH: 20
<212> TYPE: DNA
<213> ORGANISM: Stachybotrys chartarum

<400> SEQUENCE: 177
ggctcctctg gagtgttata                                                 20

<210> SEQ ID NO 178
<211> LENGTH: 20
<212> TYPE: DNA
<213> ORGANISM: Trichoderma viride

<400> SEQUENCE: 178
tcagttcggc gcgggggaaa                                                 20

<210> SEQ ID NO 179
<211> LENGTH: 20
<212> TYPE: DNA
<213> ORGANISM: Trichoderma viride

<400> SEQUENCE: 179
gcccgttgca taatacccotg                                                20

<210> SEQ ID NO 180
<211> LENGTH: 20
<212> TYPE: DNA
<213> ORGANISM: Ulocladium chartarum

<400> SEQUENCE: 180
gctcatccgg gcttttgccc                                                 20
```

```
<210> SEQ ID NO 181
<211> LENGTH: 20
<212> TYPE: DNA
<213> ORGANISM: Wallemia sebi

<400> SEQUENCE: 181
ccttggaata ggttggcata                                               20

<210> SEQ ID NO 182
<211> LENGTH: 20
<212> TYPE: DNA
<213> ORGANISM: Wallemia sebi

<400> SEQUENCE: 182
tggaataggt tggcatagag                                               20
```

QUALITATIVE/QUANTITATIVE DETECTION OF FUNGAL SPECIES

CROSS-REFERENCE TO RELATED APPLICATIONS

The present application claims the benefit of U.S. Patent Provisional Application Ser. No. 61/416,800 filed Nov. 24, 2010, the entire content of which is hereby incorporated by reference.

FIELD OF THE INVENTION

The invention relates to a method of identifying and quantifying species of indoor fungi in multi-species populations using a specific portion of DNA. The portion of DNA is shared amongst a variety of important indoor mold species, but it is also characterized by sufficient sequence differences that allow for unique identifications.

BACKGROUND OF THE INVENTION

It is widely understood that mold present in living or working spaces, with exposure rates as high as 50% (Gunnbjornsdottir et al., *Thorax* 2006, Mudarri and Fisk, *Indoor Air* 2007), presents a human health threat. The toxic nature of mold can lead to a number of health problems both chronic and acute. Various epidemiological studies have revealed that mold exposure is often associated with diseases and conditions such as asthma, respiratory infection, bronchitis, allergic rhinitis, and eczema (Mendell et al., *Environ Health Perspect* 2011).

As buildings become more energy efficient and better sealed, the potential for increased mold growth is actually exacerbated. As such, the incidence of mold exposure is increasing. Children and elderly people, as well as those with pre-existing respiratory problems are particularly vulnerable.

There are a number of reasons for routine testing of Indoor Air Quality (IAQ), and in particular to qualify and quantify mold species in indoor environments (mold "testing" vs. general mold "problem identification"). These reasons include the following:

1) Acceptable levels for individual mold species vary since mold species toxicity differs widely, as does spore size, weight, and other features which affect the risk to building occupants. High priority areas can be identified based on type of molds present to maximize remediation strategies for public buildings (i.e. schools, hospitals, offices) and for private residences. For mold species with severe toxic effects, immediate action from mold professionals is crucial for the safety of the building and its occupants.

2) The presence of specific group of mold species often indicates building water damage conditions even if it is not visible. Molds often hide behind walls and their presence and level of toxicity can only be indicated by the adequate IAQ tests.

3) IAQ problems can be identified by comparing known indoor mold species to known outside mold species; which can only be achieved by knowing which species are present. Thus, commonly used tests of total spore counts between the indoor molds and outdoor molds, when mold species are unknown, are largely irrelevant.

4) For a large remediation project exact mold tests can improve project control. By analyzing mold spores qualitatively as well as quantitatively before and after a mold remediation project, it can help ensure that the cleanup is complete.

5) For House and Health Insurance Purposes.

The approved ability to assess mold species rapidly and precisely can have an impact on mold remediation and overall health. Method of multiplex mold toxicity assessments described here will help to quickly pin point the sources of mold illness. Improved analysis can lead to a better understanding of mold related illness and prevention.

LIMITATIONS OF CURRENT TECHNOLOGY

While physicians can diagnose mold-related symptoms, analyzing the source and degree of mold contamination is currently a difficult and expensive task.

The tests that have been used so far by the majority of environmental laboratories in order to assess mold contamination and the potential risk to the building occupants are often flawed, time consuming, and costly to customers.

Currently, there are four basic evaluation methods of mold contamination:

1) IAQ inspectors simply confirm the presence of visible mold on walls (no species identification and quantification) and mold growth is generally classified by size of the mold colonies on walls;

2) IAQ inspectors collect air samples and send them to environmental laboratories to assesses the total number of spores from visible and hidden mold colonies (without mold species identification and quantification);

3) Collected air samples are sent to laboratories for viable spore counting from colonies grown on Petri dishes which takes up to 2 weeks (with limited and subjective traditional microscopic species identification and quantification);

The above three methods are not only, very often, subjective and inaccurate, but also time consuming, inconsistent and not comparable between the labs.

4) Recently some laboratories have started performing limited molecular analysis of molds with use of qualitative PCR (qPCR) from molds grown at least overnight on Petri dish plates where the mold species from each sample are screened in discrete PCR reactions with the use of pairs of primers specific for each mold species and expensive species-specific fluorescent probes. However, this method offers only low throughput solutions with relatively high cost per sample.

SUMMARY OF THE INVENTION

Mycelia and spores of 38 common indoor fungal species were subjected to molecular analyses in order to obtain species—specific molecular markers. The markers were next applied to the Luminex Xmap® liquid array system (Luminex Corporation (NASDAQ: LMNX)). This multiplex nucleic acid assay allows for the identification and quantification of all target mold species which are present in a given environmental sample. With the present assay methodology, at least 38 species of indoor fungi are tested for simultaneously. This invention thus provides a method of multiplexing up to 100 different analytes in parallel, with low cost and rapid profiling (more than 96 samples can be profiled in a 24 hour period).

DETAILED DESCRIPTION

Figure 1:
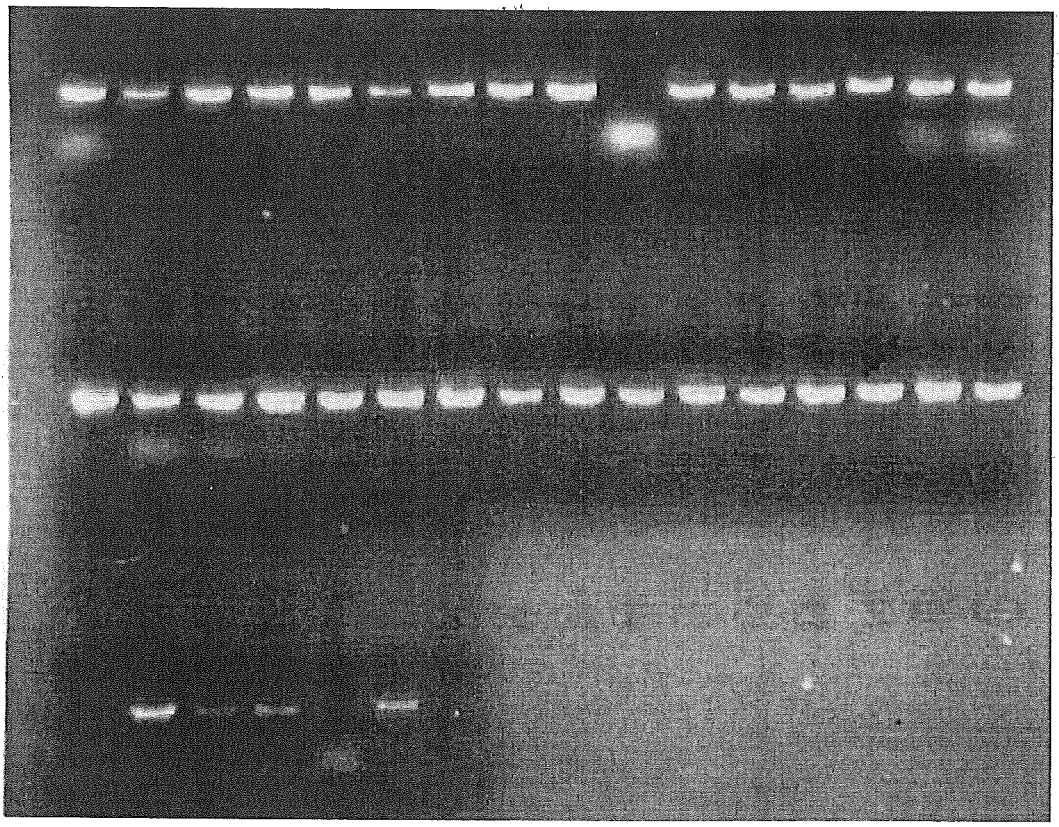
FIG. 1 shows visualization of mold PCR amplicons on 1% agarose gel; the amplicons were obtained from mold mycelia with the use of LrDNA pair of primers
Figure 2:
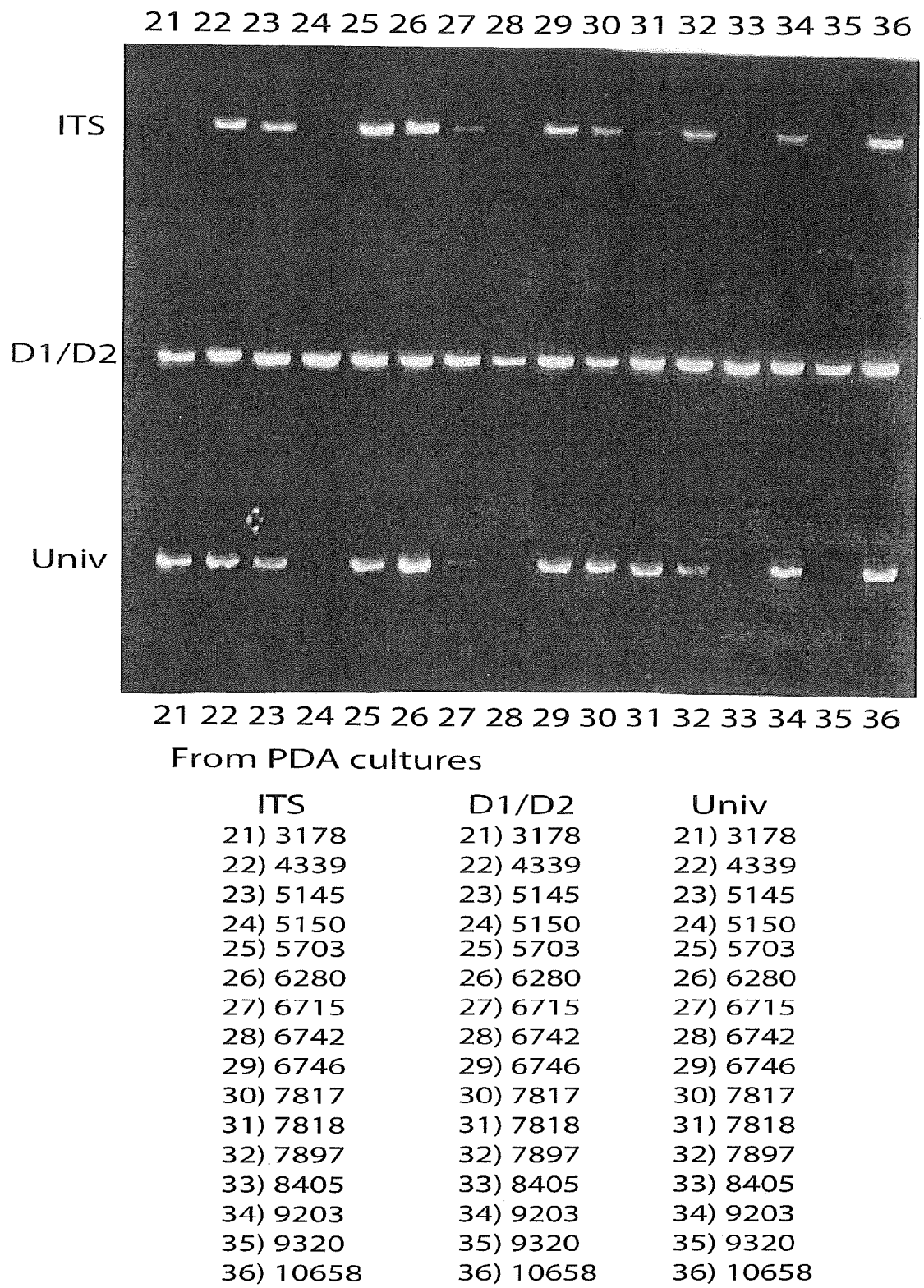
FIG. 2 shows visualization of mold PCR amplicons on 1% agarose gel; the amplicons were obtained from mold spores with the use of pairs of primers for LrDNA ($2^{nd}$ row,) and ITS ($3^{rd}$ row).

Identification in biology is the process of assigning a pre-existing individual or class name to an individual organism. Identification of organisms to individual names (or codes) may be based on individualistic natural body features, experimentally created individual markers (e.g., color dot patterns), or natural individualistic molecular markers. Every living organism contains DNA, RNA, and proteins. The hereditary information of all living organisms (except some viruses) is carried by DNA molecules. In general, closely related organisms have a high degree of homology in the molecular structure of these substances, while the molecules of organisms distantly related usually show a pattern of dissimilarity.

Molecular identification has been made possible by the availability of techniques for DNA sequencing, which allow the determination of the exact sequence of nucleotides or bases in either DNA or RNA structure which is common to more than one organism. At any location within such a sequence, the nucleotide bases found in a given position may be identical for all members of the same species and may vary between species. The species-specific DNA loci can be identified with the help of the short molecular markers (oligonucleotide or "oligo" probes) which can ferret out a particular sequence of DNA from a group of unknown nucleotides.

For this invention the large-subunit (LrDNA) in the internal transcribed spacer (ITS) region of nuclear ribosomal DNA (rDNA), common to different mold species, was used to obtain PCR amplicons of multiple mold targets and to define species-specific oligo probes.

The method of detection of the present invention is practiced using one conventional PCR reaction for all mold species in a sample, followed by capture probe microsphere-based hybridization assays containing oligo probes of interest and by quantization of the hybridized biotinylated amplicons in a multiplex liquid array system from Luminex xMAP® technology (Dunbar, Clinica Chimica Acta, 2005 "Applications of Luminex xMAP technology for rapid, high-throughput multiplexed nucleic acid detection"). This technology allows dozens of samples to be tested in parallel with highly accurate qualification and quantification of target sequences, low cost per sample, and rapid turn-around.

The method of the present invention was developed with the use of pure culture slants of the following 38 mold species obtained from the University of Alberta Fungal Collection and from the Canadian Collection of Fungal Cultures/Agriculture and *Agri*-Food Canada:

UAMH 10908 *Acremonium strictum*
UAMH 10047 *Alternaria alternata*
UAMH 7647 *Aspergillus candidus*
UAMH 9308 *Aspergillus flavus*
UAMH 9311 *Aspergillus ochraceus*
UAMH 9312 *Aspergillus penicilloides*
UAMH 4247 *Aspergillus restrictus*
UAMH 9951 *Aspergillus sclerotiorum*
UAMH 7895 *Aspergillus sydowii*
UAMH 3627 *Aspergillus terreus*
UAMH 9479 *Aspergillus ustus*
UAMH 7651 *Aspergillus versicolor*
UAMH 10765 *Aureobasidium pullulans*
UAMH 10403 *Candida glabrata*
UAMH 4146 *Cladosporium cladosporioides*
UAMH 10787 *Epicoccum nigrum*
UAMH 7767 *Eurotium herbariorum*
UAMH 3313 *Fusarium oxysporum*
UAMH 8720 *Mucor plumbeus*
UAMH 7255 *Paecilomyces variotii*
UAMH 3178 *Penicillium purpurogenum*
UAMH 4339 *Rhizopus oryzae*
UAMH 5145 *Penicillium brevicompactum*
UAMH 5150 *Penicillium miczynskii*
UAMH 5703 *Ulocladium chartarum*
UAMH 6280 *Trichoderma viride*
UAMH 6715 *Stachybotrys chartarum*
UAMH 6742 *Penicillium chrysogenum*
UAMH 6746 *Penicillium spinulosum*
UAMH 7817 *Penicillium corylophilum*
UAMH 7818 *Penicillium decumbens*
UAMH 7897 *Wallemia sebi*
UAMH 8405 *Scopulariopsis candida*
UAMH 9208 *Penicillium citreonigrum*
UAMH 9320 *Scopulariopsis brevicaulis*
UAMH 10658 *Phoma glomerata*
CCFC225569 *Geotrichum candidum*
CCFC226913 *Stachybotrys chartarum*
CCFC240363 *Aspergillus fumigatus*

The original slants of the pure mold cultures were then used to produce mycelia (cell cultures) for all mold species in the YPD (Yeast Peptone Dextrose) broth cultures and conidiospores for all mold species in the PDA (Potato Dextrose Agar) and/or CER (Cereal Agar) mold cultures. Stocks of conidia were prepared in 5% Tween80 solutions which contained from $2.5 \times 10^4$/mL to $5.4 \times 10^8$/mL of conidiospores.

DNA Extraction

After numerous trials, a method was developed for isolation of the total DNA directly from the conidia of the molds without necessity to grow them into cell cultures.

The procedure of DNA extraction from mold mycelial cells and their conidia employs a combination of Pro-K enzyme, Elu Quik (Whatman, 10462620)/Sigma (G1N-350) lysing an binding buffers, and the glass bead grinding procedure which is described as follows:

1) glass beads, spore sample, Elu Quik lysing buffer and Elu Quik binding buffer were shaken in a 1.5 mL conical tube for 4 min. and spun at 8,000×g for 1 min.
2) supernatant was removed and the remaining material treated with Sigma lysing buffer and Pro-K enzyme and then the whole DNA extracted in the binding columns according to standard Sigma procedure with the use of the GeneElute™ Mammalian Genomic DNA Miniprep Kit (Sigma-Aldrich Co., St. Louis, Mo., U.S.A.).

PCR Conditions

DNA amplifications from mycelial cells and conidia for all mold species were carried out using two sets of universal primers for isolation of the ribosomal DNA (rDNA) genome: one pair of primers for the large-subunit (LrDNA) region and the second one for the ITS region.

In the PCR cycling of the LrDNA region universal forward primer F63 (5'-GCA TAT CAA TAA GCG GAG GAA AAG-3') (SEQ ID NO:1) and universal reverse primer LR3 (5'-GGT CCG TGT TTC AAG ACG G-3') (SEQ ID NO:2) were used to produce DNA amplicons for each of the indoor mold species listed above.

PCR cycling of the ITS region included universal fungal forward primer ITS5 (5'-GGA AGT AAA AGT CGT AAC AAG G-3') (SEQ ID NO:3) and universal fungal reverse primer LR6 (5'-CGC CAG TTC TGC TTA CC-3') (SEQ ID NO:4). All PCR reverse primers were biotinylated at the 5' end to help isolate the biotinylated DNA amplicons of interest by binding them to fluorescent streptavidin. Each PCR cocktail contained 2.3 μL of 10×PCR buffer, pH 8.3 (10 mM of Tris-CHl, pH 8.3; and 50 mM of KCl; 0.01% NP-40), 1.3 µL, of 50 mM MgSO$_4$, 200 µM of each NTP, 1 unit Taq polymerase, 0.3 µM of each primer, 1-5 µL of DNA template, and the remaining volume of ddH$_2$O up to 25 pt.

The PCR thermal regime consisted of one cycle of 1 min at 95° C.; 35 cycles of 1 min at 94° C.; 1 min at 55° C.; and 1.5 min at 72° C., a final cycle of 7 min at 72° C.

All PCR amplicons were visualized on 1% agarose gels.

Sequencing

All PCR products were subjected to dye terminator cycle sequencing reactions and sequenced on Applied Biosystem's 3730xl DNA Analyzer technology, using terminators with Big Dye v. 3.1, forward and reverse primers.

In PCR assays of the LrDNA regions, the 673 by unique sequences (molecular barcodes) were produced for each mold species, as well as, 2234 by barcodes were produced for 32 mold species for the ITS region.

Figure 3:
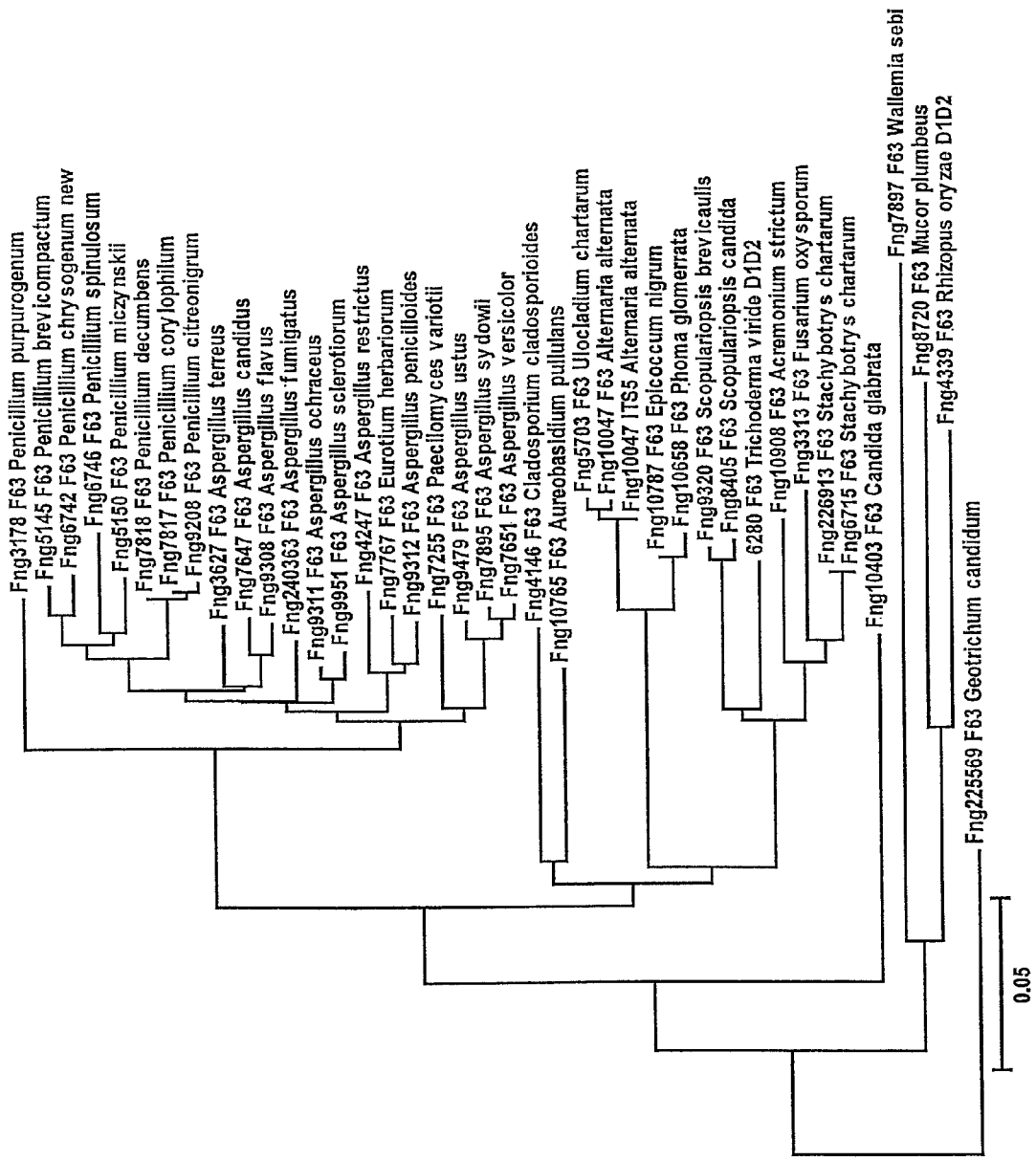
FIG. 3 shows a Neighbor Joining phylogenetic tree for indoor mold species in the LrDNA region.

Sequences were aligned by employing the Sequencher 4.6 program (Gene Codes Corporation). The phylogenetic analysis of the sequences produced shows that each mold species comprises distinctive sets of LrDNA (FIG. 3) and ITS haplotypes; no sequences are shared among species, while the sequenced individuals from the same species group closely together.

The present invention has determined that the LrDNA and ITS sequences produced for each indoor mold species show strong phylogenetic signal that can be successfully used in the diagnostics of those species. Probe selection was based on visual sequence alignment of all mold species and areas of sequence divergence among the species were analyzed for probe selection. All probes were designed to be uniform in length (20-mer); some probe lengths were modified to avoid potential secondary structures or an unstable AG, resulting in probe sequences of 20 to 24 bp. The quality of the probe was assessed using the CommOligo program.

Probes' designs were followed up by the each probe validation, then by their coupling to a different set of 5.6-µm polystyrene carboxylated microspheres using a carbodiimide method (Diaz and Fell, 2004) and multiplex liquid array system from Luminex xMAP® technology. The attached to beads capture probes (complementary in sequence to the biotinylated strands of the target amplicons) were synthesized with a 5'-end Amino C12 modification (IDT, Coralville, Iowa).

Probes were validated by testing their performance in a multiplex format first of 1-6, then of 6-38 in a capture probe hybridization assays. The capture probes, complementary in sequence to the biotinylated strand of the target amplicon, were synthesized with a 5'-end Amino C12 modification (IDT, Coralville, Iowa). Amplification with the use of biotinylated reverse primers allows for detection by Streptavidin Phycoerythrin; SAPE in Luminex system.

Each microsphere set used for probe coupling contained unique dye mixture of red and infrared fluorochromes that provided the unique identity of spectral addresses. Coupling reaction involved incubation of probes with microspheres resuspended in 0.1 M MES (2[N-morpholino]ethanesulfonic acid), pH 4.5, with a determined amount of probe (0.1 to 0.4 nmol), followed by incubation with EDC/µl and washing with 0.02% Tween 20 and 0.1% sodium dodecyl sulfate. The beads were resuspended in TE buffer (10 mM Tris-HCl, 1 mM EDTA; pH 8) and kept in the dark at 4° C.

Capture probe hybridization assay was based upon detection of 5'-biotin-labeled PCR amplicons hybridized to specific capture probes covalently bound to the carboxylate surface of the microspheres. Hybridization reactions were carried out in 96-well plates in the presence of a 3 M TMAC solution (tetramethyl ammonium chloride—50 mM Tris [pH 8.0]—1 mM EDTA [pH 8.0]—0.1% sodium dodecyl sulfate), consisted of biotinylated amplicons diluted in TE buffer (pH 8) and 1.5×TMAC solution containing a bead mixture of approximately 5,000 microspheres of each set of probes. Prior to hybridization, the reaction mixture was incubated for 5 mM at 95° C. in a mastercycler (Brinkman). This step was followed by 15 mM of incubation at 55° C. After hybridization, the microspheres were pelleted by centrifugation and the supernatant was removed. The plate was again incubated and the hybridized amplicons were labeled with the fluorescent reporter molecule, streptavidin R-phycoerythrin.

From the obtained reactions 100 microspheres of each set (100 replicate measurements) were analyzed on the Luminex 100. A blank and a set of positive and negative controls were included in the analyses. MFI (median fluorescence intensity) values were calculated with a digital signal processor and the Luminex proprietary software. Assays and the samples were run in duplicate. The signal-to-background ratio corresponds to the MFI signals of positive controls versus the background fluorescence of samples containing all components except the target DNA.

The limits of the Luminex system were tested in several assays with the range of quantities from 150 to 10 fmol of biotinylated amplicons in the presence of the reverse and complement oligo probes. The sensitivity of the assays was also estimated using serial dilutions of amplicons (1000 to $10^{-3}$ ng). The quantitative/qualitative method provided by the invention has been developed to detect indoor fungal species in the mixed species environmental samples through:

1) the use of a new, optimized method of total DNA extraction for indoor mold species;
2) detection of two specific genomic regions (section of LrDNA region and section of ITS region) which are suitable for obtaining unique molecular barcodes (i.e. genetic profiles) for each of the indoor fungal species;
3) production of those molecular barcodes in the regular PCR assays with the use of one pair of primers for the LrDNA region and one pair of primers for the ITS region for all 38 mold species listed in the method;
4) based on their molecular barcodes, designing of one to several molecular probes specific for each of 38 mold species;
5) adaptation of the Luminex Xmap® liquid array system to using those probes for rapid, accurate, and standardized discrimination and quantification of mixed fungal species samples, with no need for growing fungal cell cultures at any time.

While this invention has been described in connection with the specific examples and methods, it will be appreciated by the skilled artisan that it is capable of further modifications. This application is intended to cover any variations, uses, or adaptations of the invention following, in general, the principles of the invention and including such departures from the present disclosure as come within known or customary practice within the ken of the skilled artisan. The claims that follow are not intended to limit the scope of invention in any way, but to define certain essential features of the invention described in detail herein.

List of LrDNA and ITS Barcodes for Indoor Mold Species.

LrDNA Barcodes

Fng3178_F63_*Penicillium_purpurogenum* (SEQ ID NO:5)
Fng3313_F63_*Fusarium_oxysporum* (SEQ ID NO:6)
Fng3627_F63_*Aspergillus_terreus* (SEQ ID NO:7)
Fng4146_F63_*Cladosporium_cladosporioides* (SEQ ID NO:8)
Fng4247_F63_*Aspergillus_restrictus* (SEQ ID NO:9)

Fng4339_F63_Rhizopus_oryzae_D1D2 (SEQ ID NO:10)
Fng5145_F63_Penicillium_brevicompactum (SEQ ID NO:11)
Fng5150_F63_Penicillium_miczynskii (SEQ ID NO:12)
Fng5703_F63_Ulocladium_chartarum (SEQ ID NO:13)
6280_F63_Trichodermaviride_D1D2 (SEQ ID NO:14)
Fng6742_F63_Penicillium_chrysogenum (SEQ ID NO:15)
Fng6746_F63_Penicillium_spinulosum (SEQ ID NO:16)
Fng7255_F63_Paecilomyces_variotii (SEQ ID NO:17)
Fng7647_F63_Aspergillus_candidus (SEQ ID NO:18)
Fng7651_F63_Aspergillus_versicolor (SEQ ID NO:19)
Fng7767_F63_Eurotiumher_bariorum (SEQ ID NO:20)
Fng7817_F63_Penicillium_corylophilum (SEQ ID NO:21)
Fng7895_F63_Aspergillus_sydowii (SEQ ID NO:22)
Fng7897_F63_Wallemia_sebi (SEQ ID NO:23)
Fng7818_F63_Penicillium_decumbens (SEQ ID NO:24)
Fng8405_F63_Scopulariopsis_candida (SEQ ID NO:25)
Fng8720_F63_Mucor_plumbeus (SEQ ID NO:26)
Fng9208_F63_Penicillium_chreonigrum (SEQ ID NO:27)
Fng9308_F63_Aspergillus_flavus (SEQ ID NO:28)
Fng9311_F63_Aspergillus_ochraceus (SEQ ID NO:29)
Fng9312_F63_Aspergillus_penicilloides (SEQ ID NO:30)
Fng9320_F63_Scopulariopsis_brevicaulis (SEQ ID NO:31)
Fng9479_F63_Aspergillus_ustus (SEQ ID NO:32)
Fng9951_F63_Aspergillus_sclerotiorum (SEQ ID NO:33)
Fng10047_F63_Alternaria_alternata (SEQ ID NO:34)
Fng10403_F63_Candida_glabrata (SEQ ID NO:35)
Fng10658_F63_Phoma_glomerata (SEQ ID NO:36)
Fng10765_F63_Aureobasidium_pullulans (SEQ ID NO:37)
Fng10787_F63_Epicoccum_nigrum (SEQ ID NO:38)
Fng10908_F63_Acremonium_strictum (SEQ ID NO:39)
Fng225569_F63_Geotrichum_candidum (SEQ ID NO:40)
Fng226913_F63_Stachybotrys_chartarum (SEQ ID NO:41)
Fng240363_F63_Aspergillus_fumigatus (SEQ ID NO:42)
ITS Barcodes
Fng3178_ITS5_Penicillium_purpurogenum (SEQ ID NO:43)
Fng3178_LR6_Penicillium_purpurogenum (SEQ ID NO:44)
Fng3313_ITS5_Fusarium oxysporum (SEQ ID NO:45)
Fng3313_LR6_Fusarium_oxysporum (SEQ ID NO:46)
Fng4146_ITS5_Cladosporioum_cladosprioides (SEQ ID NO:47)
Fng4146_LR6_Cladosporium_cladosprioides (SEQ ID NO:48)
Fng4247_ITS5_Aspergillus_restrictus (SEQ ID NO:49)
Fng4247_LR6_Aspergillus_restrictus (SEQ ID NO:50)
Fng4339_ITS5_Rhizopus_oryzae (SEQ ID NO:51)
Fng4339_LR6_Rhizopus_oryzae_(SEQ ID NO:52)
Fng5145_ITS5_Penicillium_brevicompactum (SEQ ID NO:53)
Fng5145_LR6_Penicillium_brevicompactum (SEQ ID NO:54)
Fng5703_ITS5_Ulocladium_chartarum (SEQ ID NO:55)
Fng5703_LR6_Ulocladium_chartarum (SEQ ID NO:56)
Fng6280_ITS5_Trichoderma_viride (SEQ ID NO:57)
Fng6280_LR6_Trichoderma_viride (SEQ ID NO:58)
Fng6715_ITS5_Stachybotrys_chartarum (SEQ ID NO:59)
Fng6715_LR6_Stachybotrys_chartarum (SEQ ID NO:60)
Fng6742_ITS5_Penicillium_chrysogenum (SEQ ID NO:61)
Fng6742_LR6_Penicillium_chrysogenum (SEQ ID NO:62)
Fng6746_ITS5_Penicillium_spinulosum (SEQ ID NO:63)
Fng6746_LR6_Penicillium_spinulosum (SEQ ID NO:64)
Fng7255_ITS5_Paecilomyces_variotii (SEQ ID NO:65)
Fng7255_LR6_Paecilomyces_variotii (SEQ ID NO:66)
Fng7651_ITS5_Aspergillus_versicolor (SEQ ID NO:67)
Fng7651_LR6_Aspergillus_versicolor (SEQ ID NO:68)
Fng7767_ITS5_Eurotium_herbariorum (SEQ ID No:69)
Fng7767_LR6_Eurotium_herbariorum (SEQ ID NO:70)
Fng7817_ITS5_Penicillium_corylophilum (SEQ ID NO:71)
Fng7817_LR6_Penicillium_corylophilum (SEQ ID NO:72)
Fng7818_ITS5_Penicillium_decumbens (SEQ ID NO:73)
Fng7818_LR6_Penicillium_decumbens (SEQ ID NO:74)
Fng7895_ITS5_Aspergillus_sydowii (SEQ ID NO:75)
Fng7895_LR6_Aspergillus_sydowii (SEQ ID NO:76)
Fng7897_ITS5_Wallemiasebi (SEQ ID NO:77)
Fng7897_LR6_Wallemiasebi (SEQ ID NO:78)
Fng8720_ITS5_Mucor_plumbeus (SEQ ID NO:79)
Fng8720_LR6_Mucor_plumbeus (SEQ ID NO:80)
Fng9208_ITS5_Penicillium_citreonigrum (SEQ ID NO:81)
Fng9208_LR6_Penicillium_citreonigrum (SEQ ID NO:82)
Fng9308_ITS5_Aspergillus_flavus (SEQ ID NO:83)
Fng9308_LR6_Aspergillus_flavus (SEQ ID NO:84)
Fng9311_ITS5_Aspergillus_ochraceus (SEQ ID NO:85)
Fng9311_LR6_Aspergillus_ochraceus (SEQ ID NO:86)
Fng9312_ITS5_Aspergillus_penicilloides (SEQ ID NO:87)
Fng9312_LR6_Aspergillus_penicilloides (SEQ ID NO:88)
Fng9479_ITS5_Aspergillus_ustus (SEQ ID NO:89)
Fng9479_LR6_Aspergillus_ustus (SEQ ID NO:90)
Fng9951_ITS5_Aspergillus_sclerotiorum (SEQ ID NO:91)
Fng9951_LR6_Aspergillus_sclerotiorum (SEQ ID NO:92)
Fng10047_ITS5_Alternaria_alternata (SEQ ID NO:93)
Fng10047_LR6_Alternaria_alternata (SEQ ID NO:94)
Fng10403_ITS5_Candida_glabrata (SEQ ID NO:95)
Fng10403_LR6_Candida_glabrata (SEQ ID NO:96)
Fng10658_ITS5_Phoma_glomerata (SEQ ID NO:97)
Fng10658_LR6_Phoma_glomerata (SEQ ID NO:98)
Fng10765_ITS5_Aureobasidium_pullulans (SEQ ID NO:99)
Fng10765_LR6_Aureobasidium_pullulans (SEQ ID NO:100)
Fng10787_ITS5_Epicoccum_nigrum (SEQ ID NO:101)
Fng10787_LR6_Epicoccum_nigrum (SEQ ID NO:102)
Fng10908_ITS5_Acremonium_strictum (SEQ ID NO:103)
Fng10908_LR6_Acremonium_strictum (SEQ ID NO:104)
Fng225569_ITS5_Geotrichum_candidum (SEQ ID NO:105)
Fng225569_LR6_Geotrichum_candidum (SEQ ID NO:106)
Fng240363_ITS5_Aspergillus_fumigatus (SEQ ID NO:107)
Fng240363_LR6_Aspergillus_fumigatus (SEQ ID NO:108)
List of Probes Designed for Indoor Mold Species
Acr_str_AcS351_(1338) AGGGAAGCATTCATGACCAG (SEQ ID NO:109)
Acr_str_AcS391_(1367) GCTTGGTTGAACATCCGGCG (SEQ ID NO:110)
Alt_alt_AA397_(1384) CCGGGTTTTTACCCGGTGCA (SEQ ID NO:111)
Asp_can_AC467_(1454) GCCGGTCAGCGGCTCCCGGA (SEQ ID NO:112)
Asp_fla_AF1374_(1361) ACTCGCCTCCAGGGTTCAGC (SEQ ID NO:113)
Asp_fla_AF1506_(1493) TCCGGGGCACCTTATAGCCG (SEQ ID NO:114)

Asp_fum_AF485_(1472) GGAATGTATCACCTCTCGGGGTGTC (SEQ ID NO:115)
Asp_och_AO485_(1472) GGAATGTAGCACCCTTCGGG (SEQ ID NO:116)
Asp_och_AO505_(1492) CTTCGGGGTGCCTTATAGCC (SEQ ID NO:117)
Asp_pen_AP496_(1480) AACGCCCCTCCGGGGGCGTC (SEQ ID NO:118)
Asp_res_AR113_(1099) GCTCTGGAATGGGCCATCAGA (SEQ ID NO:119)
Asp_res_AR485_(1472) GGAATGTAACACCTCTCGGGG (SEQ ID NO:120)
Asp_scl_ASc493_(1480) AGTGCCCCTACGGGGGCACC (SEQ ID NO:121)
Asp_syd_As_870_ITS5 ACCATTTTTCTTCAGGTTGA (SEQ ID NO:122)
Asp_ter_AT392_(1379) TCAGCCGGGCTTCGGCCCGG (SEQ ID NO:123)
Asp_ter_AT400_(1387) GGGCTTCGGCCCGGTGTACT (SEQ ID NO:124)
Asp_ust_AU453_(1471) AGGAATGTGTCGCCCTCCGG (SEQ ID NO:125)
Asp_ust_AU462_(1481) TCGCCCTCCGGGGCGTCTTA (SEQ ID NO:126)
Asp_ver_AV451_(1438) GCGTCGGTTCGGGCGGCCGG (SEQ ID NO:127)
Asp_ver_AV643_(1630) GTAATGGTCACAAACGACCC (SEQ ID NO:128)
Aur_pul_AuP35_(1022) GCTGGCCTCTGGTCCGCATT (SEQ ID NO:129)
Aur_pul_AuP158_(1145) ACCGGCTCAGGCACCTTCTG (SEQ ID NO:130)
Aur_pul_AuP420_(1407) GCCCACTCAGTCTTGTCCAG (SEQ ID NO:131)
Ca_gla_CG614_(1601) GATACTTGTTATCTAGGATG (SEQ ID NO:132)
Cla_cla_CC154_(1141) GCGGTCGGAAAGGCGCTCTA (SEQ ID NO:133)
Cla_cla_CC159_(1146) TCGGAAAGGCGCTCTATACG (SEQ ID NO:134)
Cla_cla_CC456_(1442) CGTCTGGTGCCGCTGGATAA (SEQ ID NO:135)
Cla_cla_CC571_(1558) GAGCGCCGGGCGAGGTCCGC (SEQ ID NO:136)
Epi_ig_EP424_(1411) CACTCTTCTACGGGCAGGCC (SEQ ID NO:137)
Eur_her_EH372_(1359) AGACTCGCTTCCGGGGTTCA (SEQ ID NO:138)
Fus_oxy_FO163_(1150) ATGCCAAATCTCTGTAAAG (SEQ ID NO:139)
Fus_oxy_FO176_(1163) TCTGTAAAGTTCCTTCAACG (SEQ ID NO:140)
Fus_oxy_FO530_(1518) TATAGCCCACCGTGTAATAC (SEQ ID NO:141)
Geo_ca_GC177_(1165) TTGTAAGATACTTTCGAAGA (SEQ ID NO:142)
Muc_plu_MP79_(1066) TTTTCCAGATACACTAGACA (SEQ ID NO:143)
Muc_plu_MP640_(1627) AATAAATGTTAGAATTTCTGC (SEQ ID NO:144)
Pae_var_PV79_(1069) ATGCTTCGGGCGCGGTCCCCG (SEQ ID NO:145)
Pae_var_PV89_(1076) GCGCGGTCCCCGTCTAAGTA (SEQ ID NO:146)
Pae_var_PV100_(1087) CGTCTAAGTACCCTGGAACG (SEQ ID NO:147)
Pae_var_PV154_(1141) GGGACGGGTGGCCGTGTCCGT (SEQ ID NO:148)
Pae_var_PV158_(1145) ACGGGTGGCCGTGTCCGTGT (SEQ ID NO:149)
Pe_bre_PB462_(1479) TAACGCCCCCTCGGGGGCGT (SEQ ID NO:150)
Pe_bre_PB502_(1489) CCCTCGGGGGCGTCTTATAG (SEQ ID NO:151)
Pe_bre_PB505_(1492) CTCGGGGGCGTCTTATAGCC (SEQ ID NO:152)
Pe_chr_PCh550_(1536) TGCAATGCGACCTGCCTAGA (SEQ ID NO:153)
Pe_chr_PCh551_(1538) GCAATGCGACCTGCCTAGAC (SEQ ID NO:154)
Pe_chr_PCh561_(1548) CGACCTGCCTAGACCGAGGA (SEQ ID NO:155)
Pe_cit_PC563_(1549) GGCCAGCCCAGACCGAGGAA (SEQ ID NO:156)
Pe_citr_Pci695_IT5 CGTCCTCCTCCCGGGGGACG (SEQ ID NO:157)
Pe_cor_Pco118_ITS5 CTCCCACCCATGTTTACTGT (SEQ ID NO:158)
Pe_cor_Pco814_ITS5 CACCCGCTCTTGTAGGCCC (SEQ ID NO:159)
Pe_cor_Pco849_ITS5 GCTTGCCGACAACCATCAAT (SEQ ID NO:160)
Pe_dec_PD372_(1359) AGACTCGCCTGCGGGGTTCA (SEQ ID NO:161)
Pe_mic_PM152_(1144) GATGGGGTGCCCGCGCCCGT (SEQ ID NO:162)
Pe_mic_PM220_(1207) CAGCTCTAATTGGGTGGTAA (SEQ ID NO:163)
Pe_mic_PM392_(1379) TCAGCCGGGCCTTCGGGCCGG (SEQ ID NO:164)
Pe_pur_PP485_(1472) GGAATGTACCACCCTCCGGG (SEQ ID NO:165)
Pe_spi_PS80_(1067) GTTTCGGGAGCAGCCCCCAT (SEQ ID NO:166)
Pe_spi_PS175_(1162) CCATGTGAAACTCCTTCGAC (SEQ ID NO:167)
Pho_glo_PG506_(1493) TTCGGGGAGAACTTATAGGG (SEQ ID NO:168)
Rhi_ory_RO57_(1044) GGATTGTAGACTGTAGAAGT (SEQ ID NO:169)
Rhi_ory_RO620_(1607) CTGAGGTACTACGGTATCAA (SEQ ID NO:170)
Rhi_ory_RO644_(1631) TCAAGGTTGATCTTTTTGGT (SEQ ID NO:171)
Sco_bre_ScB454_(1441) TCAGTTCGTCCGGGGGGAGA (SEQ ID NO:172)
Sco_bre_ScB455_(1442) CAGTTCGTCCGGGGGAGAA (SEQ ID NO:173)
Sco_ca_ScC455_(1442) CAGTTCGCCTGGGGGGAGAA (SEQ ID NO:174)
Sco_ca_ScC534_(1521) ATAGCCCGCCCGTGTAATAC (SEQ ID NO:175)
Sta_cha_SC373_(1360) GACTTGGGCCGGTTAATCAT (SEQ ID NO:176)
Sta_cha_SC493_(1472) GGCTCCTCTGGAGTGTTATA (SEQ ID NO:177)
Tri_vir_TV454_(1441) TCAGTTCGGCGCGGGGGAAA (SEQ ID NO:178)
Tri_vir_TV539_(1526) GCCCGTTGCATAATACCCTG (SEQ ID NO:179)
Ulo_cha_UC390_(1377) GCTCATCCGGGCTTTTGCCC (SEQ ID NO:180)
Wal_seb_WS113_(1100) CCTTGGAATAGGTTGGCATA (SEQ ID NO:181)
Wal_seb_WS117_(1101) TGGAATAGGTTGGCATAGAG (SEQ ID NO:182)

The invention claimed is:

1. A method for detecting mold species in an indoor environment sample, comprising
obtaining total DNA from said sample;
amplifying said DNA by a polymerase chain reaction (PCR) using at least one pair of primers comprising sequences specific to a large subunit genomic region (LrDNA region) of said mold species, thereby generating DNA barcode amplicons comprising species-specific DNA sequences from mold species present in said sample;
performing an assay comprising hybridization to said amplicons using at least one oligonucleotide probe specific to each of the following mold species: *Acremonium strictum, Alternaria alternata, Aspergillus candidus, Aspergillus flavus, Aspergillus fumigates, Aspergillus ochraceus, Aspergillus penicilloides, Aspergillus restrictus, Aspergillus sclerotiorum, Aspergillus terreus, Aspergillus ustus, Aspergillus versicolor, Aureobasidium pullulans, Candida glabrata, Cladosporium cladosporioides, Epicoccum nigrum, Eurotium herbariorum, Fusarium oxysporum, Mucor plumbeus, Paecilomyces variotii, Penicillium purpurogenum, Rhizopus oryzae, Penicillium brevicompactum, Penicillium miczynskii, Ulocladium chartarum, Trichoderma viride, Stachybotrys chartarum, Penicillium chrysogenum, Penicillium spinulosum, Penicillium decumbens, Wallemia sebi, Scopulariopsis candida, Penicillium citreonigrum, Scopulariopsis brevicaulis, Phoma glomerata,* and *Geotrichum candidum,* wherein the oligonucleotide probes are selected from SEQ ID NOS: 109-121, 123-156, and 161-182; and
detecting hybridization of the oligonucleotide probes to the barcode amplicons.

2. The method of claim 1, wherein said sample comprises spores or mycelia of said mold species, and total DNA is extracted from said spores or mycelia without cell culturing.

3. The method of claim 1, wherein the PCR is performed using at least an additional pair of primers specific to an internal transcribed spacer (ITS) region of said mold species.

4. The method of claim 3, wherein said assay further comprises use of at least one additional oligonucleotide probe specific to either of the mold species *Aspergillus sydowii* and *Penicillium corylophilum,* said at least one oligonucleotide probes being selected additional from SEQ ID NOS: 122, 157, 158, 159, and 160.

5. The method of claim 3, wherein one primer pair is specific to the LrDNA region, and the second primer pair is specific to the ITS region.

6. The method of claim 3, wherein said PCR produces amplicons which contain species-specific sequences in the LrDNA region and species-specific sequences in the ITS region.

7. The method of claim 1, wherein one primer of said at least one pair of primers further comprises a detectable label.

8. The method of claim 7, wherein said is biotin.

9. The method of claim 1, wherein said species-specific oligonucleotide probes are attached to microspheres in a multiplex array system.

10. The method of claim 9, wherein said at least one species-specific oligonucleotide probe is synthesized with a 5'-end Amino C12 modification.

11. The method of claim 4, wherein said group of mold species comprises the following:
UAMH 10908 *Acremonium strictum*
UAMH 10047 *Alternaria alternata*
UAMH 7647 *Aspergillus candidus*
UAMH 9308 *Aspergillus flavus*
UAMH 9311 *Aspergillus ochraceus*
UAMH 9312 *Aspergillus penicilloides*
UAMH 4247 *Aspergillus restrictus*
UAMH 9951 *Aspergillus sclerotiorum*
UAMH 7895 *Aspergillus sydowii*
UAMH 3627 *Aspergillus terreus*
UAMH 9479 *Aspergillus ustus*
UAMH 7651 *Aspergillus versicolor*
UAMH 10765 *Aureobasidium pullulans*
UAMH 10403 *Candida glabrata*
UAMH 4146 *Cladosporium cladosporioides*
UAMH 10787 *Epicoccum nigrum*
UAMH 7767 *Eurotium herbariorum*
UAMH 3313 *Fusarium oxysporum*
UAMH 8720 *Mucor plumbeus*
UAMH 7255 *Paecilomyces variotii*
UAMH 3178 *Penicillium purpurogenum*
UAMH 4339 *Rhizopus oryzae*
UAMH 5145 *Penicillium brevicompactum*
UAMH 5150 *Penicillium miczynskii*
UAMH 5703 *Ulocladium chartarum*
UAMH 6280 *Trichoderma viride*
UAMH 6715 *Stachybotrys chartarum*
UAMH 6742 *Penicillium chrysogenum*

UAMH 6746 *Penicillium spinulosum*
UAMH 7817 *Penicillium corylophilum*
UAMH 7818 *Penicillium decumbens*
UAMH 7897 *Wallemia sebi*
UAMH 8405 *Scopulariopsis candida*
UAMH 9208 *Penicillium citreonigrum*
UAMH 9320 *Scopulariopsis brevicaulis*
UAMH 10658 *Phoma glomerata*
CCFC225569 *Geotrichum candidum*
CCFC226913 *Stachybotrys chartarum*
CCFC240363 *Aspergillus fumigatus*.

12. The method of claim 11, wherein said method is performed in an array format.

13. The method of claim 12, wherein said array is a multiplex liquid array assay.

14. The method of claim 13, wherein detection of each mold species is based upon detection of labeled PCR amplicons hybridized to capture probes covalently bound to a surface of an array device in the presence of a fluorescent reporter molecule, and wherein upon hybridization, said microspheres bearing said target amplicons are classified by their spectral addresses within the array.

15. The method of claim 14, wherein said fluorescent reporter molecule is streptavidin R-phycoerythrin.

16. The method of claim 14, further comprising identifying and quantifying mold species present in said sample based on fluorescence detection.

17. The method of claim 1, further comprising quantifying mold species in said sample.

18. The method of claim 4, further comprising identifying mold species in said sample by determining the presence of at least one DNA barcode selected from SEQ ID NOS: 5-108 in said sample.

19. The method of claim 1 wherein said at least one pair of primers comprises SEQ ID NOS: 1 and 2.

20. The method of claim 4 wherein said additional pair of primers comprises SEQ ID NOS: 3 and 4.

* * * * *